US008084592B2

(12) United States Patent
Bot et al.

(10) Patent No.: US 8,084,592 B2
(45) Date of Patent: Dec. 27, 2011

(54) MULTIVALENT ENTRAIN-AND-AMPLIFY IMMUNOTHERAPEUTICS FOR CARCINOMA

(75) Inventors: Adrian Ion Bot, Valencia, CA (US);
Chih-Sheng Chiang, Chatsworth, CA (US); David C. Diamond, West Hills, CA (US); Jian Gong, Northridge, CA (US); Kent Andrew Smith, Ventura, CA (US); Liping Liu, Manassas, VA (US); Xiping Liu, Temple City, CA (US); Zhiyong Qiu, Los Angeles, CA (US)

(73) Assignee: MannKind Corporation, Valencia, CA (US)

( * ) Notice: Subject to any disclaimer, the term of this patent is extended or adjusted under 35 U.S.C. 154(b) by 282 days.

(21) Appl. No.: 11/455,279

(22) Filed: Jun. 16, 2006

(65) Prior Publication Data

US 2007/0003563 A1 Jan. 4, 2007

Related U.S. Application Data

(60) Provisional application No. 60/691,581, filed on Jun. 17, 2005.

(51) Int. Cl.
*C07H 21/02* (2006.01)
(52) U.S. Cl. ............. 536/23.1; 530/328; 514/44 R; 514/1.1
(58) Field of Classification Search .................. None
See application file for complete search history.

(56) References Cited

U.S. PATENT DOCUMENTS

| | | | |
|---|---|---|---|
| 5,464,756 A * | 11/1995 | Henner et al. ............... 435/69.1 |
| 5,538,866 A | 7/1996 | Israeli et al. |
| 5,620,886 A | 4/1997 | Brichard et al. |
| 5,683,886 A | 11/1997 | van der Bruggen et al. |
| 5,747,271 A | 5/1998 | Boon-Falleur et al. |
| 5,804,381 A | 9/1998 | Chen et al. |
| 5,830,753 A | 11/1998 | Coulie et al. |
| 5,840,839 A * | 11/1998 | Wang et al. ............... 530/325 |
| 5,874,560 A | 2/1999 | Kawakami et al. |
| 5,994,523 A | 11/1999 | Kawakami et al. |
| 6,025,191 A | 2/2000 | Pfreundschuh |
| 6,709,844 B1 | 3/2004 | Levy |
| 6,861,234 B1 | 3/2005 | Simard et al. |
| 6,977,074 B2 | 12/2005 | Kundig et al. |
| 6,994,851 B1 | 2/2006 | Kundig et al. |
| 7,232,682 B2 | 6/2007 | Simard et al. |
| 7,252,824 B2 * | 8/2007 | Simard et al. ............... 424/184.1 |
| 2003/0138808 A1 | 7/2003 | Simard et al. |
| 2003/0180949 A1 | 9/2003 | Levy |
| 2003/0215425 A1 | 11/2003 | Simard et al. |
| 2003/0220239 A1 | 11/2003 | Simard et al. |
| 2003/0228634 A1 | 12/2003 | Simard et al. |
| 2004/0063120 A1 | 4/2004 | Beer et al. |
| 2004/0180354 A1 | 9/2004 | Simard et al. |
| 2004/0203051 A1 | 10/2004 | Simard et al. |
| 2005/0069982 A1 | 3/2005 | Simard et al. |
| 2005/0079152 A1 | 4/2005 | Bot et al. |
| 2005/0118186 A1 | 6/2005 | Chiang et al. |
| 2005/0130920 A1 | 6/2005 | Simard et al. |
| 2005/0142144 A1 | 6/2005 | Simard et al. |
| 2005/0221440 A1 | 10/2005 | Simard et al. |
| 2005/0260234 A1 | 11/2005 | Simard et al. |
| 2005/0287068 A1 | 12/2005 | Bot et al. |
| 2006/0008468 A1 | 1/2006 | Chiang et al. |
| 2006/0057673 A1 | 3/2006 | Liu et al. |
| 2006/0063913 A1 | 3/2006 | Liu et al. |
| 2006/0094661 A1 | 5/2006 | Liu et al. |
| 2006/0153844 A1 | 7/2006 | Kundig et al. |
| 2006/0153858 A1 | 7/2006 | Kundig et al. |
| 2006/0159689 A1 | 7/2006 | Chiang et al. |
| 2006/0159694 A1 | 7/2006 | Chiang et al. |
| 2006/0165711 A1 | 7/2006 | Bot et al. |
| 2006/0269521 A1 | 11/2006 | Levy |
| 2007/0004662 A1 | 1/2007 | Qiu et al. |
| 2007/0049533 A1 | 3/2007 | Liu et al. |
| 2007/0060518 A1 | 3/2007 | Liu et al. |
| 2007/0060524 A1 | 3/2007 | Liu et al. |
| 2007/0184062 A1 | 8/2007 | Simard et al. |
| 2007/0269464 A1 | 11/2007 | Simard |
| 2008/0014211 A1 | 1/2008 | Bot et al. |

FOREIGN PATENT DOCUMENTS

| | | |
|---|---|---|
| AU | 739189 | 7/1998 |
| EP | 1118860 * | 7/2001 |
| WO | WO 99/02183 A | 1/1999 |
| WO | WO 02/081646 | 10/2002 |
| WO | WO 03/011332 A | 2/2003 |
| WO | WO 2004/011483 A2 | 2/2004 |
| WO | WO 2004/018666 | 3/2004 |
| WO | WO 2004/022709 | 3/2004 |
| WO | WO 2004/112825 | 12/2004 |
| WO | WO 2004/112825 A | 12/2004 |
| WO | WO 2005/002621 A2 | 1/2005 |

(Continued)

OTHER PUBLICATIONS

Dorlands on-line Medical Dictionary definition of analogue, Jun. 4, 2007.*
Gure, A.O. et al. 1997. "SSX: A Multigene Family with Several Members Transcribed in Normal Testis and Human Cancer." *Int. J. Cancer* 72: 965-971.
Pascolo et al. 1997. "HLA-A2.1-restricted Education and Cytolytic Activity of CD8+ T Lymphocytes from β2 Microglobulin (β2m) HLA-A2.1 Monochain Transgenic H-2Db β2m Double Knockout Mice." *J. Exp. Med.* 185(12): 2043-2051.
U.S. Appl. No. 09/560,465, filed Apr. 28, 2000. Title: Epitope Synchronization in Antigen Presenting Cells.
U.S. Appl. No. 09/561,571, filed Apr. 28, 2000. Title: Epitope Clusters.

(Continued)

*Primary Examiner* — Misook Yu
*Assistant Examiner* — Mark Halvorson
(74) *Attorney, Agent, or Firm* — Davis Wright Tremaine LLP

(57) ABSTRACT

The present invention provides a method of treating a cell proliferative disease such as cancer by providing to a subject in need thereof an immunogenic composition comprising plasmid and peptide(s) or analogues thereof. In embodiments of the present invention there is provided methods and compositions for inducing, entraining, and/or amplifying the immune response to MHC class-I restricted epitopes of carcinoma antigens to generate an effective anti-cancer immune response.

37 Claims, 23 Drawing Sheets

FOREIGN PATENT DOCUMENTS

| | | |
|---|---|---|
| WO | WO 2005/010190 A | 2/2005 |
| WO | WO 2006/009920 | 1/2006 |
| WO | WO 2006/009920 A2 | 1/2006 |
| WO | WO 2006/071983 A | 7/2006 |

OTHER PUBLICATIONS

U.S. Appl. No. 09/561,572, filed Apr. 28, 2000. Title: Expression Vectors Encoding Epitopes of Target-Associated Antigens.

U.S. Appl. No. 09/999,186, filed Nov. 7, 2001. Title: Methods of Commercializing and Antigen.

U.S. Appl. No. 11/323,520, filed Dec. 29, 2005. Title: Methods to Bypass CD4+ Cells in the Induction of an Immune Response.

U.S. Appl. No. 11/418,397, filed May 3, 2006. Titled: Methods of Inducing a CTL Response.

U.S. Appl. No. 11/418,497, filed May 3, 2006. Title: Methods of Inducing a CTL Response.

U.S. Appl. No. 11/772,811, filed Jul. 2, 2007. Title: Anti-Neovasculature Preparations for Cancer.

U.S. Appl. No. 12/070,156, filed Feb. 15, 2008. Title: Method for Enhancing T Cell Response.

U.S. Appl. No. 60/282,211, filed Apr. 6, 2001. Title: Epitope Sequences.

U.S. Appl. No. 60/337,017, filed Nov. 7, 2001. Title: Epitope Sequences.

U.S. Appl. No. 60/580,969, filed Jun. 17, 2004. Title: Combinations of Tumor-Associated Antigens in Diagnotistics for Various Types of Cancers.

U.S. Appl. No. 60/691,581, filed Jun. 17, 2005. Title: Multivalent Entrain- and-Amplify Immunotherapeutics for Carcinoma.

Bot, A., "Potent Immunity Achieved by Targeted Sequential Administration of Recombinant DN Vectors and Anchor-Modified Epitope Peptides," (Nov. 13, 2005) www.isbtc.org/meetings/am05/presentations/bot.pdf (retrieved 2006).

International Search Report and Written Opinion of the International Searching Authority dated Mar. 2, 2007 from International Application No. PCT/US2006/023499.

Issekutz et al., "Kinetics of cytotoxic lymphocytes in efferent lymph from single lymph nodes following immunization with vaccinia virus," Clin Exp Immunol 56: 515-523, 1984.

Lu, J. et al., "Multiepitope Trojan Antigen Peptide Vaccines for the Induction of Antitumor CTL and Th Immune Responses," J. Immunol., 172:4575-4582, 2004.

Spankuch-Schmitt, et al., "Downregulation of human polo-like kinase activity by antisense oligonucleotides induces growth inhibition in cancer cells," Oncogene. 21(20):3162-3171, 2002.

Zhong L, et al., "Recombinant adenovirus is an efficient and non-perturbing genetic vector for human dendritic cells," Eur J Immunol. 29(3):964-972, 1999.

* cited by examiner

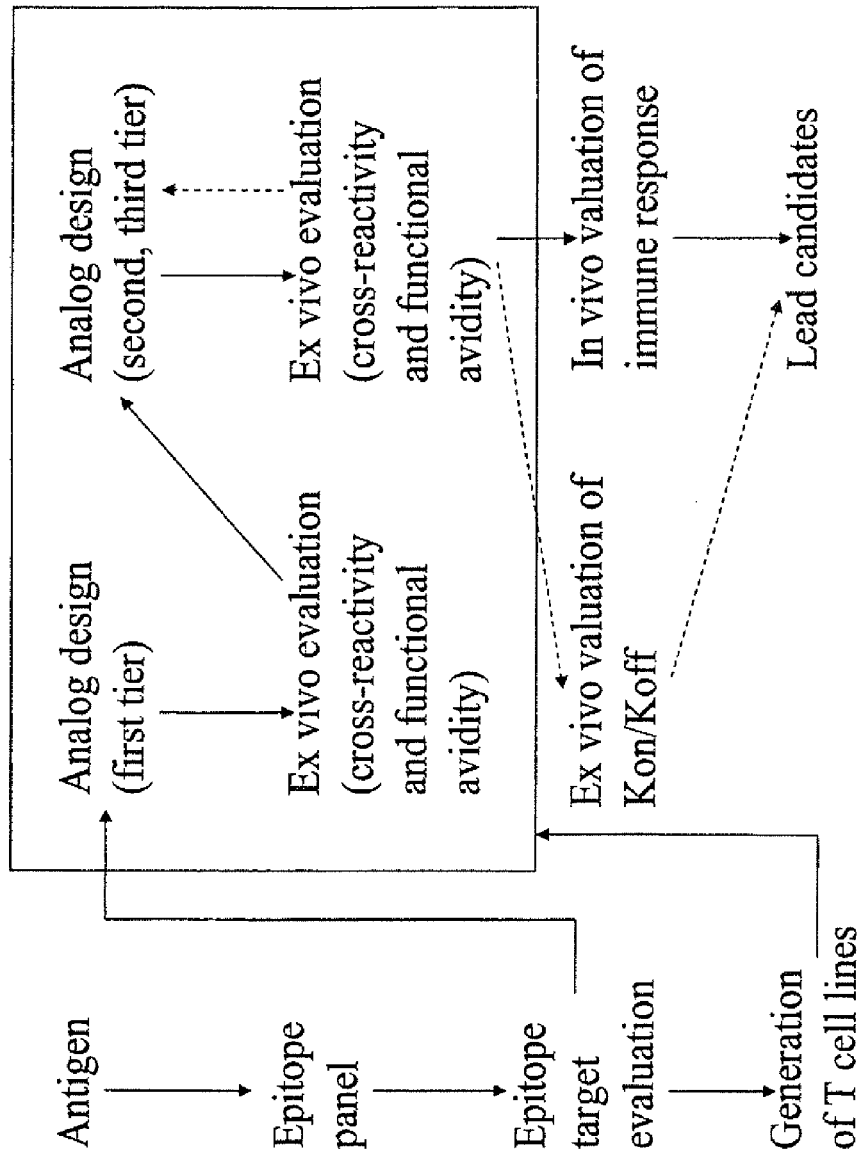
Fig. 11 : Methodology

Fig. 12 : Single substitution analogs of PSMA$_{288-297}$

| Category | No. | Peptide name | Sequence | % Binding | ED50 (M) | Stability (t1/2) (hr) | iScore | reactivity (IFN-γ) |
|---|---|---|---|---|---|---|---|---|
| Native | 1 | PSMA 288-297 | GLPSIPVHPI | 86.3 | 1.330E-06 | 5.341 | 0.693 | 27.29 |
| N-terminal primary anchor | 2 | PSMA 288-297 (L289M) | GMPSIPVHPI | 93.2 | 1.072E-06 | 3.340 | 0.605 | -4.99 |
| | 3 | PSMA 288-297 (L289I) | GIPSIPVHPI | 75.3 | 1.314E-06 | 0.346 | 0.159 | 4.39 |
| | 4 | PSMA 288-297 (L289Q) | GQPSIPVHPI | 84.9 | 6.687E-07 | 1.445 | 0.402 | -1.65 |
| | 5 | PSMA 288-297 (L289V) | GVPSIPVHPI | 69.9 | 2.414E-06 | 0.212 | 0.105 | 18.86 |
| | 6 | PSMA 288-297 (L289(Nva)) | G(Nva)PSIPVHPI | | | | | 15.28 |
| | 7 | PSMA 288-297 (L289(Nle)) | G(Nle)PSIPVHPI | 100.0 | 5.946E-07 | 4.342 | 0.81 | 5.36 |
| | 8 | PSMA 288-297 (L289(Abu)) | G(Abu)PSIPVHPI | 65.9 | 1.234E-06 | 0.591 | .189 | 13.85 |
| N-terminal secondary anchor | 9 | PSMA 288-297 (G288A) | ALPSIPVHPI | 74.4 | 9.805E-07 | 9.331 | 0.858 | 8.60 |
| | 10 | PSMA 288-297 (G288S) | SLPSIPVHPI | 67.7 | | 4.337 | 0 | 12.55 |
| | 11 | PSMA 288-297 (G288(Sar)) | (Sar)LPSIPVHPI | 90.4 | 6.851E-07 | 8.786 | 1.037 | 6.41 |
| | 12 | PSMA 288-297 (G288(Abu)) | (Abu)LPSIPVHPI | 101.4 | 4.083E-07 | 7.815 | 1.173 | 15.26 |
| C-terminal primary anchor | 13 | PSMA 288-297 (I297V) | GLPSIPVHPV | 98.6 | 8.344E-07 | 13.123 | 1.312 | 59.80 |
| | 14 | PSMA 288-297 (I297L) | GLPSIPVHPL | 83.6 | 1.166E-06 | 3.258 | 0.54 | 11.87 |
| | 15 | PSMA 288-297 (I297(Nva)) | GLPSIPVHP(Nva) | 92.4 | 1.221E-06 | 10.062 | 1.02 | 40.19 |
| | 16 | PSMA 288-297 (I297(Nle)) | GLPSIPVHP(Nle) | 97.3 | 8.525E-07 | 4.860 | 0.787 | 11.32 |
| C-terminal secondary anchor/TCR exploration | 17 | PSMA 288-297 (P296A) | GLPSIPVHAI | 90.4 | 8.160E-07 | 8.506 | 0.969 | 6.41 |
| | 18 | PSMA 288-297 (P296L) | GLPSIPVHLI | 86.3 | 5.859E-07 | 1.894 | 0.477 | 11.58 |
| | 19 | PSMA 288-297 (P296S) | GLPSIPVHSI | 83.6 | 4.468E-07 | 4.053 | 0.712 | 1.12 |
| | 20 | PSMA 288-297 (P296T) | GLPSIPVHTI | 82.2 | 4.829E-07 | 2.381 | 0.532 | 3.19 |
| TCR exploration/ secondary anchor | 21 | PSMA 288-297 (P290W) | GLWSIPVHPI | 102.7 | 7.770E-07 | 10.768 | 1.243 | 15.19 |

Fig. 13 : Double substitution analogs of $PSMA_{288-297}$

| Category | No. | Peptide name | Sequence | % Binding | ED50 (M) | Stability (t1/2) (hr) | IScore | reactivity (IFN-γ) |
|---|---|---|---|---|---|---|---|---|
| Native | 1 | PSMA 288-297 | GLPSIPVHPI | 88.3 | 1.330E-06 | 5.341 | 0.693 | 27.29 |
| N-terminal primary anchor and C-terminal primary | 22 | PSMA 288-297 (L289(Nva), I297(Nle)) | G(Nva)PSIPVHP(Nle) | 82.2 | 3.438E-07 | 1.044 | 0.374 | 5.37 |
| | 23 | PSMA 288-297 (L289(Nle), I297(Nva)) | G(Nle)PSIPVHP(Nva) | 86.3 | 5.443E-07 | 4.306 | 0.728 | 13.65 |
| | 24 | PSMA 288-297 (L289(Nva), I297(Nva)) | G(Nva)PSIPVHP(Nva) | 97.3 | 1.187E-06 | 6.356 | 0.849 | 10.81 |
| | 25 | PSMA 288-297 (L289(Nle), I297(Nle)) | G(Nle)PSIPVHP(Nle) | 100.0 | 5.243E-07 | 4.546 | 0.847 | 6.52 |
| | 26 | PSMA 288-297 (L289(Nva), I297V) | G(Nva)PSIPVHPV | 94.6 | 2.195E-06 | 13.685 | 1.094 | 58.32 |
| | 27 | PSMA 288-297 (L289(Nle), I297V) | G(Nle)PSIPVHPV | 92.4 | 2.271E-06 | 13.332 | 1.053 | 57.46 |
| | 28 | PSMA 288-297 (L289V, I297V) | GVPSIPVHPV | 78.3 | 3.323E-06 | 1.624 | 0.301 | 8.43 |
| | 29 | PSMA 288-297 (L289I, I297V) | GIPSIPVHPV | 84.3 | 1.146E-06 | 2.478 | 0.634 | 0.00 |
| | 30 | PSMA 288-297 (L289V, I297(Nva)) | GVPSIPVHP(Nva) | 96.6 | 8.238E-07 | 14.942 | 1.736 | |
| | 31 | PSMA 288-297 (L289I, I297(Nva)) | GIPSIPVHP(Nva) | 81.6 | 2.692E-07 | 2.585 | 0.502 | 0.00 |
| N-terminal secondary anchor and C-terminal primary anchor | 32 | PSMA 288-297 (G288A, I297V) | ALPSIPVHPV | 88.0 | 5.967E-06 | 14.157 | 0.882 | 72.33 |
| | 33 | PSMA 288-297 (G288A, I297(Nva)) | ALPSIPVHP(Nva) | 81.6 | 1.006E-06 | 10.320 | 0.924 | 46.11 |
| | 34 | PSMA 288-297 (G288(Abu), I297V) | (Abu)LPSIPVHPV | 85.1 | 7.888E-07 | 13.618 | 1.185 | 66.58 |
| | 35 | PSMA 288-297 (G288(Abu), I297(Nva)) | (Abu)LPSIPVHP(Nva) | 92.0 | 9.469E-07 | 10.894 | 1.141 | 58.01 |
| C-terminal primary anchor and TCR exploration | 36 | PSMA 288-297 (P290W, I297V) | GLWSIPVHPV | 89 | 1.244E-06 | 12.082 | 1.082 | 10.83 |
| | 37 | PSMA 288-297 (P290W, I297(Nva)) | GLWSIPVHP(Nva) | 102.2 | 8.329E-07 | 13.693 | 1.379 | 28.59 |
| N-terminal primary anchor and TCR exploration | 38 | PSMA 288-297 (L289(Nva), P290W) | G(Nva)WSIPVHPI | 101.1 | 1.411E-06 | 13.688 | 1.247 | 41.79 |
| | 39 | PSMA 288-297 (L289V, P290W) | GVWSIPVHPI | 83.7 | 2.184E-06 | 2.316 | 0.408 | 8.45 |
| | 40 | PSMA 288-297 (L289(Nle), P290W) | G(Nle)WSIPVHPI | 105.4 | 1.242E-06 | 10.527 | 1.156 | 21.2 |
| | 41 | PSMA 288-297 (L289I, P290W) | GIWSIPVHPI | 88.7 | 1.639E-07 | 9.687 | 1.202 | 0.00 |

Fig. 14    Triple substitution analogs of $PSMA_{288-297}$

| Category | No. | Peptide name | Sequence | % Binding | ED50 (M) | Stability (t1/2) (hr) | iScore | reactivity (IFN-γ) |
|---|---|---|---|---|---|---|---|---|
| Native | 1 | PSMA 288-297 | GLPSIPVHPI | 86.3 | 1.330E-06 | 5.341 | 0.693 | 27.29 |
| N-terminal primary/secondary anchor and TCR exploration | 42 | PSMA 288-297 (G288A, L289V(Nva), P290W) | A(Nva)WSIPVHPI | 96.6 | 1.307E-06 | 13.559 | 1.582 | 26.59 |
|  | 43 | PSMA 288-297 (G288A, L289V, P290W) | AVWSIPVHPI | 85.1 | 8.419E-07 | 4.526 | 0.652 | 6.25 |
|  | 44 | PSMA 288-297 (G288A, L289V(Nle), P290W) | A(Nle)WSIPVHPI | 108.7 | 2.464E-06 | 13.775 | 1.2 | 71.97 |
|  | 45 | PSMA 288-297 (G288A, L289L, P290W) | AIWSIPVHPI | 90.8 | 1.340E-07 | 5.124 | 0.841 | 0.00 |
| N-terminal primary/secondary anchor and C-terminal primary anchor | 46 | PSMA 288-297 (G288A, L289R(Nva), I297V) | A(Nva)PSIPVHPV | 85.9 |  1.264E-06 | 13.517 | 1.108 | 119.1 |
|  | 47 | PSMA 288-297 (G288A, L289V, I297V) | AVPSIPVHPV | 78.3 | 1.082E-06 | 2.755 | 0.477 | 16.06 |
|  | 48 | PSMA 288-297 (G288A, L289V, I297(Nva)) | AVPSIPVHP(Nva) | 98.9 | 2.854E-07 | 16.057 | 1.69 |  |
| N- and C-terminal primary anchor and TCR | 49 | PSMA 288-297 (L289(Nva), P290W, I297V) | G(Nva)WSIPVHPV | 102.2 | 1.372E-06 | 17.756 | 1.439 | 60.91 |
|  | 50 | PSMA 288-297 (L289V, P290W, I297V) | GVWSIPVHPV | 78 | 1.917E-06 | 9.552 | 0.803 | 0.00 |
|  | 51 | PSMA 288-297 (L289(Nva), P290W, I297(Nva)) | G(Nva)WSIPVHP(Nva) | 78.2 | 3.655E-07 | 0.707 | 0.239 | 0.00 |
|  | 52 | PSMA 288-297 (L289V, P290W, I297(Nva)) | GVWSIPVHP(Nva) | 92.4 | 2.747E-06 | 3.706 | 0.537 | 8.1 |
| N-terminal secondary, C-terminal primary anchor and TCR | 53 | PSMA 288-297 (G288A, P290W, I297V) | ALWSIPVHPV | 102.3 | 4.937E-07 | 13.530 | 1.672 | 6.19 |
|  | 54 | PSMA 288-297 (G288A, P290W, I297(Nva)) | ALWSIPVHP(Nva) | 106.5 | 4.332E-06 | 13.715 | 1.069 | 6.6 |

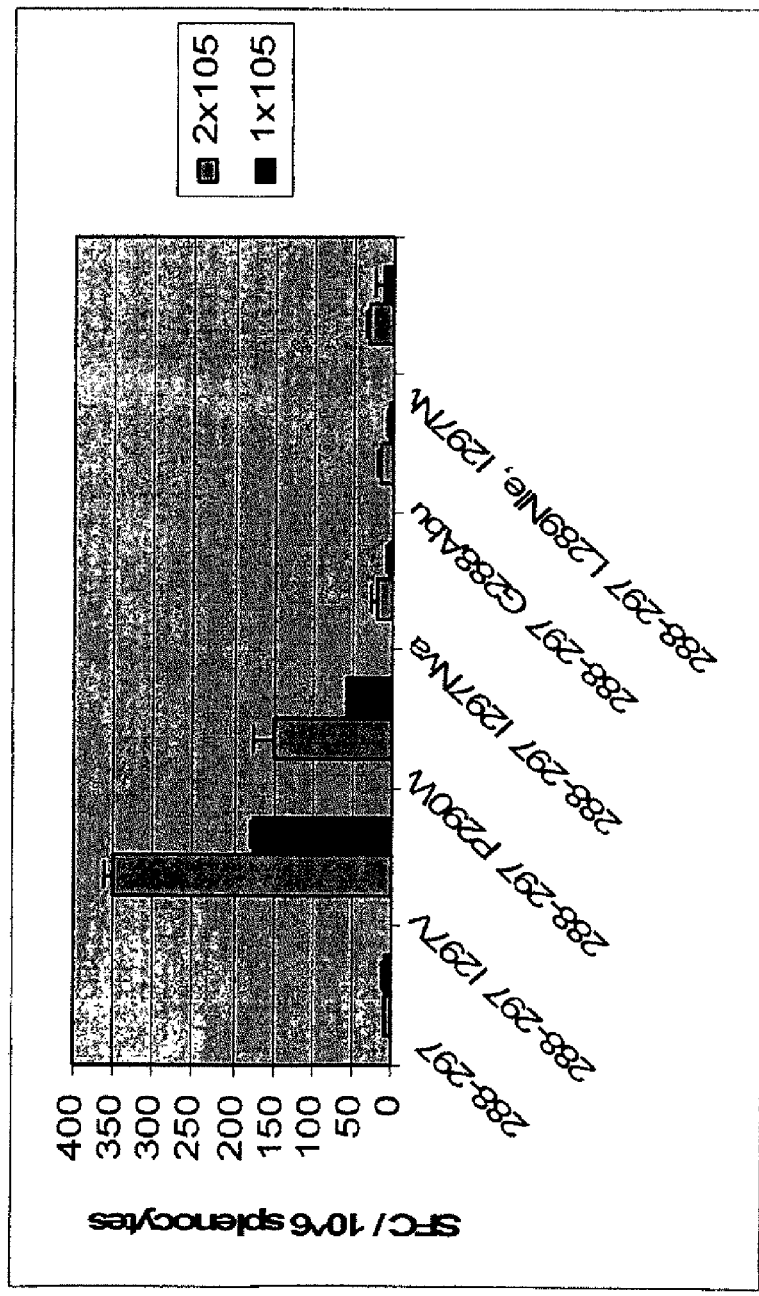
Fig. 15 : Immunogenicity of various PSMA$_{288-297}$ Analogs Measured by Elispot Fig. 16 Single substitution analogs of PRAME 425-433

| Category | No. | Peptide name | Sequence | % Binding (A0201) | Stability (t1/2) (hr) (A0201) | ED50 (mM) (A0201) | iScore (A0201) | Cross-reactivity as normalized IFN-gamma production |
|---|---|---|---|---|---|---|---|---|
| Native | 1 | Prame 425-433 | SLLQHLIGL | 81 | 12.2 | 7.158E-07 | 1.17 | 1.00 |
| N-terminal primary anchor | 2 | Prame 425-433 (L426V) | SVLQHLIGL | 66 | 7.1 | 6.179E-06 | 0.49 | 0.4 |
| | 3 | Prame 425-433 (L426M) | SMLQHLIGL | 100 | 10.3 | 9.884E-07 | 1.14 | 0.6 |
| | 4 | Prame 425-433 (L426I) | SILQHLIGL | 76 | 9.4 | 1.628E-06 | 0.80 | * |
| | 5 | Prame 425-433 (L426(Nle)) | S(Nle)LQHLIGL | 93 | 12.6 | 2.423E-06 | 1.01 | 0.56 |
| | 6 | Prame 425-433 (L426(Nva)) | S(Nva)LQHLIGL | 92 | 11.4 | 1.911E-06 | 1.00 | 0.8 |
| | 7 | Prame 425-433 (L426(Abu)) | S(Abu)LQHLIGL | 73 | 8.1 | 4.849E-06 | 0.59 | * |
| N-terminal secondary anchor | 8 | Prame 425-433 (S425K) | KLLQHLIGL | 82 | 10.8 | 4.412E-06 | 0.77 | 0.4 |
| | 9 | Prame 425-433 (S425F) | FLLQHLIGL | 110 | 17.7 | 4.335E-07 | 1.86 | 0.52 |
| | 10 | Prame 425-433 (S425Y) | YLLQHLIGL | 99 | 11.8 | 5.496E-07 | 1.34 | 0.8 |
| | 11 | Prame 425-433 (S425T) | TLLQHLIGL | 88 | 9.3 | 1.452E-06 | 0.82 | 0.81 |
| | 12 | Prame 425-433 (S425(Orn) (Orn is L-ornithine) | (Orn)LLQHLIGL | 89 | 10.0 | 2.252E-06 | 0.89 | 0.55 |
| | 13 | Prame 425-433 (S425(Hse)) (Hse is L-Homoserine) | (Hse)LLQHLIGL | 90 | 10.6 | 1.360E-06 | 1.01 | 0.65 |
| C-terminal primary anchor | 14 | Prame 425-433 (L433V) | SLLQHLIGV | 80 | 12.6 | 7.310E-06 | 0.74 | * |
| | 15 | Prame 425-433 (L433I) | SLLQHLIGI | 75 | 11.9 | 3.349E-06 | 0.79 | * |
| | 16 | Prame 425-433 (L433A) | SLLQHLIGA | 80 | 13.6 | 8.430E-06 | 0.85 | * |
| | 17 | Prame 425-433 (L433(Nle)) | SLLQHLIG(Nle) | 98 | 14.8 | 7.768E-07 | 1.40 | 0.72 |
| | 18 | Prame 425-433 (L433(Nva)) | SLLQHLIG(Nva) | 92 | 17.2 | 1.663E-06 | 1.25 | 0.52 |
| | 19 | Prame 425-433 (L433(Abu)) | SLLQHLIG(Abu) | 81 | 12.3 | 3.411E-06 | 0.85 | * |
| C-terminal amide | 20 | Prame 425-433-NH2 | SLLQHLIGL-NH2 | 89 | 3.0 | 1.384E-06 | 0.53 | 0.6 |
| TCR expiration | 21 | Prame 425-433 (G432A) | SLLQHLIAL | 88 | 12.4 | 1.729E-06 | 1.02 | * |
| | 22 | Prame 425-433 (G432S) | SLLQHLISL | 71 | 10.7 | 4.357E-06 | 0.69 | * |
| | 23 | Prame 425-433 (G432(Sar)) Sar is sarcosine | SLLQHLI(Sar)L | 74 | 9.2 | 2.368E-06 | 0.73 | * |
| | 24 | Prame 425-433 (L427(Nle)) | SL(Nle)QHLIGL | 81 | 12.3 | 2.493E-06 | 0.90 | * |
| | 25 | Prame 425-433 (L427(Nva)) | SL(Nva)QHLIGL | 78 | 11.7 | 3.153E-06 | 0.81 | 0.24 |
| | 26 | Prame 425-433 (L427(Abu)) | SL(Abu)QHLIGL | 74 | 10.1 | 9.258E-06 | 0.60 | * |
| | 27 | Prame 425-433 (L430(Nle)) | SLLQH(Nle)IGL | 81 | 11.2 | 4.740E-06 | 0.77 | * |
| | 28 | Prame 425-433 (L430(Nva)) | SLLQH(Nva)IGL | 74 | 11.4 | 7.265E-06 | 0.66 | 0.61 |
| | 29 | Prame 425-433 (L430(Abu)) | SLLQH(Abu)IGL | 76 | 10.6 | 5.140E-06 | 0.70 | 0.44 |

Fig. 17A : Double substitution analogs of PRAME 425-433

| Category | No. | Peptide name | Sequence | % Binding (A0201) | Stability (t1/2) (hr) (A0201) | ED50 (mM) (A0201) | iScore (A0201) | Cross-reactivity as normalized IFN-gamma production |
|---|---|---|---|---|---|---|---|---|
| Native | 1 | Prame 425-433 | SLLQHLIGL | 81 | 12.2 | 7.158E-07 | 1.17 | 1.00 |
| N-terminal primary/secondary anchor | 30 | Prame 425-433 (S425F, L426(Nva)) | F(Nva)LQHLIGL | 106 | 11.7 | 4.518E-07 | 1.46 | + |
| | 31 | Prame 425-433 (S425Y, L426(Nva)) | Y(Nva)LQHLIGL | 96 | 9.4 | 1.660E-06 | 0.97 | + |
| | 32 | Prame 425-433 (S425T, L426(Nva)) | T(Nva)LQHLIGL | 87 | 10.7 | 2.386E-06 | 0.92 | + |
| | 33 | Prame 425-433 (S425(Hse), L426(Nva)) | (Hse)(Nva)LQHLIGL | 90 | 13.6 | 1.449E-06 | 1.12 | + |
| | 34 | Prame 425-433 (S425(Orn), L426(Nva)) | (Orn)(Nva)LQHLIGL | 88 | 12.3 | 5.019E-06 | 0.85 | + |
| | 35 | Prame 425-433 (S425F, L426(Nle)) | F(Nle)LQHLIGL | 118 | 11.4 | 5.661E-07 | 1.52 | + |
| | 36 | Prame 425-433 (S425Y, L426(Nle)) | Y(Nle)LQHLIGL | 110 | 11.5 | 5.572E-07 | 1.44 | + |
| | 37 | Prame 425-433 (S425T, L426(Nle)) | T(Nle)LQHLIGL | 100 | 12.6 | 2.554E-06 | 1.07 | + |
| | 38 | Prame 425-433 (S425(Hse), L426(Nle)) | (Hse)(Nle)LQHLIGL | 81 | 10.9 | 2.546E-06 | 0.84 | + |
| | 39 | Prame 425-433 (S425(Orn), L426(Nle)) | (Orn)(Nle)LQHLIGL | 80 | 9.9 | 4.704E-06 | 0.83 | + |
| | 40 | Prame 425-433 (S425F, L426M) | FMLQHLIGL | 100 | 12.8 | 1.160E-06 | 1.24 | + |
| | 41 | Prame 425-433 (S425Y, L426M) | YMLQHLIGL | 109 | 11.7 | 2.861E-07 | 1.62 | + |
| | 42 | Prame 425-433 (S425T, L426M) | TMLQHLIGL | 83 | 9.2 | 2.011E-06 | 0.89 | + |
| | 43 | Prame 425-433 (S425(Hse), L426M) | (Hse)MLQHLIGL | 93 | 11.7 | 4.674E-06 | 0.88 | + |
| | 44 | Prame 425-433 (S425(Orn), L426M) | (Orn)MLQHLIGL | 86 | 10.5 | 2.951E-06 | 0.90 | + |
| | 45 | Prame 425-433 (S425F, L426I) | FILQHLIGL | 98 | 10.3 | 1.152E-07 | 1.63 | + |
| | 46 | Prame 425-433 (S425Y, L426I) | YILQHLIGL | 87 | 10.1 | 7.155E-07 | 1.07 | + |
| | 47 | Prame 425-433 (S425T, L426I) | TILQHLIGL | 75 | 8.1 | 3.321E-06 | 0.65 | + |
| | 48 | Prame 425-433 (S425(Hse), L426I) | (Hse)ILQHLIGL | 75 | 9.9 | 2.774E-06 | 0.72 | + |
| | 49 | Prame 425-433 (S425(Orn), L426I) | (Orn)ILQHLIGL | 84 | 8.8 | 1.952E-06 | 0.81 | + |

Fig. 17B : Double substitution analogs of PRAME 425-433

| Category | No. | Peptide name | Sequence | % Binding (A0201) | Stability (t1/2) (hr) (A0201) | ED50 (mM) (A0201) | iScore (A0201) | Cross-reactivity as normalized IFN-gamma production |
|---|---|---|---|---|---|---|---|---|
| Native | 1 | Prame 425-433 | SLLQHLIGL | 81 | 12.2 | 7.158E-07 | 1.17 | 1.00 |
| N-terminal primary anchor and C-terminal primary anchor | 50 | Prame 425-433 (L426(Nva),L433(Nva)) | S(Nva)LQHLIG(Nva) | 91 | 13.2 | 2.936E-06 | 0.99 | * |
| | 51 | Prame 425-433 (L426(Nva),L433(Nle)) | S(Nva)LQHLIG(Nle) | 93 | 13.7 | 8.475E-07 | 1.27 | 0.69 |
| | 52 | Prame 425-433 (L426(Nva),L433V) | S(Nva)LQHLIGV | 88 | 16.0 | 2.980E-06 | 1.06 | * |
| | 53 | Prame 425-433 (L426(Nle),L433(Nva)) | S(Nle)LQHLIG(Nva) | 90 | 12.5 | 1.125E-06 | 1.19 | * |
| | 54 | Prame 425-433 (L426(Nle),L433(Nle)) | S(Nle)LQHLIG(Nle) | 100 | 12.4 | 9.950E-07 | 1.25 | * |
| | 55 | Prame 425-433 (L426(Nle),L433V) | S(Nle)LQHLIGV | 93 | 13.9 | 2.461E-06 | 1.07 | * |
| | 56 | Prame 425-433 (L426M,L433(Nva)) | SMLQHLIG(Nva) | 99 | 13.4 | 6.878E-07 | 1.37 | * |
| | 57 | Prame 425-433 (L426M,L433(Nle)) | SMLQHLIG(Nle) | 104 | 11.2 | 6.148E-07 | 1.34 | * |
| | 58 | Prame 425-433 (L426M,L433V) | SMLQHLIGV | 97 | 15.5 | 9.401E-07 | 1.38 | * |
| N-terminal secondary anchor and C-terminal primary anchor | 59 | Prame 425-433 (S425K,L433V) | KLLQHLIGV | 77 | 14.2 | 9.038E-06 | 0.74 | * |
| | 60 | Prame 425-433 (S425F,L433V) | FLLQHLIGV | 110 | 16.3 | 7.180E-07 | 1.64 | * |
| | 61 | Prame 425-433 (S425Y,L433V) | YLLQHLIGV | 91 | 14.3 | 2.816E-06 | 1.19 | * |
| | 62 | Prame 425-433 (S425T,L433V) | TLLQHLIGV | 85 | 17.2 | 3.722E-06 | 1.02 | * |
| | 63 | Prame 425-433 (S425(Orn),L433V) | (Orn)LLQHLIGV | 79 | 12.9 | 2.740E-06 | 0.89 | * |
| | 64 | Prame 425-433 (S425(Hse),L433V) | (Hse)LLQHLIGV | 77 | 10.2 | 5.849E-06 | 0.67 | * |
| | 65 | Prame 425-433 (S425F,L433(Nle)) | FLLQHLIGNle | 88 | 23.3 | 1.538E-07 | 2.14 | 1.16 |
| | 66 | Prame 425-433 (S425T,L433(Nle)) | TLLQHLIGNle | 88 | 13.9 | 1.251E-06 | 1.15 | 0.75 |

Fig. 18 Triple substitution analogs of PRAME$_{425-433}$

| Category | No. | Peptide name | Sequence | % Binding | ED50 (M) | Stability (t1/2) (hr) | iScore | Cross-reactivity as normalized IFN-γ production |
|---|---|---|---|---|---|---|---|---|
| Native | 1 | Prame 425-433 | SLLQHLIGL | 81 | 7.158E-07 | 12.2 | 1.17 | 1.00 |
| N-terminal primary/secondary anchor and C-terminal primary anchor | 67 | Prame 425-433 (S425F, L426(Nva), L433(Nle)) | FNvaLQHLIGNle | 108 | 1.158E-07 | 25.3 | 2.78 | 0.82 |
| | 68 | Prame 425-433 (S425T, L426(Nva), L433(Nle)) | TNvaLLQHLIGNle | 118 | 2.844E-07 | 19.6 | 2.24 | 0.91 |
| | 69 | Prame 425-433 (S425F, L426M, L433(Nle)) | FMLQHLIGNle | 124 | 1.803E-07 | 13.1 | 2.05 | ND |
| | 70 | Prame 425-433 (S425T, L426M, L433(Nle)) | TMLQHLIGNle | 97 | 6.802E-07 | 13.5 | 1.36 | ND |

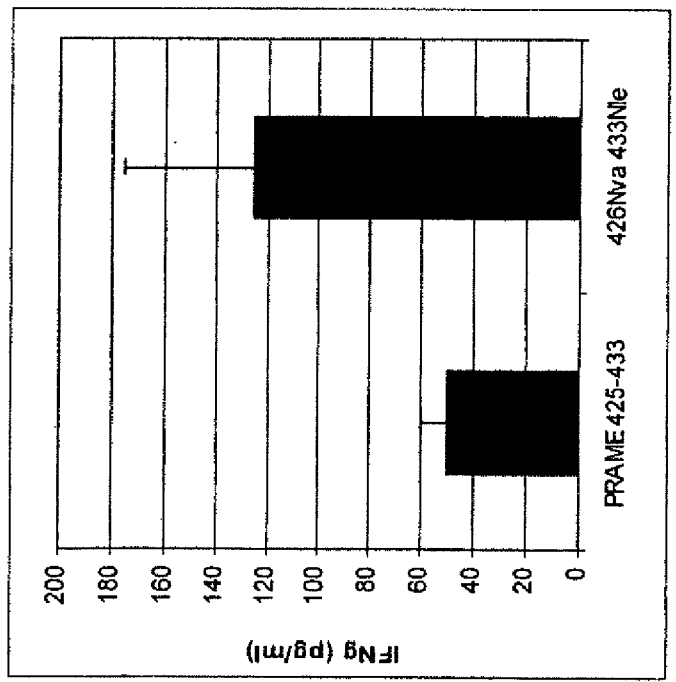
Fig. 19: Immunogenicity of a PRAME$_{425-433}$ Analog Measured by Elispot

SEQUENCE LISTING

<160> NUMBER OF SEQ ID NOS: 22

<210> SEQ ID NO 1
<211> LENGTH: 9
<212> TYPE: PRT
<213> ORGANISM: HOMO SAPIENS

<400> SEQUENCE: 1

Lys Ala Ser Glu Lys Ile Phe Tyr Val
1               5

<210> SEQ ID NO 2
<211> LENGTH: 9
<212> TYPE: PRT
<213> ORGANISM: HOMO SAPIENS

<400> SEQUENCE: 2

Ser Leu Leu Met Trp Ile Thr Gln Cys
1               5

<210> SEQ ID NO 3
<211> LENGTH: 9
<212> TYPE: PRT
<213> ORGANISM: Homo sapien

<400> SEQUENCE: 3

Ser Leu Leu Gln His Leu Ile Gly Leu
1               5

<210> SEQ ID NO 4
<211> LENGTH: 10
<212> TYPE: PRT
<213> ORGANISM: homo sapien

<400> SEQUENCE: 4

Gly Leu Pro Ser Ile Pro Val His Pro Ile
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Man made peptide

<400> SEQUENCE: 5

Lys Val Ser Glu Lys Ile Phe Tyr Val
1               5

<210> SEQ ID NO 6
<211> LENGTH: 9
<212> TYPE: PRT
<213> ORGANISM: Artificial Sequence
<220> FEATURE:
<223> OTHER INFORMATION: Analog of NY-ESO-1, amino acids 157-165
<220> FEATURE:
<221> NAME/KEY: VARIANT
<222> LOCATION: 2
<223> OTHER INFORMATION: Xaa = Norvaline

<400> SEQUENCE: 6

Ser Xaa Leu Met Trp Ile Thr Gln Val
1               5

<210> SEQ ID NO 7

```
<211> LENGTH: 9
<212> TYPE: PRT
<213> ORGANISM: Artificial Sequence
<220> FEATURE:
<223> OTHER INFORMATION: Analog of PRAME, amino acids 425-433
<220> FEATURE:
<221> NAME/KEY: VARIANT
<222> LOCATION: 2
<223> OTHER INFORMATION: Xaa = Norvaline
<220> FEATURE:
<221> NAME/KEY: VARIANT
<222> LOCATION: 9
<223> OTHER INFORMATION: Xaa = Norleucine

<400> SEQUENCE: 7

Ser Xaa Leu Gln His Leu Ile Gly Xaa
 1               5

<210> SEQ ID NO 8
<211> LENGTH: 10
<212> TYPE: PRT
<213> ORGANISM: Artificial Sequence
<220> FEATURE:
<223> OTHER INFORMATION: Man made peptide

<400> SEQUENCE: 8

Gly Leu Pro Ser Ile Pro Val His Pro Val
 1               5                  10

<210> SEQ ID NO 9
<211> LENGTH: 10
<212> TYPE: PRT
<213> ORGANISM: homo sapien

<400> SEQUENCE: 9

Glu Leu Ala Gly Ile Gly Ile Leu Thr Val
 1               5                  10

<210> SEQ ID NO 10
<211> LENGTH: 9
<212> TYPE: PRT
<213> ORGANISM: homo sapien

<400> SEQUENCE: 10

Tyr Met Asp Gly Thr Met Ser Gln Val
 1               5

<210> SEQ ID NO 11
<211> LENGTH: 10
<212> TYPE: PRT
<213> ORGANISM: Artificial Sequence
<220> FEATURE:
<223> OTHER INFORMATION: Analog of Melan-A, amino acids 26-35
<220> FEATURE:
<221> NAME/KEY: VARIANT
<222> LOCATION: 2
<223> OTHER INFORMATION: Xaa = Norvaline

<400> SEQUENCE: 11

Glu Xaa Ala Gly Ile Gly Ile Leu Thr Val
 1               5                  10

<210> SEQ ID NO 12
<211> LENGTH: 9
<212> TYPE: PRT
<213> ORGANISM: Artificial Sequence
<220> FEATURE:
<223> OTHER INFORMATION: Analog of tyrosinase, amino acids 369-377
<220> FEATURE:
<221> NAME/KEY: VARIANT
```

```
<222> LOCATION: 9
<223> OTHER INFORMATION: Xaa = Norvaline

<400> SEQUENCE: 12

Tyr Met Asp Gly Thr Met Ser Gln Xaa
 1               5

<210> SEQ ID NO 13
<211> LENGTH: 29
<212> TYPE: PRT
<213> ORGANISM: Artificial Sequence
<220> FEATURE:
<223> OTHER INFORMATION: Man made peptide

<400> SEQUENCE: 13

Ile Lys Ala Ser Glu Lys Ile Phe Tyr Val Ser Leu Leu Met Trp Ile
 1               5                  10                  15

Thr Gln Cys Lys Ala Ser Glu Lys Ile Phe Tyr Val Lys
            20                  25

<210> SEQ ID NO 14
<211> LENGTH: 62
<212> TYPE: PRT
<213> ORGANISM: Artificial Sequence
<220> FEATURE:
<223> OTHER INFORMATION: Man made peptide

<400> SEQUENCE: 14

Lys Arg Ser Leu Leu Gln His Leu Ile Gly Leu Gly Asp Ala Ala Tyr
 1               5                  10                  15

Ser Leu Leu Gln His Leu Ile Gly Leu Ile Ser Pro Glu Lys Glu Glu
            20                  25                  30

Gln Tyr Ile Ala Ser Leu Leu Gln His Leu Ile Gly Leu Lys Arg Pro
        35                  40                  45

Ser Ile Lys Arg Gly Leu Pro Ser Ile Pro Val His Pro Val
    50                  55                  60

<210> SEQ ID NO 15
<211> LENGTH: 28
<212> TYPE: PRT
<213> ORGANISM: Artificial Sequence
<220> FEATURE:
<223> OTHER INFORMATION: Man made peptide

<400> SEQUENCE: 15

Met Leu Leu Ala Val Leu Tyr Cys Leu Glu Ala Gly Ile Gly Ile
 1               5                  10                  15

Leu Thr Val Tyr Met Asp Gly Thr Met Ser Gln Val
            20                  25

<210> SEQ ID NO 16
<211> LENGTH: 179
<212> TYPE: PRT
<213> ORGANISM: Artificial Sequence
<220> FEATURE:
<223> OTHER INFORMATION: Man made peptide

<400> SEQUENCE: 16

Met Ser Leu Leu Met Trp Ile Thr Gln Cys Lys Ala Ser Glu Lys Ile
 1               5                  10                  15

Phe Tyr Val Gly Leu Pro Ser Ile Pro Val His Pro Ile Gly Leu Pro
            20                  25                  30

Ser Ile Pro Val His Pro Ile Lys Ala Ser Glu Lys Ile Phe Tyr Val
        35                  40                  45
```

Ser Leu Leu Met Trp Ile Thr Gln Cys Lys Ala Ser Glu Lys Ile Phe
 50                  55                  60

Tyr Val Lys Ala Ser Glu Lys Ile Phe Tyr Val Arg Cys Gly Ala Arg
 65                  70                  75                  80

Gly Pro Glu Ser Arg Leu Leu Glu Phe Tyr Leu Ala Met Pro Phe Ala
                 85                  90                  95

Thr Pro Met Glu Ala Glu Leu Ala Arg Arg Ser Leu Ala Gln Asp Ala
                100                 105                 110

Pro Pro Leu Pro Val Pro Gly Val Leu Leu Lys Glu Phe Thr Val Ser
                115                 120                 125

Gly Asn Ile Leu Thr Ile Arg Leu Thr Ala Ala Asp His Arg Gln Leu
130                 135                 140

Gln Leu Ser Ile Ser Ser Cys Leu Gln Gln Leu Ser Leu Leu Met Trp
145                 150                 155                 160

Ile Thr Gln Cys Phe Leu Pro Val Phe Leu Ala Gln Pro Pro Ser Gly
                165                 170                 175

Gln Arg Arg

<210> SEQ ID NO 17
<211> LENGTH: 275
<212> TYPE: PRT
<213> ORGANISM: Artificial Sequence
<220> FEATURE:
<223> OTHER INFORMATION: Man made peptide

<400> SEQUENCE: 17

Met Asn Leu Leu His Glu Thr Asp Ser Ala Val Ala Thr Ala Arg Arg
  1               5                  10                  15

Pro Arg Trp Leu Cys Ala Gly Ala Leu Val Leu Ala Gly Gly Phe Phe
                 20                  25                  30

Leu Leu Gly Phe Leu Phe Gly Trp Phe Ile Lys Ser Ala Gln Leu Ala
             35                  40                  45

Gly Ala Lys Gly Val Ile Leu Tyr Ser Asp Pro Ala Asp Tyr Phe Ala
 50                  55                  60

Pro Gly Val Lys Ser Tyr Pro Asp Gly Trp Asn Leu Pro Gly Gly Gly
 65                  70                  75                  80

Val Gln Arg Gly Asn Ile Leu Asn Leu Asn Gly Ala Gly Asp Pro Leu
                 85                  90                  95

Thr Pro Gly Tyr Pro Ala Asn Glu Tyr Ala Tyr Arg Arg Gly Ile Ala
                100                 105                 110

Glu Ala Val Gly Leu Pro Ser Ile Pro Val His Pro Ile Ala Leu Gln
                115                 120                 125

Ser Leu Leu Gln His Leu Ile Gly Leu Ser Asn Leu Thr His Val Leu
130                 135                 140

Tyr Pro Val Pro Leu Glu Ser Tyr Glu Asp Ile His Gly Thr Leu His
145                 150                 155                 160

Leu Glu Arg Leu Ala Tyr Leu His Ala Arg Leu Arg Glu Leu Leu Cys
                165                 170                 175

Glu Leu Gly Arg Pro Ser Met Val Trp Leu Ser Ala Asn Pro Cys Pro
                180                 185                 190

His Cys Gly Asp Arg Thr Phe Tyr Asp Pro Glu Pro Ile Leu Cys Pro
                195                 200                 205

Cys Phe Met Pro Asn Lys Arg Ser Leu Leu Gln His Leu Ile Gly Leu
210                 215                 220

Gly Asp Ala Ala Tyr Ser Leu Leu Gln His Leu Ile Gly Leu Ile Ser

```
                225                 230                 235                 240
Pro Glu Lys Glu Glu Gln Tyr Ile Ala Ser Leu Leu Gln His Leu Ile
                    245                 250                 255
Gly Leu Lys Arg Pro Ser Ile Lys Arg Gly Leu Pro Ser Ile Pro Val
                260                 265                 270
His Pro Val
        275

<210> SEQ ID NO 18
<211> LENGTH: 94
<212> TYPE: PRT
<213> ORGANISM: Artificial Sequence
<220> FEATURE:
<223> OTHER INFORMATION: Man made peptide

<400> SEQUENCE: 18

Met Leu Leu Ala Val Leu Tyr Cys Leu Glu Leu Ala Gly Ile Gly Ile
1               5                   10                  15

Leu Thr Val Tyr Met Asp Gly Thr Met Ser Gln Val Gly Ile Leu Thr
                20                  25                  30

Val Ile Leu Gly Val Leu Leu Ile Gly Cys Trp Tyr Cys Arg Arg
            35                  40                  45

Arg Asn Gly Tyr Arg Ala Leu Met Asp Lys Ser Leu His Val Gly Thr
        50                  55                  60

Gln Cys Ala Leu Thr Arg Arg Cys Pro Gln Glu Gly Phe Asp His Arg
65                  70                  75                  80

Asp Ser Lys Val Ser Leu Gln Glu Lys Asn Cys Glu Pro Val
                85                  90

<210> SEQ ID NO 19
<211> LENGTH: 3315
<212> TYPE: DNA
<213> ORGANISM: Artificial Sequence
<220> FEATURE:
<223> OTHER INFORMATION: Plasmid

<400> SEQUENCE: 19
```

| | | | | |
|---|---|---|---|---|
| atatacgcgt | tgacattgat | tattgactag | ttattaatag | taatcaatta cggggtcatt | 60 |
| agttcatagc | ccatatatgg | agttccgcgt | tacataactt | acggtaaatg gcccgcctgg | 120 |
| ctgaccgccc | aacgaccccc | gcccattgac | gtcaataatg | acgtatgttc ccatagtaac | 180 |
| gccaataggg | actttccatt | gacgtcaatg | ggtggagtat | ttacggtaaa ctgcccactt | 240 |
| ggcagtacat | caagtgtatc | atatgccaag | tacgccccct | attgacgtca atgacggtaa | 300 |
| atggcccgcc | tggcattatg | cccagtacat | gaccttatgg | gactttccta cttggcagta | 360 |
| catctacgta | ttagtcatcg | ctattaccat | ggtgatgcgg | ttttggcagt acatcaatgg | 420 |
| gcgtggatag | cggtttgact | cacggggatt | tccaagtctc | cacccccattg acgtcaatgg | 480 |
| gagtttgttt | tggcaccaaa | atcaacggga | ctttccaaaa | tgtcgtaaca actccgcccc | 540 |
| attgacgcaa | atgggcggta | ggcgtgtacg | gtgggaggtc | tatataagca gagctctctg | 600 |
| gctaactaga | gaacccactg | cttactggct | tatcgaaatt | aatacgactc actataggga | 660 |
| gacccaagct | ggctagcgtt | taaacttaag | ccaccatgtt | actagctgtt ttgtactgcc | 720 |
| tggaactagc | agggatcggc | atattgacag | tgtatatgga | tggaacaatg tcccaggtag | 780 |
| gaattctgac | agtgatcctg | ggagtcttac | tgctcatcgg | ctgttggtat tgtagaagac | 840 |
| gaaatggata | cagagcctttg | atggataaaa | gtcttcatgt | tggcactcaa tgtgccttaa | 900 |
| caagaagatg | cccacaagaa | gggtttgatc | atcgggacag | caaagtgtct cttcaagaga | 960 |

```
aaaactgtga acctgtgtag tgagcggccg ctcgagtcta agggccccgt ttaaacccgc   1020
tgatcagcct cgactgtgcc ttctagttgc cagccatctg ttgtttgccc ctcccccgtg   1080
ccttccttga ccctggaagg tgccactccc actgtccttt cctaataaaa tgaggaaatt   1140
gcatcgcatt gtctgagtag gtgtcattct attctggggg gtggggtggg caggacagc    1200 aaggggagg attgggaaga caatagcagg catgctgggg atgcggtggg ctctatggct    1260
tctactgggc ggttttatgg acagcaagcg aaccggaatt gccagctggg gcgccctctg   1320
gtaaggttgg gaagccctgc aaagtaaact ggatggcttt cttgccgcca aggatctgat   1380
ggcgcagggg atcaagctct gatcaagaga caggatgagg atcgtttcgc atgattgaac   1440
aagatggatt gcacgcaggt tctccggccg cttgggtgga gaggctattc ggctatgact   1500
gggcacaaca gacaatcggc tgctctgatg ccgccgtgtt ccggctgtca gcgcagggc    1560 gcccggttct ttttgtcaag accgacctgt ccggtgccct gaatgaactg caagacgagg   1620
cagcgcggct atcgtggctg gccacgacgg gcgttccttg cgcagctgtg ctcgacgttg   1680
tcactgaagc gggaagggac tggctgctat tgggcgaagt gccggggcag gatctcctgt   1740
catctcacct tgctcctgcc gagaaagtat ccatcatggc tgatgcaatg cggcggctgc   1800
atacgcttga tccggctacc tgcccattcg accaccaagc gaaacatcgc atcgagcgag   1860
cacgtactcg gatggaagcc ggtcttgtcg atcaggatga tctggacgaa gagcatcagg   1920
ggctcgcgcc agccgaactg ttcgccaggc tcaaggcgag catgcccgac ggcgaggatc   1980
tcgtcgtgac ccatggcgat gcctgcttgc cgaatatcat ggtggaaaat ggccgctttt   2040
ctggattcat cgactgtggc cggctgggtg tggcggaccg ctatcaggac atagcgttgg   2100
ctacccgtga tattgctgaa gagcttggcg gcgaatgggc tgaccgcttc ctcgtgcttt   2160
acggtatcgc cgctcccgat tcgcagcgca tcgccttcta tcgccttctt gacgagttct   2220
tctgaattat taacgcttac aatttcctga tgcggtattt tctccttacg catctgtgcg   2280
gtatttcaca ccgcatcagg tggcactttt cggggaaatg tgcgcggaac cctatttgt    2340 ttatttttct aaatacattc aaatatgtat ccgctcatga caataaccc tgataaatg     2400 cttcaataat agcacgtgct aaaacttcat ttttaattta aaaggatcta ggtgaagatc   2460 cttttttgata atctccggaa gagtcaagaa catgtgagca aaaggccagc aaaaggccag   2520
gaaccgtaaa aaggccgcgt tgctggcgtt tttccatagg ctccgccccc ctgacgagca   2580
tcacaaaaat cgacgctcaa gtcagaggtg gcgaaacccg acaggactat aaagatacca   2640
ggcgtttccc cctggaagct ccctcgtgcg ctctcctgtt ccgaccctgc cgcttaccgg   2700
atacctgtcc gcctttctcc cttcgggaag cgtggcgctt tctcatagct cacgctgtag   2760
gtatctcagt tcggtgtagg tcgttcgctc caagctgggc tgtgtgcacg aaccccccgt   2820
tcagcccgac cgctgcgcct tatccggtaa ctatcgtctt gagtccaacc cggtaagaca   2880
cgacttatcg ccactggcag cagccactgg taacaggatt agcagagcga ggtatgtagg   2940
cggtgctaca gagttcttga agtggtggcc taactacggc tacactagaa gaacagtatt   3000
tggtatctgc gctctgctga agccagttac cttcggaaaa agagttggta gctcttgatc   3060
cggcaaacaa accaccgctg gtagcggtgg tttttttgtt tgcaagcagc agattacgcg   3120
cagaaaaaaa ggatctcaag aagatccttt gatcttttct acggggtctg acgctcagtg   3180
gaacgaaaac tcacgttaag ggattttggt ccgccggaa acgtttggtt gctgactaat    3240
tgagatgcat gctttgcata cttctgcctg ctggggagcc tggggacttt ccacacctcg   3300
cgatgtacgg gccag                                                     3315
```

<210> SEQ ID NO 20
<211> LENGTH: 3596
<212> TYPE: DNA
<213> ORGANISM: Artificial Sequence
<220> FEATURE:
<223> OTHER INFORMATION: Plasmid

<400> SEQUENCE: 20

| | | | | | |
|---|---|---|---|---|---|
| gttgacattg | attattgact | agttattaat | agtaatcaat | tacggggtca | ttagttcata | 60 |
| gcccatatat | ggagttccgc | gttacataac | ttacggtaaa | tggcccgcct | ggctgaccgc | 120 |
| ccaacgaccc | ccgcccattg | acgtcaataa | tgacgtatgt | tcccatagta | acgccaatag | 180 |
| ggactttcca | ttgacgtcaa | tgggtggagt | atttacggta | aactgcccac | ttggcagtac | 240 |
| atcaagtgta | tcatatgcca | agtacgcccc | ctattgacgt | caatgacggt | aaatggcccg | 300 |
| cctggcatta | tgcccagtac | atgaccttat | gggactttcc | tacttggcag | tacatctacg | 360 |
| tattagtcat | cgctattacc | atggtgatgc | ggttttggca | gtacatcaat | gggcgtggat | 420 |
| agcggtttga | ctcacgggga | tttccaagtc | tccaccccat | tgacgtcaat | gggagtttgt | 480 |
| tttggcacca | aaatcaacgg | gactttccaa | aatgtcgtaa | caactccgcc | ccattgacgc | 540 |
| aaatgggcgg | taggcgtgta | cggtgggagg | tctatataag | cagagctctc | tggctaacta | 600 |
| gagaacccac | tgcttactgg | cttatcgaaa | ttaatacgac | tcactatagg | gagacccaag | 660 |
| ctggctagcg | tttaaactta | agccaccatg | tccctgttga | tgtggatcac | gcagtgcaaa | 720 |
| gcttcggaga | aaatcttcta | tgtgggtctt | ccaagtattc | ctgttcatcc | aattggtctt | 780 |
| ccaagtattc | ctgttcatcc | aattaaagct | tcggagaaaa | tcttctatgt | gtccctgttg | 840 |
| atgtggatca | cgcagtgcaa | agcttcggag | aaaatcttct | atgtgaaagc | ttcggagaaa | 900 |
| atcttctacg | tacggtgcgg | tgccaggggg | ccggagagcc | gcctgcttga | gttctacctc | 960 |
| gccatgcctt | tcgcgacacc | catggaagca | gagctggccc | gcaggagcct | ggcccaggat | 1020 |
| gccccaccgc | ttcccgtgcc | aggggtgctt | ctgaaggagt | tcactgtgtc | cggcaacata | 1080 |
| ctgactatcc | gactgactgc | tgcagaccac | cgccaactgc | agctctccat | cagctcctgt | 1140 |
| ctccagcagc | tttccctgtt | gatgtggatc | acgcagtgct | ttctgcccgt | gttttggct | 1200 |
| cagcctccct | cagggcagag | gcgctagtga | gaattctgca | gatatccatc | acactggcgg | 1260 |
| ccgctcgagt | ctagagggcc | cgtttaaacc | cgctgatcag | cctcgactgt | gccttctagt | 1320 |
| tgccagccat | ctgttgtttg | cccctccccc | gtgccttcct | tgaccctgga | aggtgccact | 1380 |
| cccactgtcc | tttcctaata | aaatgaggaa | attgcatcgc | attgtctgag | taggtgtcat | 1440 |
| tctattctgg | ggggtggggt | ggggcaggac | agcaagggg | aggattggga | agacaatagc | 1500 |
| aggcatgctg | gggatgcggt | gggctctatg | gcttctactg | ggcggtttta | tggacagcaa | 1560 |
| gcgaaccgga | attgccagct | ggggcgccct | ctggtaaggt | tgggaagccc | tgcaaagtaa | 1620 |
| actggatggc | tttcttgccg | ccaaggatct | gatggcgcag | gggatcaagc | tctgatcaag | 1680 |
| agacaggatg | aggatcgttt | cgcatgattg | aacaagatgg | attgcacgca | ggttctccgg | 1740 |
| ccgcttgggt | ggagaggcta | ttcggctatg | actgggcaca | acagacaatc | ggctgctctg | 1800 |
| atgccgccgt | gttccggctg | tcagcgcagg | ggcgcccggt | tctttttgtc | aagaccgacc | 1860 |
| tgtccggtgc | cctgaatgaa | ctgcaagacg | aggcagcgcg | gctatcgtgg | ctggccacga | 1920 |
| cgggcgttcc | ttgcgcagct | gtgctcgacg | ttgtcactga | agcgggaagg | gactggctgc | 1980 |
| tattgggcga | agtgccgggg | caggatctcc | tgtcatctca | ccttgctcct | gccgagaaag | 2040 |
| tatccatcat | ggctgatgca | atgcggcggc | tgcatacgct | tgatccggct | acctgcccat | 2100 |

```
tcgaccacca agcgaaacat cgcatcgagc gagcacgtac tcggatggaa gccggtcttg    2160
tcgatcagga tgatctggac gaagagcatc aggggctcgc gccagccgaa ctgttcgcca    2220
ggctcaaggc gagcatgccc gacggcgagg atctcgtcgt gacccatggc gatgcctgct    2280
tgccgaatat catggtggaa aatggccgct tttctggatt catcgactgt ggccggctgg    2340
gtgtggcgga ccgctatcag gacatagcgt tggctacccg tgatattgct gaagagcttg    2400
gcggcgaatg ggctgaccgc ttcctcgtgc tttacggtat cgccgctccc gattcgcagc    2460
gcatcgcctt ctatcgcctt cttgacgagt tcttctgaat tattaacgct tacaatttcc    2520
tgatgcggta ttttctcctt acgcatctgt gcggtatttc acaccgcatc aggtggcact    2580
tttcggggaa atgtgcgcgg aaccccctat tgtttatttt tctaaataca ttcaaatatg    2640
tatccgctca tgagacaata accctgataa atgcttcaat aatagcacgt gctaaaactt    2700 cattttttaat ttaaaaggat ctaggtgaag atcctttttg ataatctccg gaagagtcaa    2760
gaacatgtga gcaaaaggcc agcaaaaggc caggaaccgt aaaaaggccg cgttgctggc    2820 gttttttccat aggctccgcc cccctgacga gcatcacaaa aatcgacgct caagtcagag    2880
gtggcgaaac ccgacaggac tataaagata ccaggcgttt ccccctggaa gctccctcgt    2940
gcgctctcct gttccgaccc tgccgcttac cggatacctg tccgcctttc tcccttcggg    3000
aagcgtggcg ctttctcata gctcacgctg taggtatctc agttcggtgt aggtcgttcg    3060
ctccaagctg ggctgtgtgc acgaacccc c gttcagccc gaccgctgcg ccttatccgg    3120
taactatcgt cttgagtcca acccggtaag acacgactta tcgccactgg cagcagccac    3180
tggtaacagg attagcagag cgaggtatgt aggcggtgct acagagttct tgaagtggtg    3240
gcctaactac ggctacacta agaacagt atttggtatc tgcgctctgc tgaagccagt    3300
taccttcgga aaaagagttg gtagctcttg atccggcaaa caaaccaccg ctggtagcgg    3360 tggtttttttt gtttgcaagc agcagattac gcgcagaaaa aaaggatctc aagaagatcc    3420
tttgatcttt tctacggggt ctgacgctca gtggaacgaa aactcacgtt aagggatttt    3480
ggtccggccg gaaacgtttg gttgctgact aattgagatg catgctttgc atacttctgc    3540
ctgctgggga gcctggggac tttccacacc tcgcgatgta cgggccagat atacgc       3596
```

<210> SEQ ID NO 21
<211> LENGTH: 3884
<212> TYPE: DNA
<213> ORGANISM: Artificial Sequence
<220> FEATURE:
<223> OTHER INFORMATION: Plasmid

<400> SEQUENCE: 21

```
cgttgacatt gattattgac tagttattaa tagtaatcaa ttacggggtc attagttcat      60
agcccatata tggagttccg cgttacataa cttacggtaa atggcccgcc tggctgaccg     120
cccaacgacc cccgcccatt gacgtcaata atgacgtatg ttcccatagt aacgccaata     180
gggactttcc attgacgtca atgggtggag tatttacggt aaactgccca cttggcagta     240
catcaagtgt atcatatgcc aagtacgccc cctattgacg tcaatgacgg taaatggccc     300
gcctggcatt atgcccagta catgacctta tgggactttc ctacttggca gtacatctac     360
gtattagtca tcgctattac catggtgatg cggttttggc agtacatcaa tgggcgtgga     420
tagcggtttg actcacgggg atttccaagt ctccacccca ttgacgtcaa tgggagtttg     480
ttttggcacc aaaatcaacg ggactttcca aaatgtcgta acaactccgc cccattgacg     540
caaatgggcg gtaggcgtgt acggtgggag gtctatataa gcagagctct ctggctaact     600
```

```
agagaaccca ctgcttactg gcttatcgaa attaatacga ctcactatag ggagacccaa    660
gctggctagc gtttaaactt aagccaccat gaatctcctt cacgaaaccg actcggctgt    720
ggccaccgcg cgccgcccgc gctggctgtg cgctggggcg ctggtgctgg cgggtggctt    780
ctttctcctc ggcttcctct tcgggtggtt tataaaaagc gctcagctgg caggggccaa    840
aggagtcatt ctctactccg accctgctga ctactttgct cctggggtga agtcctatcc    900
agatggttgg aatcttcctg gaggtggtgt ccagcgtgga aatatcctaa atctgaatgg    960
tgcaggagac cctctcacac caggttaccc agcaaatgaa tatgcttata ggcgtggaat   1020
tgcagaggct gttggtcttc caagtattcc tgttcatcct attgccctgc agagtctctt   1080
gcagcacctc atcgggctga gcaatctgac ccacgtgctg tatcctgtcc ccctggagag   1140
ttatgaggac atccatggta ccctccacct ggagaggctt gcctatctgc atgccaggct   1200
cagggagttg ctgtgtgagt tggggcggcc cagcatggtc tggcttagtg ccaaccctg    1260 tcctcactgt ggggacagaa ccttctatga cccggagccc atcctgtgcc cctgtttcat   1320
gcctaacaag cgatcgctcc tgcaacacct catcgggctg ggggacgccg cctacagtct   1380
cctgcaacac ctcatcgggc tgatttcccc ggagaaggaa gagcagtata tcgccagtct   1440
cctgcaacac ctcatcgggc tgaagaggcc aagtattaag aggggtcttc caagtattcc   1500
tgttcatcca gttagtgag aattctgcag atatccatca cactggcggc cgctcgagtc    1560
tagagggccc gtttaaaccc gctgatcagc ctcgactgtg ccttctagtt gccagccatc   1620
tgttgtttgc cctcccccg tgccttcctt gaccctggaa ggtgccactc ccactgtcct    1680
ttcctaataa aatgaggaaa ttgcatcgca ttgtctgagt aggtgtcatt ctattctggg   1740
gggtggggtg gggcaggaca gcaaggggga ggattgggaa gacaatagca ggcatgctgg   1800
ggatgcggtg ggctctatgg cttctactgg gcggttttat ggacagcaag cgaaccggaa   1860
ttgccagctg gggcgccctc tggtaaggtt gggaagccct gcaaagtaaa ctggatggct   1920
ttcttgccgc caaggatctg atggcgcagg ggatcaagct ctgatcaaga gacaggatga   1980
ggatcgtttc gcatgattga acaagatgga ttgcacgcag gttctccggc cgcttgggtg   2040
gagaggctat tcggctatga ctgggcacaa cagacaatcg gctgctctga tgccgccgtg   2100
ttccggctgt cagcgcaggg gcgcccggtt ctttttgtca agaccgacct gtccggtgcc   2160
ctgaatgaac tgcaagacga ggcagcgcgg ctatcgtggc tggccacgac gggcgttcct   2220
tgcgcagctg tgctcgacgt tgtcactgaa gcgggaaggg actggctgct attgggcgaa   2280
gtgccggggc aggatctcct gtcatctcac cttgctcctg ccgagaaagt atccatcatg   2340
gctgatgcaa tgcggcggct gcatacgctt gatccggcta cctgcccatt cgaccaccaa   2400
gcgaaacatc gcatcgagcg agcacgtact cggatggaag ccggtcttgt cgatcaggat   2460
gatctggacg aagagcatca ggggctcgcg ccagccgaac tgttcgccag gctcaaggcg   2520
agcatgcccg acggcgagga tctcgtcgtg acccatggcg atgcctgctt gccgaatatc   2580
atggtggaaa atggccgctt ttctggattc atcgactgtg gccggctggg tgtggcggac   2640
cgctatcagg acatagcgtt ggctacccgt gatattgctg aagagcttgg cggcgaatgg   2700
gctgaccgct tcctcgtgct ttacggtatc gccgctcccg attcgcagcg catcgccttc   2760
tatcgccttc ttgacgagtt cttctgaatt attaacgctt acaatttcct gatgcggtat   2820
tttctcctta cgcatctgtg cggtatttca caccgcatca ggtggcactt ttcggggaaa   2880
tgtgcgcgga acccctattt gtttattttt ctaaatacat tcaaatatgt atccgctcat   2940
gagacaataa ccctgataaa tgcttcaata atagcacgtg ctaaaacttc attttttaatt  3000
```

```
taaaaggatc taggtgaaga tccttttga taatctccgg aagagtcaag aacatgtgag    3060
caaaaggcca gcaaaaggcc aggaaccgta aaaaggccgc gttgctggcg ttttccata    3120 ggctccgccc ccctgacgag catcacaaaa atcgacgctc aagtcagagg tggcgaaacc    3180
cgacaggact ataaagatac caggcgtttc ccctggaag  ctccctcgtg cgctctcctg    3240
ttccgaccct gccgcttacc ggatacctgt ccgcctttct ccttcggga  agcgtggcgc    3300 tttctcatag ctcacgctgt aggtatctca gttcggtgta ggtcgttcgc tccaagctgg    3360
gctgtgtgca cgaaccccc  gttcagcccg accgctgcgc cttatccggt aactatcgtc    3420
ttgagtccaa cccggtaaga cacgacttat cgccactggc agcagccact ggtaacagga    3480
ttagcagagc gaggtatgta ggcggtgcta cagagttctt gaagtggtgg cctaactacg    3540
gctacactag aagaacagta tttggtatct gcgctctgct gaagccagtt accttcggaa    3600
aaagagttgg tagctcttga tccggcaaac aaaccaccgc tggtagcggt ggttttttg    3660 tttgcaagca gcagattacg cgcagaaaaa aaggatctca agaagatcct ttgatctttt    3720
ctacggggtc tgacgctcag tggaacgaaa actcacgtta agggattttg gtccggccgg    3780
aaacgtttgg ttgctgacta attgagatgc atgctttgca tacttctgcc tgctggggag    3840
cctggggact ttccacacct cgcgatgtac gggccagata tacg                    3884

<210> SEQ ID NO 22
<211> LENGTH: 9
<212> TYPE: PRT
<213> ORGANISM: homo sapien

<400> SEQUENCE: 22

Glu Ala Ala Gly Ile Gly Leu Thr Val
 1               5
```

MULTIVALENT ENTRAIN-AND-AMPLIFY IMMUNOTHERAPEUTICS FOR CARCINOMA

The present application claims the benefit of the filing date of U.S. Provisional Patent Application Ser. No. 60/691,581, filed on Jun. 17, 2005, the entire text of which is incorporated herein by reference without disclaimer.

BACKGROUND OF THE INVENTION

1. Field of the Invention

The invention disclosed herein relates to methods and compositions for inducing an MHC class-I restricted immune response, controlling the nature and magnitude of the response, particularly a multivalent response, and promoting effective immunologic intervention in pathogenic processes. Disclosed herein are methods and compositions for inducing an immune response against various combinations of tumor-associated antigens, which can promote effective immunologic intervention in pathogenic processes.

2. Description of the Related Art

The American Cancer Society has estimated that over one million people get cancer each year, and that approximately one out of every two American men and one out of every three American women will have some type of cancer at some point during their lifetime.

Normal body cells grow, divide, and die in an orderly fashion. In cell proliferative diseases such as cancer, cells, instead of dying, continue to grow out of control and divide. Although there are many kinds of cancer, they usually start because of out-of-control growth of abnormal cells.

Usual treatment options for cancer include surgery, radiation therapy, and chemotherapy. A fourth branch of treatment, which is referred to as immunotherapy, has more recently become established. Immunotherapies are designed to help the immune system recognize cancer cells, and/or to strengthen a response against cancer cells in order to destroy the cancer. Immunotherapies include active and passive immunotherapies. Active immuotherapies attempt to stimulate the body's own immune system to fight the disease. Passive immunotherapies generally do not rely on the patient's immune system to attack the disease; instead, they use immune system components (such as antibodies) created outside of the patient's body.

The immune system can be categorized into two discrete effector arms, innate and adaptive immunity. Innate immunity involves numerous cellular components and soluble factors that respond immediately, but generally to foreign stimuli. Adaptive immunity is customized to respond specifically to precise epitopes from foreign agents. The adaptive immune response is further divided into two effector arms known as the humoral and cellular immune systems. The humoral arm is centered on the production of antibodies by B-lymphocytes while the cellular arm involves the cytolytic activity of cytotoxic T lymphocytes.

Cytotoxic T lymphocytes (CTL) do not recognize epitopes on the targeted antigens themselves. Rather, CTL detect fragments of antigens that are displayed on the surface of cells. As a result antigens are visible to CTL only after they have been processed by the cell and displayed on the surface of the cell. The antigen processing and display system of cells has been well established. CTL recognize short peptide antigens, which are displayed on the surface in non-covalent association with class I major histocompatibility complex molecules (MHC). These class I peptides are in turn derived from the degradation of cytosolic proteins.

Despite various types of cancer treatments, a continuing need exists for additional and more effective treatment alternatives. One such alternative envisions methodologies of medical treatment that require or benefit from an ability to initiate, stimulate, and/or enhance an immune response by immunization. These methodologies include those depending upon the creation of an immune response against a desired antigenic polypeptide and those that depend upon the initiation or modulation of an innate immune response. Thus one approach in the treatment of cancer is the manipulation of the immune system by use of a therapeutic anticancer vaccine.

To generate a vaccine or other immunogenic composition, an antigen or epitope against which an immune response can be mounted is introduced into a subject. Although neoplastic cancer cells are derived from and therefore are substantially identical to normal cells on a genetic level, many neoplastic cells are known to present tumor-associated antigens (TuAAs). These antigens can be used by a subject's immune system to recognize and attack the neoplastic cells as foreign. Unfortunately, neoplastic cells generally appear to be ignored by the host's immune system.

A number of different strategies have been developed in the art in an attempt to generate vaccines with activity against neoplastic cells; however, an effective and marketable product has not emerged. The present invention therefore serves to overcome the deficiencies in the art and provides a plurality of immunogenic compositions, disclosed herein, for targeting cancer or tumor cells.

SUMMARY OF THE INVENTION

The present invention relates to methods and compositions for inducing, entraining, and/or amplifying the immune response to MHC class-I restricted epitopes of carcinoma antigens to generate an effective anti-cancer immune response.

Embodiments of the disclosed invention are directed to the use of combinations of tumor-associated antigens (TuAAs) for the immunotherapy of patients with various types of cancer. In preferred embodiments, the TuAAs are antigens expressed by the cancer cell itself. Examples of such TuAAs are Melan-A, tyrosinase, SSX-2, NY-ESO-1, and PRAME. In alternate embodiments, the TuAAs are antigens associated with non-cancerous components of the tumor, such as tumor-associated neovasculature or other stroma. An example of such an antigen is PSMA—though, in prostate cancer PSMA is expressed by cancerous cells. In particularly preferred embodiments both types of antigen are targeted. Different aspects of the invention include the immunogenic compositions, their collection into defined products, and methods for their use.

Some specific embodiments relate to an immunogenic product comprising a plurality of compositions comprising one or more nucleic acid compositions and one or more peptide compositions; wherein the one or more nucleic acid compositions are capable of expressing one or more class I MHC restricted epitopes, or an analog thereof, selected from the group consisting of an SSX-1 epitope, an NY-ESO-1 epitope, a PRAME epitope, a PSMA epitope, a tyrosinase epitope, and a Melan-A epitope; wherein the one or more peptide compositions consist essentially of said one or more class I MHC restricted epitopes, or an analog thereof, selected from the group consisting of an SSX-1 epitope, an NY-ESO-1 epitope, a PRAME epitope, a PSMA epitope, a tyrosinase epitope, and a Melan-A epitope; and wherein the one or more peptides correspond to the epitopes expressed by the selected nucleic acids.

In some embodiments of the immunogenic product the one or more nucleic acid compositions comprise a plasmid selected from the group consisting of pSEM, pBPL and pRP12. In some embodiments the peptide compositions comprise a peptide selected from the group consisting of SSX-$2_{41-49}$ (SEQ ID NO. 1), its analogue KVSEKIFYV (SEQ ID NO. 5); NY-ESO-$1_{157-165}$ (SEQ ID NO. 2), its analogue SNvaLMWITQV (SEQ ID NO. 6); PRAME$_{425-433}$ (SEQ ID NO. 3), its analogue S(Nva)LQHLIG(Nle) (SEQ ID NO. 7); PSMA$_{288-297}$ (SEQ ID NO. 4), its analogue GLPSIPVHPV (SEQ ID NO. 8); Melan-A$_{26-35}$ (SEQ ID NO. 22), the A27L analogue of Melan-A$_{26-35}$ (SEQ ID NO. 9), the Melan-A$_{26-35}$ analogue ENvaAGIGILTV (SEQ ID NO. 11); tyrosinase$_{369-377}$ (SEQ ID NO. 10), and its analogue yMdgtmsqNva (SEQ ID NO. 12). In some embodiments the plurality of compositions comprise: a nucleic acid molecule capable of expressing an SSX-2 class I MHC restricted epitope, or analogue thereof; a nucleic acid molecule capable of expressing an NY-ESO-1 class 1 MHC restricted epitope, or analogue thereof; a nucleic acid molecule capable of expressing a PRAME class I MHC restricted epitope, or analogue thereof; a nucleic acid molecule capable of expressing a PSMA class I MHC restricted epitope, or analogue thereof; a peptide consisting essentially of said SSX-2 epitope, or analogue thereof; a peptide consisting essentially of said NY-ESO-1 epitope, or analogue thereof; a peptide consisting essentially of said PRAME epitope, or analogue thereof; and a peptide consisting essentially of said PSMA epitope, or analogue thereof.

In some embodiments of the immunogenic product the included nucleic acid molecules are part of the same composition. In some embodiments the nucleic acid molecules are the same. In some embodiments the nucleic acid molecule comprises a sequence encoding the liberation sequence of pBPL (SEQ ID NO. 13). In some embodiments the nucleic acid comprises a sequence encoding the immunogenic polypeptide of pBPL (SEQ ID NO. 16). In some embodiments the nucleic acid molecule is pBPL (SEQ ID NO. 20). In some embodiments the nucleic acid molecule comprises a sequence encoding the liberation sequence of pRP12 (SEQ ID NO. 14). In some embodiments the nucleic acid comprises a sequence encoding the immunogenic polypeptide of pRP12 (SEQ ID NO. 17). In some embodiments the nucleic acid molecule is pRP12 (SEQ ID. 21). In some embodiments the SSX-2 epitope is SSX-$_{241-49}$ (SEQ ID NO. 1). In some embodiments the NY-ESO-1 epitope is NY-ESO-$1_{157-165}$ (SEQ ID NO. 2). In some embodiments the PRAME epitope is PRAME$_{425-433}$ (SEQ ID NO. 3). In some embodiments the PSMA epitope is PSMA$_{288-297}$ (SEQ ID NO. 4). In some embodiments the SSX-2 analogue is KVSEKIFYV (SEQ ID NO. 5). In some embodiments the NY-ESO-1 analogue is SNvaLMWITQV (SEQ ID NO. 6). In some embodiments the PRAME analogue in is S(Nva)LQHLIG(Nle) (SEQ ID NO. 7). In some embodiments the PSMA analogue in is GLPSIPVHPV (SEQ ID NO. 8).

In some embodiments of the immunogenic product the plurality of compositions comprise: a nucleic acid molecule capable of expressing a Melan-A class I MHC restricted epitope, or analogue thereof; a nucleic acid molecule capable of expressing a Tyrosinase class I MHC restricted epitope, or analogue thereof; a peptide consisting essentially of said Melan-A epitope, or analogue thereof; and a peptide consisting essentially of said Tyrosinase epitope, or analogue thereof. In some embodiments the nucleic acid molecules are part of the same composition. In some embodiments the nucleic acid molecules are the same. In some embodiments the nucleic acid molecule comprises a sequence encoding the liberation sequence of pSEM (SEQ ID NO. 15). In some embodiments the nucleic acid comprises a sequence encoding the immunogenic polypeptide of pSEM (SEQ ID NO. 18). In some embodiments the nucleic acid molecule is pSEM (SEQ ID NO. 19). In some embodiments the Melan-A epitope is the A27L analogue of Melan-A$_{26-35}$ (SEQ ID NO. 9). In some embodiments the Tyrosinase epitope is Tyrosinase$_{369-377}$ (SEQ ID NO. 10). In some embodiments the immunogenic product further comprises: a nucleic acid molecule capable of expressing an SSX-2 class I MHC restricted epitope, or analogue thereof; and a nucleic acid molecule capable of expressing an NY-ESO-1 class I MHC restricted epitope, or analogue thereof. In some embodiments the immunogenic product also comprises a peptide consisting essentially of an NY-ESO-1 epitope. In some embodiments the immunogenic product also comprises a peptide consisting essentially of an SSX-2 epitope.

Embodiments of the current invention relate to compositions and methods for entraining and amplifying a T cell response. Such methods include an entraining step where a composition comprising a nucleic acid encoded immunogen is delivered to an animal. The composition can be delivered to various locations on the animal, but preferably the composition is delivered to the lymphatic system (for example to a lymph node). The entrainment step can include one or more deliveries of that composition, for example, spread out over a period of time or in a continuous fashion over a period of time. The methods can further include an amplification step comprising administering a composition comprising a peptide immunogen such as SSX-$2_{41-49}$ (SEQ ID NO. 1), NY-ESO-$1_{157-165}$ (SEQ ID NO. 2), PRAME$_{425-433}$ (SEQ ID NO. 3), PSMA$_{288-297}$ (SEQ ID NO. 4), the A27L analogue of Melan-A$_{26-35}$ (SEQ ID NO. 9), Tyrosinase$_{369-377}$ (SEQ ID NO. 10), and analogues thereof (as represented by SEQ. ID NOS. 5, 6, 7, 8, 11, and 12) having substantial similarity to the corresponding TuAA epitopes encoded by the nucleic acid composition. The amplification step can be performed one or more, times, for example, at intervals over a period of time, in one bolus, or continuously over a period of time. Although not required in all embodiments, some embodiments can include the use of compositions that include an immunopotentiator or adjuvant.

Further embodiments include those in which the disclosed plasmids are used individually or in any combination. The peptide compositions corresponding to these epitopes and part of the amplification portion of the immunization strategy can be native sequences or peptide analogues substantially similar to the native epitope sequence. The peptides can be incorporated into the amplification protocol individually or in combinations of 2, 3, 4, or more of the immunogens.

Still other embodiments can include alternate epitopes (such as those described in the U.S. patent application Ser. No. 10/117,937, entitled "Epitope Sequences," filed on Apr. 4, 2002 (Publication No. 20030220239 A1), which is hereby expressly incorporated by reference) substituted in similar combination as the epitopes expressed in the pSEM (SEQ ID NO. 19), pBPL (SEQ ID NO. 20), and pRP12 (SEQ ID NO. 21) plasmids and corresponding peptide immunogens administered as the amplification portion of the immunization strategy.

Embodiments of the invention can encompass, for example, two monovalent plasmids expressing single immunogens in place of one bivalent plasmid expressing both immunogens; a trivalent plasmid expressing three immunogens in place of one bivalent and one monovalent plasmid; a trivalent plasmid and one monovalent plasmid in place of a tetravalent plasmid; or two bivalent plasmids in place of a tetravalent plasmid. Embodiments can also encompass the use of the various plasmid combinations as part of the entrain step of the entrain-and-amplify immunization strategy.

Embodiments of the inventions can encompass a polypeptide or otherwise conjugated peptide that can be cleaved into individual peptides in the lymph and its use in the amplification step of the entrain-and-amplify immunization strategy.

Embodiments of the current invention relate to methods of immunization that include administering a series of immunogenic doses directly into the lymphatic system of a mammal wherein the series can include at least 1 entraining dose and at least 1 amplifying dose, and wherein the entraining dose can include a nucleic acid encoding an immunogen and wherein the amplifying dose can be free of any virus, viral vector, or replication-competent vector. The methods can further include obtaining an antigen-specific immune response. The methods can include, in a non-limiting example, 1-2 entraining doses. The method can include administering a plurality of entraining doses, wherein said doses are administered over a course of one to about 7 days. The entraining doses, amplifying doses, or entraining and amplifying doses can be delivered in multiple pairs of injections, wherein a first member of a pair can be administered within about 4 days of a second member of the pair, and wherein an interval between first members of different pairs can be at least about 14 days. An interval between a last entraining dose and a first amplifying dose can be between about 7 and about 100 days, for example, but is not limited to such.

Other embodiments relate to a method of treating carcinoma comprising a step of administering to a patient in need thereof a plurality of compositions including a nucleic acid molecule capable of expressing an SSX-2 class I MHC restricted epitope, or analogue thereof; a nucleic acid molecule capable of expressing an NY-ESO-1 class I MHC restricted epitope, or analogue thereof; a nucleic acid molecule capable of expressing a PRAME class I MHC restricted epitope, or analogue thereof; and a nucleic acid molecule capable of expressing a PSMA class I MHC restricted epitope, or analogue thereof. Another embodiment relates to the above-method further comprising a step of administering one or more peptides selected from the group epitopes or analogues consisting essentially of SSX-2, NY-ESO-1, PRAME, and PSMA.

A method of treating cancer comprising administering an immunogenic product comprising a plurality of compositions comprising one or more nucleic acid compositions and one or more peptide compositions; wherein the one or more nucleic acid compositions are capable of expressing one or more class I MHC restricted epitopes, or an analog thereof, selected from the group consisting of an SSX-1 epitope, an NY-ESO-1 epitope, a PRAME epitope, a PSMA epitope, a tyrosinase epitope, and a Melan-A epitope; wherein the one or more peptide compositions consist essentially of said one or more class I MHC restricted epitopes, or an analog thereof, selected from the group consisting of an SSX-1 epitope, an NY-ESO-1 epitope, a PRAME epitope, a PSMA epitope, a tyrosinase epitope, and a Melan-A epitope; and wherein the one or more peptides correspond to the epitopes expressed by the selected nucleic acids. Some embodiments relate to the use of the above method wherein the cancer is a breast cancer, an ovarian cancer, a pancreatic cancer, a prostate cancer, a colon cancer, a bladder cancer, a lung cancer, a liver cancer, a stomach cancer, a testicular cancer, an uterine cancer, a brain cancer, a lymphatic cancer, a skin cancer, a bone cancer, a kidney cancer, a rectal cancer, a melanoma, a glioblastoma, or a sarcoma.

Still other embodiments relate to a method of treating cancer comprising a step of administering to a patient in need thereof a plurality of compositions comprising: a nucleic acid molecule capable of expressing a Melan-A class I MHC restricted epitope, or analogue thereof; a nucleic acid molecule capable of expressing a Tyrosinase class I MHC restricted epitope, or analogue thereof; a peptide consisting essentially of said Melan-A epitope, or analogue thereof; and a peptide consisting essentially of said Tyrosinase epitope, or analogue thereof. Other embodiments relate to the use of the method where the cancer to be treated to is glioblastoma or melanoma. Yet other embodiments include a further step of administering to a patient in need thereof a composition comprising: a nucleic acid molecule capable of expressing an SSX-2 class I MHC restricted epitope, or analogue thereof; and a nucleic acid molecule capable of expressing an NY-ESO-1 class I MHC restricted epitope, or analogue thereof; a peptide consisting essentially of said NY-ESO-1 epitope or analogue thereof; and a peptide consisting essentially of said SSX-2 epitope or analogue thereof.

Other embodiments relate to sets of immunogenic compositions for inducing an immune response in a mammal including, in a non-limiting manner, 1-6 entraining doses and at least one amplifying dose. In such embodiments, the entraining doses can include a nucleic acid encoding an immunogen, and wherein the amplifying dose can include a peptide epitope, and wherein the epitope can be presented by a pAPC expressing the nucleic acid. The one dose further can include an adjuvant, for example, RNA. The entraining and amplifying doses can be in a carrier suitable for direct administration to the lymphatic system, (e.g., a lymph node and the like). The nucleic acid can be a plasmid. The epitope can be a class I HLA epitope. The immunogen can include an epitope array, which array can include a liberation sequence. The immunogen can consist essentially of a target-associated antigen. The target-associated antigen can be a tumor-associated antigen but is not limited to such. The immunogen can include a fragment of a target-associated antigen that can include an epitope cluster.

Further embodiments relate to the method of use of the entrain-and-amplify therapeutic compositions, tetravalent, bivalent, and/or monovalent plasmids and corresponding peptide immunogens, in the treatment of carcinoma, including melanoma, comprising administration via lymph node injection (i.e., directly into the organs where the immune responses are initiated and amplified) according to an optimized immunization schedule.

Yet further embodiments related to the manufacture of medicaments comprising the compositions of the invention. One embodiment relates to the manufacture of a medicament suitable for administration to the lymphatic system of a subject. Another embodiment relates to the manufacture of a medicament suitable for inducing an anti-cancer immune response in a subject. Another embodiment relates to the manufacture of a medicament that entrains and amplifies a T cell response in a subject. Another embodiment relates to the manufacture of a medicament suitable for treating carcinoma in a subject. Another embodiment relates to the use of one or more nucleic acid compositions capable of expressing one or more class I MHC restricted epitopes, or an analog thereof, and one or more peptide compositions corresponding to the said class I MHC restricted epitopes or analogues thereof, in the manufacture of a medicament suitable for inducing an anti-cancer immune response in a subject.

BRIEF DESCRIPTION OF THE DRAWINGS

FIG. 4A. IFN-γ ELISpot analysis was performed in triplicate, values represent average+/−Stdev. Peptide stimulating concentration was at 10 μg/ml and incubated for 42 hrs. FIG. 4B.— IFN-γ ELISpot analysis following the second peptide boost. ELISPOT analysis was performed by sacrificing representative animals on day 63. Group 1 animals (n=3 sacrificed) received injections of a mixture of pBPL+pSEM on Days 1, 4, 15, 18, 28, 32, 49, and 53 (100 μg/day). Group 2 animals (n=4 sacrificed) received injections of a mixture of pBPL+pSEM on days 1, 4, 15, and 18 (100 μg/day) followed by a peptide boost consisting of SSX-2$_{41-49}$ A42V (SEQ ID. NO. 5) in the left lymph node and Tyrosinase$_{369-377}$ V377Nva (SEQ ID. NO. 12) in the right lymph node on days 28, 32, 49, and 53 (25 μg/day). Group 3 animals (n=7 sacrificed) received injections of a mixture of pBPL+pSEM on days 1, 4, 15, and 18 (100 μg/day) in bilateral inguinal lymph nodes followed by a peptide boost consisting of SSX-2$_{41-49}$ A42V (SEQ ID. NO. 5) in the left lymph node and Tyrosinase$_{369-377}$ V377Nva (SEQ ID. NO. 12) in the right lymph node on days 28 and 32 (25 μg/day) and a second peptide boost consisting of NY-ESO-1$_{157-165}$ L158Nva (SEQ ID. NO. 6), C165V (12.5 μg on days 49 and 53) in the left lymph node and Melan A$_{76-35}$ A27Nva (SEQ ID. NO. 11) (25 μg on days 49 and 53) in the right lymph node. Antigen specific (Melan A, Tyrosinase, SSX-2, and NY-ESO-1) interferon-γ spot forming cells per spleen were compared to a untreated naïve littermate control (FIG. 4B). IFN-γ ELISpot analysis was performed in triplicate, values represent average+/−SEM. Peptide stimulating concentration was at 10 μg/ml and incubated for 42 hrs.

FIG. 9 depicts CTL response to PRAME$_{425-433}$ (SEQ ID. NO. 3), PSMA$_{283-797}$ (SEQ ID. NO. 4), NY-ESO-1$_{157-165}$ (SEQ ID. NO. 2) and SSX-2$_{41-49}$ (SEQ ID. NO. 1) after DNA prime and peptide boost and one round of in vitro stimulation in immunized mice. Data are presented as follows: the x-axis shows the effector to target ratio; the y-axis shows the corresponding percentage specific lysis.

FIG. 11 is a schematic diagram of the methodology of a preferred embodiment for identifying analogs.

FIG. 12 is a table showing the cross-reactivity and functional avidity of $PSMA_{288-297}$ analogs substituted at a single position.

FIG. 13 is a table showing the cross-reactivity and functional avidity of $PSMA_{288-297}$ analogs substituted at two positions.

FIG. 14 is a table showing the cross-reactivity and functional avidity of $PSMA_{288-297}$ analogs substituted at more than two positions.

FIG. 15 is a bar graph showing the immunogenicity of various $PSMA_{288-297}$ analogs measured by Elispot.

FIG. 16 is a table showing the cross-reactivity and functional avidity of $PRAME_{425-433}$ analogs substituted at a single position.

FIGS. 17A and 17B are tables showing the cross-reactivity and functional avidity of $PRAME_{425-433}$ analogs substituted at two positions.

FIG. 18 is a table showing the cross-reactivity and functional avidity of $PRAME_{425-433}$ analogs substituted at more than two positions.

FIG. 19 is a bar graph showing the immunogenicity of a $PRAME_{425-433}$ analog measured by Elispot.

DETAILED DESCRIPTION OF THE PREFERRED EMBODIMENT

Figure 1:
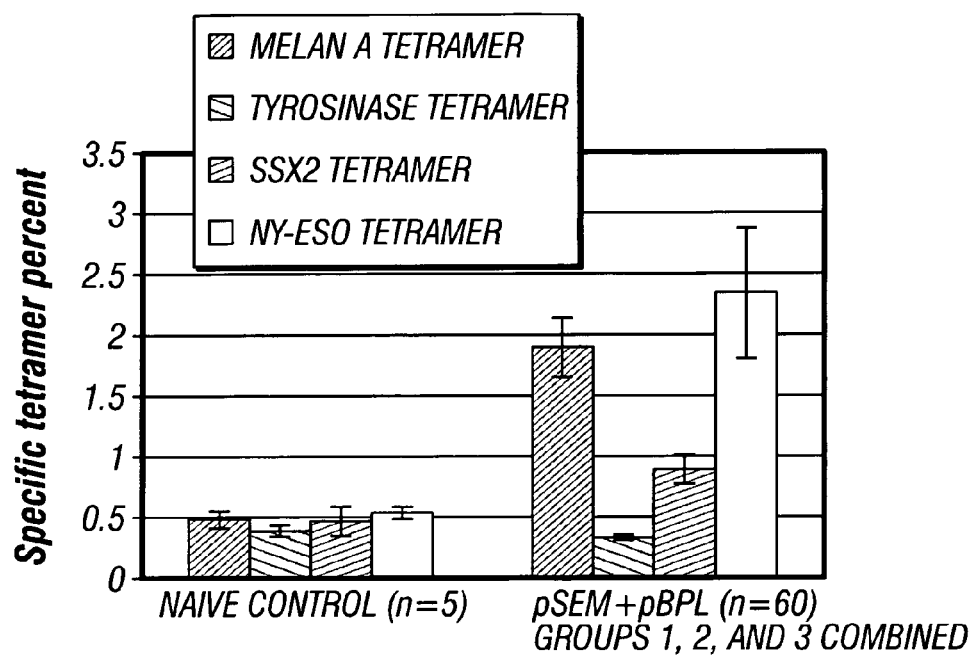
FIG. 1. Tetramer analysis of pSEM/pBPL, primed animals prior to peptide boost. Group 1, 2, and 3 animals (n=60) were primed with four injections of the pSEM/pBPL plasmid mixture on days 1, 4, 15, and 18 (100 μg/day) in bilateral inguinal lymph nodes. Tetramer analysis was performed on day 25, 10 days following the final plasmid injection and compared to untreated naïve littermate controls (n=5). Tetramer values (Melan A, Tyrosinase, SSX-2, NY-ESO-1) represent the average+/−SEM.

Embodiments of the present invention are based upon the induction of active immunity (therapeutic vaccination) preferably co-targeted against multiple molecules expressed by cancer cells and by the underlying neovasculature. This approach preferably involves targeted delivery of both recombinant DNA (plasmid) and synthetic peptides directly into the lymph nodes, thereby eliciting a strong cell-mediated immune response with the potential to ultimately interfere with the survival and/or viability of tumor cells within primary and metastatic lesions.

The methodology of the present invention includes the combined use of recombinant DNA plasmid and synthetic peptides, preferably administered using a prime (plasmid)/boost (peptide) approach via lymph node injection according to an optimized immunization schedule. In preferred embodiments, the lymph node injection is directly into the organism where the immune responses are initiated and amplified. Embodiments of the current invention can be administered to patients with tumor tissue that express HLA-A2, particularly HLA-A*0201. It has been observed that by using this immunization protocol that not only can the plasmid initiate an immune response, it biases the response and its subsequent amplification toward an effector as opposed to a regulatory character. Without this prior nucleic acid-based immunization, the repeated administration of peptide leads to a response ever more dominated by regulatory T cells. The long-lived bias toward an effector response is termed entrainment.

The disclosed embodiments relating to entrain-and-amplify therapeutics for carcinoma and melanoma can be used to achieve a multivalent attack, offering the advantage of increasing the sensitivity of the tumor to attack. If more than a single antigen on a tumor cell is targeted, the effective concentration of antitumor agent is increased accordingly. Attack on stroma associated with the tumor, such as vasculature, can also increase the accessibility of the tumor cells to the agent(s) targeting them. Thus, even an antigen that is also expressed on some normal tissue can receive greater consideration as a target antigen if the other antigens to be targeted in a multivalent attack are not also expressed by that tissue.

Practice of such immunization protocols involving disparate forms of immunogen requires use of at least two different compositions and, especially when there is more than a single target antigen, can involve several compositions to be administered together and/or at different times. Thus, embodiments of the invention include sets and subsets of immunogenic compositions and individual doses thereof. Multivalency can be achieved using compositions comprising multivalent immunogens, combinations of monovalent immunogens, coordinated use of compositions comprising one or more monovalent immunogens or various combinations thereof. Multiple compositions, manufactured for use in a particular treatment regimen or protocol according to such methods, define an immunotherapeutic product.

In some embodiments all or a subset of the compositions of the product are packaged together in a kit. In some instances, the inducing and amplifying compositions targeting a single epitope, or set of epitopes, can be packaged together. In other instances, multiple inducing compositions can be assembled in one kit and the corresponding amplifying compositions assembled in another kit. Alternatively, compositions may be packaged and sold individually along with instructions, in printed form or on machine-readable media, describing how they can be used in conjunction with each other to achieve the beneficial results of the indicated immunization protocol. Further variations will be apparent to one of skill in the art. The use of various packaging schemes comprising less than all of the compositions that might be employed in a particular protocol or regimen facilitates the personalization of the treatment, for example, based on tumor antigen expression, or observed response to the immunotherapeutic or its various components, as described in U.S. Provisional Application Ser. No. 60/580,969, filed on Jun. 17, 2004; U.S. patent application Ser. No. 11/155,288 (Publication No 20060008468) filed Jun. 17, 2005, and U.S. patent application Ser. No. 11/323,964 filed Dec. 29, 2005, all entitled "COMBINATIONS OF TUMOR-ASSOCIATED ANTIGENS IN DIAGNOSTICS FOR VARIOUS TYPES OF CANCERS"; and U.S. Provisional Patent Application Ser. No. 60/580,964, and U.S. patent application Ser. No. 11/155,928 (Publication No. 20050287068), both entitled "IMPROVED EFFICACY OF ACTIVE IMMUNOTHERAPY BY INTEGRATING DIAGNOSTIC WITH THERAPEUTIC METHODS", each of which is hereby incorporated by reference in its entirety.

Embodiments of the current invention encompass peptides incorporated into the amplification protocol individually or in combinations of 2, 3, 4, or more of the immunogens. Reasons for using less than all peptide epitopes include but are not limited to the following: 1) sub-optimal expression of any of the antigens; 2) the patient does not express, or no longer expresses, the corresponding antigen; 3) a less robust response is being generated to one or another of the epitopes, in which case such peptide(s) can be given in the absence of the others in order to obtain a more balanced response; 4) and a peptide can be discontinued if it is generating some sort of immunotoxicity.

I. Therapeutic Peptides and Plasmids of the Present Invention

A. Therapeutic Peptides and Analogues Thereof

The present invention contemplates the use of multiple molecules expressed by cancer cells and by the neovasculature as therapeutics in the treatment of cancer. Such molecules include tumor-associated antigens (TuAAs) which are antigens expressed by the cancer cell itself or associated with non-cancerous components of the tumor, such as tumor-associated neovasculature or other stroma. TuAAs help to match a patient's cancer condition or type with an appropriate immunotherapeutic agent or regimen. Non-limiting examples of TuAAs contemplated in the present invention include SSX-2, NY-ESO-1, PRAME, PSMA (prostate-specific membrane antigen), Melan-A, and tyrosinase. Therefore, in particular embodiments of the present invention, there is provided peptides, peptide analogues or epitopes of TuAAs (Table 1) as cancer therapeutics. In alternate embodiments of the present invention, the peptides can comprise the native sequence or be analogues of NY-ESO-1, SSX-2, Melan-A, tyrosinase, PRAME and PSMA, such as those disclosed in U.S. Provisional Application Ser. Nos. 60/581,001, 60/580,962, and 60/691,889 and their corresponding patent application Ser. Nos. 11/156,253 (Publication No. 20060063913), 11/155,929, (Publication No. 20060094661), 11/156,369 (Publication No. 20060057673), 11/455,278 (Publication No. 20070060524), filed on the same date as the present application Ser. No. 11/454,633 (Publication No. 20070049533), filed on the same date as the present application and 11/454,300 (Publication No. 20070060518), filed on the same date as the present application); and U.S. patent application Ser. Nos. 11/156,369 (Publication No. 20060057673) and 11/156,253 (Publication No. 20060063913); each of which is hereby incorporated by reference in its entirety.

Tyrosinase, a melanin biosynthetic enzyme, is predominantly expressed in melanocytes with high levels often observed in melanomas. Therefore, tyrosinase is considered one of the most specific markers of melanocytic differentiation. It is also expressed in glial cells, which like melanocytes, develop from the neuroectoderm. Tyrosinase is thus also a useful TuAA for glioblastomas, including glioblastoma multiform. Further details of tyrosinase as a TuAA is disclosed in U.S. Pat. No. 5,747,271, incorporated herein by reference in its entirety. In particular embodiments of the present invention there is provided the tyrosinase$_{369-377}$ epitope represented herein by SEQ. ID NO: 10 (Table 1).

Another TuAA employed in the present invention is Melan-A, also known as MART-1 (Melanoma Antigen Recognized by T cells). Melan-A/MART-1 is a melanin biosynthetic protein also expressed at high levels in melanomas. Melan-A/MART-1 is disclosed as a TuAA in U.S. Pat. Nos. 5,994,523; 5,874,560; and 5,620,886, each of which is incorporated herein by reference in its entirety. In preferred embodiments of the present invention there is provided the Melan-A TuAA, Melan-A$_{26-35}$ A27L analogue, represented herein by SEQ. ID NO: 9 (Table 1).

SSX-2, also known as Hom-Mel-40, is a member of a family of highly conserved cancer-testis (CT) antigens (Gure, A. O. et al., *Int. J. Cancer* 72:965-971, 1997, which is incorporated herein by reference in its entirety). Cancer-testis antigens are found in a variety of tumors, but are generally absent from normal adult tissues except testis. Expression of different members of the SSX family has been found in various tumor cell lines. SSX-2 as a TuAA is disclosed in U.S. Pat. No. 6,025,191, which is hereby incorporated by reference in its entirety. In particular embodiments of the present invention there is provided SSX-2$_{41-49}$ (SEQ. ID NO: 1) and an analogue thereof, SSX-2 Analogue (SEQ. ID NO: 5), Table 1.

NY-ESO-1, also known as CTAG-1 (Cancer-Testis Antigen-1) and CAG-3 (Cancer Antigen-3), is a cancer-testis antigen found in a wide variety of tumors. NY-ESO-1 as a TuAA is disclosed in U.S. Pat. No. 5,804,381, which is incorporated herein by reference in its entirety. In preferred embodiments, the present invention provides epitopes of NY-ESO-1 and analogues thereof, as represented by SEQ. ID NO: 2 and SEQ. ID NO: 6 respectively (Table 1).

Another TuAA contemplated in the present invention is PRAME, also known as MAPE, DAGE, and OIP4. PRAME is known in the art as a cancer-testis (CT) antigen. However, unlike many CT antigens, such as: MAGE, GAGE and BAGE, it is expressed in acute myeloid leukemias. PRAME as a TuAA is disclosed in U.S. Pat. No. 5,830,753, incorporated herein by reference in its entirety. In preferred embodiments, the present invention provides epitopes of PRAME and analogues thereof, as represented by SEQ. ID NO: 3 and SEQ. ID NO: 7 respectively (Table 1).

Yet another TuAA employed in the present invention is the prostate-specific membrane antigen (PSMA). PSMA is found to be highly expressed in prostate cancer cells. However, PSMA expression is also noted in normal prostate epithelium and in the neovasculature of non-prostatic tumors. PSMA as an anti-neovasculature preparation is disclosed in U.S. Provisional Patent Application Ser. No. 60/274,063, and U.S. patent application Ser. Nos. 10/094,699 (Publication No. 20030046714) and 11/073,347 (Publication No. 20050260234); each of which is incorporated herein by reference in its entirety. PSMA as a TuAA is described in U.S. Pat. No. 5,538,866 incorporated herein by reference in its entirety. In preferred embodiments, the present invention provides epitopes of PSMA and analogues thereof, as represented by SEQ. ID NO: 4 and SEQ. ID NO: 8 respectively (Table 1).

TABLE 1

PARTIAL LISTING OF SEQ. ID NOS.

| SEQ. ID NO. | IDENTITY | SEQUENCE |
|---|---|---|
| 1 | SSX-2$_{41-49}$ | KASEKIFYV |
| 2 | NY-ESO-1$_{157-165}$ | SLLMWITQC |
| 3 | PRAME$_{425-433}$ | SLLQHLIGL |
| 4 | PSMA$_{288-297}$ | GLPSIPVHPI |
| 5 | SSX-2 Analogue | KVSEKIFYV |
| 6 | NY-ESO-1 Analogue | SNvaLMWITQV |
| 7 | PRAME Analogue | SNvaLQHLIGNle |
| 8 | PSMA Analogue | GLPSIPVHPV |
| 9 | Melan-A$_{26-35}$ (A27L) Analogue | ELAGIGILTV |
| 10 | Tyrosinase$_{369-377}$ | YMDGTMSQV |
| 11 | Melan-A Analogue | ENvaAGIGILTV |
| 12 | Tyrosinase Analogue | YMDGTMSQNva |
| 13 | pBPL plasmid liberation sequence | I*KASEKIFYV*SLLM WITQC*KASEKIFY* VK |
| 14 | pRP12 plasmid liberation sequence | KR-SLLQHLIGL- GDAAY- SLLQHLIGL- ISPEKEEQYIA- SLLQHLIGL- KRPSIKR- GLPSIPVHPV |
| 15 | pSEM plasmid liberation sequence | MLLAVLYCL- ELAGIGILTV- YMDGTMSQV |

TABLE 1-continued

PARTIAL LISTING OF SEQ. ID NOS.

| SEQ. ID NO. | IDENTITY | SEQUENCE |
|---|---|---|
| 16 | pBPL encoded immunogenic polypeptide | MSLLMWITQCKA SEKIFYVGLPSIPV HPIGLPSIPVHPIK ASEKIFYVSLLMW ITQCKASEKIFYV KASEKIFYVRCGA RGPESRLLEFYLA MPFATPMEAELA RRSLAQDAPPLPV PGVLLKEFTVSGN ILTIRLTAADHRQ LQLSISSCLQQLSL LMWITQCFLPVFL AQPPSGQRR |
| 17 | pRP12 encoded immunogenic polypeptide | MNLLHETDSAVA TARRPRWLCAGA LVLAGGFFLLGFL FGWFIKSAQLAG AKGVILYSDPAD YFAPGVKSYPDG WNLPGGGVQRG NILNLNGAGDPLT PGYPANEYAYRR GIAEAVGLPSIPV HPIALQSLLQHLIG LSNLTHVLYPVPL ESYEDIHGTLHLE RLAYLHARLRELL CELGRPSMVWLS ANPCPHCGDRTF YDPEPILCPCFMP NKRSLLQHLIGLG DAAYSLLQHLIGL ISPEKEEQYIASLL QHLIGLKRPSIKR *GLPSIPVHPV* |
| 18 | pSEM encoded immunogenic polypeptide | MLLAVLYCLELA GIGILTVYMDGT MSQVGILTVILGV LLLIGCWYCRRR NGYRALMDKSLH VGTQCALTRRCP QEGFDHRDSKVS LQEKNCEPV |
| 22 | Melan-A26-35 | EAAGIGILTV |

The antigens of the invention, as discussed above, may be employed in various therapeutic regimens in treating a disease such as, but not limited to, cancer.

B. Immunogenic Compositions Comprising Plasmids in Combination with Peptides

As discussed above, the present invention provides immunogenic compositions for the treatment of cancer comprising plasmid(s) used in combination with synthetic peptide(s). Such an immunogenic protocol elicits a strong cell-mediated immune response to target a particular cancer thereby eliminating, eradicating or ameliorating the cancer in a subject. Preferred plasmids employed in the present invention are the pRP12 plasmid (SEQ ID NO. 21) (U.S. Provisional Patent Application No. 60/691,579 and the corresponding U.S. patent application Ser. No. 11/454,616 (Publication No. 20070004662), filed on the same date as the present application) both entitled "METHODS AND COMPOSITIONS TO ELICIT MULTIVALENT IMMUNE RESPONSES AGAINST DOMINANT AND SUBDOMINANT EPITOPES EXPRESSED ON CANCER CELLS AND TUMOR STROMA"), the pBPL plasmid (SEQ ID NO. 20), and the pSEM plasmid (SEQ ID NO. 19) disclosed in U.S. Provisional Patent Application No. 60/691,579 and U.S. patent application Ser. No. 10/292,413 (Publication No. 20030228634) respectively; each of which is incorporated herein by reference in its entirety (Note that in those documents pSEM is referred to as pMA2M). Additional plasmids that can be used are disclosed in these references and in U.S. patent application Ser. No. 10/225,568 (Publication No. 20030138808).

Thus, in various embodiments immunotherapeutic products comprise assemblages of immunogenic compositions. Such assemblages can comprise 1, 2, or 3 plasmids as a set of individual compositions or a single composition can comprise two or more plasmids. Such assemblages can also comprise multiple peptides corresponding to the epitopes expressed by the plasmids. Similarly, they can be provided as compositions comprising individual or multiple peptides. In some embodiments, an entraining plasmid or plasmids will be sold together with the corresponding amplifying peptides. In other embodiments, the multiple plasmids will be sold together, but without corresponding peptides. In still other embodiments sets of corresponding peptides will be sold together without the plasmid, for example, for subsequent rounds of amplification of the entrained response.

Therefore, in one particular embodiment of the present invention there is provided an assemblage comprising the pBPL plasmid (described in detail in U.S. application Ser. No. 10/292,413 (Publication No. 20030228634), entitled "EXPRESSION VECTORS ENCODING EPITOPES OF TARGET-ASSOCIATED ANTIGENS AND METHODS FOR THEIR DESIGN," which is hereby expressly incorporated by reference in its entirety) expressing the NY-ESO-$1_{157-165}$ (SEQ ID NO. 2) and SSX-$2_{41-49}$ (SEQ ID NO. 1) epitopes and the pRP12 plasmid (described in U.S. Provisional Application No. 60/691,579 U.S. patent application Ser. No. 11/454,616 (Publication No. 20070004662), filed on the same date as the present application, both entitled "METHODS AND COMPOSITIONS TO ELICIT MULTIVALENT IMMUNE RESPONSES AGAINST DOMINANT AND SUBDOMINANT EPITOPES EXPRESSED ON CANCER CELLS AND TUMOR STROMA," which are hereby expressly incorporated by reference in their entirety) expressing the PRAME$_{425-433}$ (SEQ ID NO. 3) and PSMA$_{288-297}$ (SEQ ID NO. 4) epitopes. The liberation sequence for the pBPL and pRP12 plasmids are represented herein as SEQ ID NO. 13 and 14 respectively, and are also disclosed in U.S. patent application Ser. No. 10/212,413 (Publication No. 20030228634), incorporated herein by reference. The plasmids encode the epitopes in such a manner that they can be expressed and presented by pAPC.

In another particular embodiment of the present invention there is provided an assemblage comprising the pSEM plasmid, (described in detail and referred to as pMA2M in U.S. patent application Ser. No. 10/292,413 (Publication No. 20030228634) incorporated herein by reference) expressing the A27L analogue of Melan-A$_{26-35}$ epitope (SEQ ID NO. 9) and the native tyrosinase$_{369-377}$ (SEQ ID NO. 10) epitope. The peptide analogues Melan-A$_{26-35}$ A27Nva (SEQ ID NO. 11) and tyrosinase$_{369-377}$ V377Nva (SEQ ID NO. 12) are disclosed in U.S. patent application Ser. No. 11/156,369, and U.S. Provisional Patent Application Ser. No. 60/691,889, both entitled "EPITOPE ANALOGS", each of which is hereby incorporated by reference in its entirety. The liberation sequence of this plasmid is represented herein as SEQ ID NO. 15 and is also disclosed in U.S. Provisional Patent Application No. 60/691,579, filed on Jun. 17, 2005; and U.S. patent application Ser. No. 11/454,616 (Publication No. 20070004662), filed on the same date as the present application, both entitled "METHODS AND COMPOSITIONS TO ELICIT MULTIVALENT IMMUNE RESPONSES AGAINST DOMINANT AND SUBDOMINANT EPITOPES, EXPRESSED ON CANCER CELLS AND TUMOR STROMA." The pSEM plasmid encodes the Melan-A and tyrosinase epitopes in a manner that allows for their expression and presentation by pAPCs.

In a further particular embodiment of the current invention there is provided an assemblage comprising the pBPL plasmid (described above) expressing the NY-ESO-$1_{157-165}$ (SEQ ID NO. 2) and SSX-$2_{41-49}$ (SEQ ID NO. 1) epitopes, and the pSEM plasmid (described above) (SEQ ID NO. 19) expressing the A27L analogue of Melan-$A_{26-35}$ epitope (SEQ ID NO. 9) and the native tyrosinase$_{369-377}$ (SEQ ID NO. 10) epitope. The peptide analogues Melan-$A_{26-35}$ A27Nva (SEQ ID NO 11), tyrosinase$_{369-377}$ V377Nva (SEQ ID NO 12), SSX-$2_{41-49}$ A42V (SEQ ID NO. 5), and NY-ESO-$1_{157-165}$ L158Nva, C165V (SEQ ID NO 6) are described in U.S. Provisional Application Ser. No. 60/580,962; U.S. patent application Ser. No. 11/155,929; U.S. Provisional Application Ser. No. 60/581,001; U.S. patent application Ser. No. 11/156,253; U.S. patent application Ser. No. 11/156,369 and U.S. Provisional Patent Application Ser. No. 60/691,889, each of which is hereby incorporated by reference in its entirety. The plasmids, pSEM (SEQ ID NO. 19) and pBPL (SEQ ID NO. 20), encode the respective epitopes and epitope analogues (Melan-A A27L analogue, tyrosinase, NY-ESO-1, and SSX-2) in a manner that they can be expressed and presented by pAPCs.

Another particular embodiment of the current invention relates to the assemblage comprising the pRP12 plasmid (described above) expressing the PSMA$_{288-297}$ (SEQ ID NO. 4) and PRAME$_{425-433}$ (SEQ ID NO. 3) epitopes and the pSEM plasmid (described above) expressing the A27L analogue of Melan-$A_{26-35}$ epitope (SEQ ID NO. 9) and the native tyrosinase$_{369-377}$ (SEQ ID NO. 10) epitope. The peptide analogues Melan-$A_{26-36}$ A27Nva (SEQ ID NO. 11), tyrosinase$_{369-377}$ V377Nva (SEQ ID NO. 12), PRAME$_{425-433}$ L426Nva, I433Nle (SEQ ID NO. 7), and PSMA$_{288-297}$ I297V (SEQ ID NO. 8) are described in U.S. Provisional Application Ser. No. 60/580,962; U.S. patent application Ser. No. 11/155,929; U.S. Provisional Application Ser. No. 60/581,001; U.S. patent application Ser. No. 11/156,253; U.S. patent application Ser. No. 11/156,369 and U.S. Provisional Patent Application Ser. No. 60/691,889, each of which is hereby incorporated by reference in its entirety. Both plasmids encode their respective epitopes, (Melan-A, tyrosinase, PRAME, and PSMA), in such a manner that they can be expressed and presented by pAPCs.

In further embodiments, each of the assemblages above include the peptides corresponding (that is capable of amplifying the response to) to the epitopes expressed by those plasmids. Other particular embodiments comprise an individual plasmid and one or both corresponding peptides. (Although the specific plasmids referred to herein are described as bivalent, they can also be amplified in a monovalent fashion).

As referred to herein, a PP therapeutic regimen entails administration of plasmid and peptide to target the PRAME and PSMA antigens. Similarly, an MT regimen targets Melan-A/tyrosinase antigens and an NS therapeutic regimen targets NY-ESO-1 and SSX-2 antigens.

II. Cell Proliferative Diseases and Methods of Screening

The immunogenic compositions of the present invention, comprising a plasmid and one or more peptides or analogues thereof, can be administered in treating a cell proliferative disease such as cancer, in a subject. Cancers that may be treated using the immunogenic composition of the present invention include, for example, melanoma, lung cancer including: non-small cell lung cancer (NSCLC) or small cell lung cancer (SCLC), hepatocarcinoma, retinoblastoma, astrocytoma, glioblastoma, leukemia, neuroblastoma, head and neck cancer, breast cancer, pancreatic cancer, renal cancer, bone cancer, testicular cancer, ovarian cancer, mesothelioma, cervical cancer, gastrointestinal cancer, lymphoma, colon cancer, bladder cancer and/or cancers of the blood, brain, skin, eye, tongue, gum. It is also anticipated that the immunogenic compositions of the present invention may be used to treat cell proliferative diseases other than cancer. Other cell proliferative diseases contemplated in the present invention may include, for example, dysplasias, pre-neoplastic lesions (e.g., adenomatous hyperplasia, prostatic intraepithelial neoplasia, cervical dysplasia, colon polyposis), or carcinoma in situ, but is not limited to such.

Cells or tissue obtained from patients predisposed to, or having a cancer, can be screened in order to better determine the appropriate immunotherapeutic regimen to administer to the patient. Such screening can include the steps of assaying the patient's tumor tissue for two or more expressed tumor associated antigens (TuAAs) in a preselected panel of antigens to develop an antigen profile for the tumor. An immunotherapeutic regimen can then be selected based on the antigen profile obtained. The regimen selected can comprise administering at least one immunotherapeutic agent targeting two, three, four, or more of the expressed antigens. The immunotherapeutic agent can comprise or encode an epitope restricted by the patient's class I MHC type, for each of two or more antigens expressed by the tumor. The antigen expression can be detected on neoplastic cells, or tumor-associated stromal cells, or both.

Immunotherapeutic regimens provided in the present invention include: the PP regimen where the target antigens are PRAME and PSMA; this regimen co-targets the vasculature and a cancer testes antigen. Another regimen provided by the present invention is the MT regimen where the target antigens are Melan-A and tyrosinase; this regimen targets tissue specific antigens associated with melanoma and glioblastoma. NS regimen of the invention relates to target antigens NY-ESO-1 and SSX-2 which are cancer testes antigens found with varying frequency in a wide variety of cancers. In other particular embodiments, of the invention, the regimens: PPNS (co-targeting PRAME, PSMA, NYESO-1, SSX2), NSMT (co-targeting NYESO-1, SSX2, Melan A and Tyrosinase) or PPMT (co-targeting PRAME, PSMA, Melan A, Tyrosinase) are provided.

A screening method employed in the present invention may include the steps of: assaying a patient's tumor tissue to detect one or more expressed polypeptides in a preselected panel, wherein the panel comprises two, or three, or four or more TuAAs and at least one lineage specific marker; and confirming the cancer diagnosis based on the assay. The panel can comprise of at least 2, 3, 4 or more TuAAs selected from the group consisting of NY-ESO-1, PRAME, PSMA, tyrosinase, melan-A/MART-1, and SSX protein. In some instances, the lineage specific marker can be a TuAA; alternatively, the lineage specific marker is not a TuAA. For example, in the case of melanoma and/or glioblastoma, the lineage specific marker can be tyrosinase, melan-A/MART-1, or gp100; in the case of prostate cancer, the lineage specific marker can be, PSA or PSMA.

As tumor antigen expression tends to be heterogeneous, any particular biopsy sample is likely not to give a complete indication of all the antigens expressed. Thus, it is not necessary that a patient's profile contain all of the antigens for treatment. The screening methods employed in the present invention may include an assay of a tumor tissue of the corresponding presumptive type for expression of a preselected panel of antigens. In some instances, a panel of TuAAs assembled for one tumor type can be used to screen other tumor types that can express at least some of the same antigens and an expression profile developed.

The immunogenic compositions of the present invention can be administered to patients with tumor tissue that express HLA-A2, particularly HLA-A*0201.

Exemplary methodology for obtaining a profile of antigen expression of a particular tumor that can be used to determine which antigen or combination of antigens are useful in treating a particular cancer can be is found in U.S. Provisional Application Ser. No. 60/580,969, filed Jun. 17, 2004; U.S. patent application Ser. No. 11/155,288 (Publication No. 20060008468), filed Jun. 17, 2005; and U.S. patent application Ser. No. 11/323,964, also filed on Jun. 17, 2005, all entitled "COMBINATIONS OF TUMOR-ASSOCIATED ANTIGENS IN DIAGNOSTICS FOR VARIOUS TYPES OF CANCERS"; each incorporated herein by reference in its entirety. Specific antigenic combinations of particular benefit in directing an immune response against particular cancers are disclosed in U.S. Provisional Application Ser. No. 60/479,554, filed on Jun. 17, 2003, U.S. patent application Ser. No. 10/871,708 (Publication No. 20050118186), filed on Jun. 17, 2004, (both entitled "COMBINATIONS OF TUMOR-ASSOCIATED ANTIGENS IN COMPOSITIONS FOR VARIOUS TYPES OF CANCERS"), and PCT Patent Application Publication No. WO 2004/112825, filed Jun. 17, 2004; each of which is incorporated herein by reference in its entirety.

III. Entraining-and-Amplifying Therapeutics for Administration

In a preferred embodiment, the present invention provides a composition comprising the combined use of recombinant DNA plasmid and synthetic peptides. administered using a prime (plasmid)/boost (peptide) approach. Such a composition may be delivered via lymph node injection according to an optimized immunization schedule. Embodiments of the current invention can be administered to patients with tumor tissue that expresses HLA-A2, particularly HLA-A*0201. Therefore, the immunogenic compositions comprising a plasmid and one or more peptides or analogues thereof can be administered in treating a cancer in a subject. The disclosed embodiments of the present invention relate to entrain-and-amplify therapeutics for carcinoma, including melanoma, that can be used to achieve a multivalent attack, offering the advantage of increasing the sensitivity of the tumor to attack.

Therefore, in particular embodiments, the present invention provides multivalent entraining-and-amplifying therapeutics for the treatment of cancer. Such multivalent therapeutics may target more than one antigen on a tumor cell. In instances where more than a single antigen on a tumor cell is targeted, the effective concentration of antitumor therapeutic is increased accordingly. Attack on stroma associated with the tumor, such as vasculature, can increase the accessibility of the tumor cells to the agent(s) targeting them. Thus, even an antigen that is also expressed on some normal tissue can receive greater consideration as a target antigen if the other antigens to be targeted in a multivalent attack are not also expressed by that tissue.

A. Bivalent Entrain-and-Amplify Therapeutic

An embodiment of the present invention relates to a bivalent entrain-and-amplify therapeutic for melanoma. Therefore, in the current invention there is provided an assemblage comprising the pSEM plasmid and peptides corresponding to Melan-$A_{26-35}$ (SEQ ID NO. 22) and tyrosinase$_{369-377}$ (SEQ ID NO. 10) epitopes administered as the MT regimen against melanoma. In preferred embodiments, the peptide analogues Melan-$A_{26-35}$ A27Nva (SEQ ID NO. 11) and/or tyrosinase$_{369-377}$ V377Nva (SEQ ID NO. 12) are utilized in the amplification step. The entrain-and-amplify protocol employed in the present invention is as disclosed above.

The pSEM plasmid assemblage can be delivered in a manner similar to that discussed above for the tetravalent entrain-and-amplify therapeutic for melanoma. Melanoma patients can be screened according to the methods disclosed herein and the MT regimen utilized with patients whose tumor antigen profile includes Melan-A and/or tyrosinase. Administration of the peptide boost can involve one or both of the antigens expressed by the plasmids.

Similarly the PP and NS regimens can be used for bivalent therapy using assemblages comprising pRP12 and peptides corresponding to the PSMA$_{288-297}$ (SEQ ID NO. 4) and PRAME$_{425-433}$ (SEQ ID NO. 3) epitopes, and pBPL and peptides corresponding to the NY-ESO-$1_{157-165}$ (SEQ ID NO. 2) and SSX-$2_{41-49}$ (SEQ ID NO. 1) epitopes, respectively. These bivalent regimens can be combined to create treatments of higher valency, selected embodiments of which are described below, and various sets of immunogenic compositions assembled to support them.

B. Tetravalent Entraining-and-Amplifying Therapeutics

One embodiment of the current invention relates to a tetravalent entrain-and-amplify therapeutic for carcinoma. Therefore, in one particular embodiment of the present invention there is provided an assemblage comprising the pBPL plasmid expressing the NY-ESO-$1_{157-165}$ (SEQ ID NO. 2) and SSX-$2_{41-49}$ (SEQ ID NO. 1) epitopes and the pRP12 plasmid expressing the PRAME$_{425-433}$ (SEQ ID NO. 3) and PSMA$_{288-297}$ (SEQ ID NO. 4) epitopes (referred to herein as the PP regimen), each administered as the entraining immunogens of an immunization strategy. An "entraining" immunogen as contemplated in the present invention includes in many embodiments an induction that confers particular stability on the immune profile of the induced lineage of T cells.

Additionally, four peptide compositions corresponding to the NY-ESO-1, SSX-2, PRAME and PSMA epitopes are administered as the amplification portion of the same immunization strategy as that of the entraining immuogen. In a preferred embodiment, the peptide analogues NY-ESO-$1_{157-165}$ L158Nva, C165V (SEQ ID NO. 6); SSX-$2_{41-49}$ A42V (SEQ ID NO. 5); PSMA$_{288-297}$ I297V (SEQ ID NO. 8); and/or PRAME$_{425-433}$ L426Nva, L433Nle (SEQ ID NO. 7) are utilized in the amplification step. As contemplated in the present invention, the term "amplifying or amplification", as of a T cell response, includes in many embodiments a process for increasing the number of cells, the number of activated cells, the level of activity, rate of proliferation, or similar parameter of T cells involved in a specific response.

The entrain-and-amplify protocol employed in the present invention is described in greater detail in U.S. Provisional Application No. 60/640,402, U.S. patent application Ser. No. 10/871,707 (Publication No. 20050079152), and U.S. patent application Ser. No. 11/323,572, each entitled "METHODS TO ELICIT, ENHANCE AND SUSTAIN IMMUNE RESPONSES AGAINST MHC CLASS I-RESTRICTED EPITOPES, FOR PROPHYLACTIC OR THERAPEUTIC PURPOSES" each of which is incorporated herein by reference in their entirety.

In preferred embodiments of the present invention, the plasmids are administered intranodally as an entraining immunogen to the inguinal lymph nodes, one to the left side and one to the right. Subsequently, the peptides are sequentially administered intranodally as amplifying immunogens, two on separate days to the left node and the other two on separate days to the right node. It is preferred, but not required, that the peptides be administered to the same lymph node that received the plasmid encoding the corresponding epitopes.

Carcinoma patients, especially those with ovarian, colorectal, pancreatic, or renal cell carcinoma, can be screened according to the methods disclosed herein and PP and or NS therapeutic regimens administered to patients whose tumor profile includes PRAME, PSMA, NY-ESO-1, and/or SSX-2. It is noted that the NY-ESO-1 epitope is also found in LAGE 1a/s, so the presence of this antigen in a profile can also be considered in the tumor profile. As tumor antigen expression tends to be heterogeneous, any particular biopsy sample is likely not to give a complete indication of all the antigens expressed. Thus, it is not necessary that a patient's profile contain all four of the antigens for that patient to be a candidate for treatment with therapeutics of the invention. However, it is preferred that the profile contain 2, 3, or 4 of the antigens.

C. Tetravalent Entraining-and-Amplifying Therapeutics for Melanoma

An embodiment of the present invention relates to a tetravalent entrain-and-amplify therapeutic for melanoma, comprising the plasmids pSEM and pBPL and the corresponding peptides. The pSEM plasmid encodes the A27L analogue of the Melan-$A_{26-35}$ (SEQ ID NO. 9) epitope and the native tyrosinase (tyrosinase$_{369-377}$ (SEQ ID NO. 10)) epitope sequence (referred to herein as the MT regimen). The pBPL plasmid encodes NY-ESO-$1_{157-165}$ (SEQ ID NO. 2) and SSX-$2_{41-49}$ (SEQ ID NO. 1) native sequences. The assemblage comprising the plasmid is administered as the entraining portion of an immunization strategy against melanoma. Additionally, four peptide compositions corresponding to the NY-ESO-1, SSX-2, Melan-A and tyrosinase epitopes are administered as the amplification portion of the same immunization strategy. In a preferred embodiment, the peptide analogues Melan-$A_{26-35}$ A27Nva (SEQ ID NO. 11), tyrosinase$_{369-377}$ V377Nva (SEQ ID NO. 12), SSX-$2_{41-49}$ A42V (SEQ ID NO. 5), and NY-ESO-$1_{157-165}$ L158Nva, C165V (SEQ ID NO. 6) are utilized in the amplification step.

For treatment of a cancer such as melanoma, the plasmids are administered intranodally to the inguinal lymph nodes as entraining immunogens. Subsequently the peptides are administered intranodally, preferably one to the left node, the other to the right on any particular day as amplifying immunogens. Melanoma patients can be screened according to the methods disclosed herein and the appropriate regimens administered to patients whose tumor antigen profile includes Melan-A and/or tyrosinase. Administration of the peptide boost can involve 2, 3, or 4 of the antigens expressed by the plasmids.

D. Tetravalent Entraining-and-Amplifying Therapeutics for Glioblastoma

In a further particular embodiment of the present invention there is provided a tetravalent entrain-and-amplify therapeutic applicable to melanoma that is applied to other cancers such as glioblastoma. One such embodiment relates to the composite pRP12 plasmid (described above) expressing the PSMA$_{288-297}$ (SEQ ID NO. 4) and PRAME$_{425-433}$ (SEQ ID NO. 3) epitopes and the pSEM plasmid (described above) expressing the A27L analogue of Melan-$A_{26-35}$ epitope (SEQ ID NO. 9) and the native tyrosinase$_{369-377}$ (SEQ ID NO. 10) epitope administered as the entraining portion of an immunization strategy. Additionally, four peptide compositions corresponding to the PSMA, PRAME, Melan-A and tyrosinase epitopes are administered as the amplification portion of the same immunization strategy. In a preferred embodiment, the peptide analogues Melan-$A_{26-35}$ A27Nva (SEQ ID NO. 11), tyrosinase$_{369-377}$ V377Nva (SEQ ID NO. 12), PRAME$_{425-433}$ L426Nva, I433Nle (SEQ ID NO. 7), and PSMA$_{288-297}$ I297V (SEQ ID NO. 8) are utilized in the amplification step.

Cancer patients can be screened according to the methods disclosed herein and the PP and/or MT regimens administered to patients whose tumor antigen profile includes PRAME, PSMA, Melan-A and/or tyrosinase. Administration of the peptide boost can involve 2, 3, or 4 of the antigens expressed by the plasmids.

IV. Methods of Delivering Compositions of the Present Invention

In the present invention, the preferred administration of the immunogenic composition comprising recombinant DNA plasmid as a prime and synthetic peptide(s) as a boost, is via lymph node injection. The plasmid (prime) may be administered separately from the peptide (boost). Embodiments of the present invention can encompass two monovalent plasmids expressing single immunogens in place of one bivalent plasmid expressing both immunogens. In other embodiments, a trivalent plasmid expressing three immunogens in place of one bivalent and one monovalent plasmid may be employed. In some instances a trivalent plasmid and one monovalent plasmid in place of a tetravalent plasmid; or two bivalent plasmids in place of a tetravalent plasmid may be employed. Whichever combination of the compositions of the invention is employed, lymph node injection is preferred as it allows for delivery directly into the organs where the immune responses are initiated and amplified according to an optimized immunization schedule.

To introduce the immunogenic composition into the lymphatic system of the patient the composition is preferably directed to a lymph vessel, lymph node, the spleen, or other appropriate portion of the lymphatic system. In some embodiments each component is administered as a bolus. In other embodiments one or more components are delivered by infusion, generally over several hours to several days. Preferably, the composition is directed to a lymph node such as an inguinal or axillary node by inserting a catheter or needle to the node and maintaining the catheter or needle throughout the delivery. Suitable needles or catheters are available made of metal or plastic (e.g., polyurethane, polyvinyl chloride (PVC), TEFLON, polyethylene, and the like). In inserting the catheter or needle into the inguinal node for example, the inguinal node is punctured under ultrasonographic control using a Vialon™ Insyte W™ cannula and catheter of 24G3/4 (Becton Dickinson, USA) which is fixed using Tegaderm™ transparent dressing (Tegaderm™, St. Paul, Minn., USA). This procedure is generally done by an experienced radiologist. The location of the catheter tip inside the inguinal lymph node is confirmed by injection of a minimal volume of saline, which immediately and visibly increases the size of the lymph node. The latter procedure allows confirmation that the tip is inside the node. This procedure can be performed to ensure that the tip does not slip out of the lymph node and can be repeated on various days after implantation of the catheter. In the event that the tip does slip out of location inside the lymph node, a new catheter can be implanted.

The therapeutic composition(s) of the present invention may be administered to a patient in a manner consistent with standard vaccine delivery protocols that are well known to one of ordinary skill in the art. Methods of administering immunogenic compositions of the present invention comprising plasmids and peptides or peptide analogues of TuAAs include, without limitation, transdermal, intranodal, perinodal, oral, intravenous, intradermal, intramuscular, intraperitoneal, and mucosal administration, delivery by injection or instillation or inhalation. A particularly useful method of vaccine delivery to elicit a CTL response is disclosed in Australian Patent No. 739189; U.S. Pat. Nos. 6,994,851 and 6,977,074 both entitled "A METHOD OF INDUCING A CTL RESPONSE".

Various parameters need to be taken into account in delivering or administering an immunogenic composition to a subject. In addition, a dosage regimen and immunization schedule may be employed. Generally the amount of the components in the therapeutic composition will vary from patient to patient and from antigen to antigen, depending on such factors as: the activity of the antigen in inducing a response; the flow rate of the lymph through the patient's system; the weight and age of the subject; the type of disease and/or condition being treated; the severity of the disease or condition; previous or concurrent therapeutic interventions; the capacity of the individual's immune system to synthesize antibodies; the degree of protection desired; the manner of administration and the like, all of which can be readily determined by the practitioner.

In general the therapeutic composition may be delivered at a rate of from about 1 to about 500 microliters/hour or about 24 to about 12000 microliters/day. The concentration of the antigen is such that about 0.1 micrograms to about 10,000 micrograms of the antigen will be delivered during 24 hours. The flow rate is based on the knowledge that each minute approximately about 100 to about 1000 microliters of lymph fluid flows through an adult inguinal lymph node. The objective is to maximize local concentration of vaccine formulation in the lymph system. Some empirical investigation on patients may be necessary to determine the most efficacious level of infusion for a given vaccine preparation in humans.

In particular embodiments, the immunogenic composition of the present invention may be administered as a plurality of sequential doses. Such a plurality of doses may be 2, 3, 4, 5, 6 or more doses as is needed. In further embodiments of the present invention, it is contemplated that the doses of the immunogenic composition would be administered within about seconds or minutes of each other into the right or left inguinal lymph nodes. For example, the plasmid (prime) may first be injected into the right lymph node followed within seconds or minutes by a second plasmid into the left inguinal lymph node. In other instances the combination of one or more plasmids expressing one or more immunogens may be administered. It is preferred that the subsequent injection following the first injection into the lymph node be within at about 1, 2, 3, 4, 5, 6, 7, 8, 9, 10 or more minutes but not greater than about 30, 40, 50, or 60 minutes of the first injection. Similar considerations apply to the administration of two peptides individually to the right and left lymph nodes. It may be desirable to administer the plurality of doses of the immunogenic composition of the invention at an interval of days, where several days (1, 2, 3, 4, 5, 6, or 7, or more days) lapse between subsequent administrations. In other instances it may be desirable for subsequent administration(s) of the compositions of the invention to be administered via bilateral inguinal lymph node injection within about 1, 2, 3, or more weeks or within about 1, 2, 3, or more months following the initial dose administration.

Administration may be in any manner compatible with the dosage formulation and in such amount as will be therapeutically effective. An effective amount or dose of an immunogenic composition of the present invention is that amount needed to provide a desired response in the subject to be treated.

V. Examples

The following examples are included to demonstrate preferred embodiments of the invention. It should be appreciated by those of skill in the art that the methodology disclosed in the examples which follow represent methodologies discovered by the inventors to function well in the practice of the invention, and thus can be considered to constitute preferred modes for its practice. However, those of skill in the art should, in light of the present disclosure, appreciate that one can make many changes to the specific disclosed embodiments and still obtain a like or similar result within the spirit and scope of the invention.

Example 1

Experimental Procedure

Animals

Since the immune response against human T cell epitopes cannot be studied in original nonclinical models due to the inherent MHC-restriction of immunity, a genetically manipulated mouse model was chosen that expresses the human A*0201 gene (Pascolo et al., 1997), which is frequently expressed in the human population. In contrast to immune deficient mice (the basis for xenograft models), the A*0201 transgenic model (HHD) is immune competent, thus allowing the evaluation of active immunotherapeutic strategies.

Therefore, female H-2 class I-negative (knockout) HLA-A2.1-transgenic HHD mice, 8-12 weeks of age, were used in these studies. The animals were housed under pathogen-free conditions.

Methodology

The bivalent pSEM plasmid (non-replicating recombinant DNA) encoding for the tumor-associated antigens Melan-$A_{26-35}$ A27L analogue (SEQ ID NO. 9) and Tyrosinase$_{369-377}$ (SEQ ID NO. 10) and pBPL bivalent plasmid encoding for tumor-associated antigens SSX-$2_{41-49}$ (SEQ ID NO. 1) and NY-ESO-$1_{157-165}$ (SEQ ID NO. 2) were evaluated regarding the ability to prime a Tc1 (gamma interferon-producing) immune response in Examples 2-6. The Melan-$A_{26-35}$ (A27Nva; ENvaAGIGILTV (SEQ ID NO. 11)) peptide analogue, Tyrosinase$_{369-377}$ (V377Nva; YMDGTMSQNva (SEQ ID NO. 12)) peptide analogue, NY-ESO-$1_{157-165}$ (L158Nva, C165V; S(Nva)LMWITQV (SEQ ID NO. 6)) peptide analogue, and SSX-$2_{41-49}$ (A42V; KVSEKIFY (SEQ ID NO. 5)) peptide analogue were used for subsequent boosting.

Plasmids were formulated in clinical buffer (127 mM NaCl, 2.5 mM Na$_2$HPO$_4$, 0.88 mM KH$_2$PO$_4$, 0.25 mM Na$_2$EDTA, 0.5% ETOH, in H$_2$O). The Melan A$_{26-35}$ (A27Nva) (SEQ ID NO. 11) analogue was formulated in PBS at 1.0 mg/ml concentration. Similarly, the Tyrosinase$_{369-377}$ (V377Nva) (SEQ ID NO. 12) analogue was formulated in PBS at 1.0 mg/ml concentration. The SSX-$2_{41-49}$ (A42V) (SEQ ID NO. 5) analogue was formulated in PBS at 1.0 mg/ml concentration while the NY-ESO-$1_{157-165}$ (L158Nva, C165V) (SEQ ID NO. 6) peptide analogue was prepared for immunization in PBS containing 5% DMSO at a concentration of 0.5 mg/ml. Cytometry data were collected using a BD FACS Calibur flow cytometer and analyzed using CellQuest software by gating on the lymphocyte population.

Intranodal Delivery of Plasmids and Peptides

The dose preparations were administered via bilateral inguinal intranodal injection on Days 1, 4, 15, 18, 29, 32, 49, and 53 of the study. Mice were anesthetized by inhalation of isoflurane and surgeries were conducted under aseptic conditions. Following preparation for surgery, an incision 0.5-1 cm in length was made in the inguinal fold exposing the inguinal lymph node. A maximum volume of 25 μL (25 μg in a 1 mg/mL solution) of plasmid or peptide was injected directly into the right and left inguinal lymph node using a 0.5 mL insulin syringe. The incision was closed with sterile 6.0 nylon skin sutures.

Plasmid (Prime)/Peptide (Boost) Immunization Schedule

Three groups of female HHD animals were immunized as described above with a mixture of pSEM/pBPL (100 μg/day) to the bilateral inguinal lymph nodes. Group 1 (n=10 mice) received plasmid injections on Days 1, 4, 15, 18, 28, 32, 49, and 53; Group 2 and Group 3 (n=25 mice per group) received plasmid injections on Days 1, 4, 15, and 18 respectively as shown in Table 2 (below).

Animals from Group 2 were boosted in the right lymph node with Tyrosinase V377Nva (SEQ ID NO. 12) (25 μg/day) and in the left lymph node with SSX-2 A42V (SEQ ID NO. 5) (25 μg/day) peptides on days 28, 32, 49, and 53. Group 3 animals were boosted in the right lymph node with Tyrosinase V377Nva (SEQ ID NO. 12) (25 μg/day) and in the left lymph node with SSX-2 A42V (SEQ ID NO. 5) (25 μg/day) peptides on days 28 and 32 then were boosted in the right lymph node with NY-ESO-1 L158Nva, C165V (SEQ ID NO. 6) (12.5 μg/day) and in the left lymph node with Melan A A27Nva (SEQ ID NO. 11) (25 μg/day) peptides on days 49 and 53 as also shown in Table 2.

HLA-A*0201 SSX-2 (KASEKIFYV (SEQ ID NO. 1))-PE MHC tetramer (Beckman Coulter, T02001), HLA-A*0201 NY-ESO (SLLMWITQC (SEQ ID NO. 2))-APC MHC tetramer (Beckman Coulter, T02001), HLA-A*0201 Melan A A27L (ELAGIGILTV (SEQ ID NO. 9))-PE MHC tetramer (Beckman Coulter, T02001), HLA-A*0201 Tyrosinase (YMDGTMSQV (SEQ ID NO. 10))-APC MHC tetramer (Beckman Coulter, T02001). These cells were then co-stained using FITC conjugated rat anti-mouse CD8a (Ly-2) monoclonal antibody (BD Biosciences, 553031). Data were collected using a BD FACS Calibur flow cytometer and analyzed using Cellquest software by gating on the lymphocyte population and calculating the percent of tetramer positive cells within the CD8$^+$ CTL population.

Interferon-γ (IFN-γ) ELISpot Assay

Instead of measuring cytotoxicity, the CD8$^+$ CTL response can be assessed by measuring IFN-γ production by specific effector cells in an ELISPOT assay. In this assay, antigen-presenting cells (APC) are immobilized on the plastic surface of a microtiter well and effector cells are added at various effector:target ratios. The binding of APCs by antigen-specific effector cells triggers the production of cytokines including IFN-γ by the effector cells. The cells can be stained to detect the presence of intracellular IFN-γ and the number of positively staining foci (spots) counted under a microscope.

Spleens were isolated on days 27 and 62 from euthanized animals, subjected to the plasmid/peptide immunization schedule as described above. The mononuclear cells, after

TABLE 2

Immunization Schedule

| | | Plasmids (prime) | | Peptide (boost) | | |
|---|---|---|---|---|---|---|
| | | | | Peptide and Lymph Node | | |
| Group | N* | Plasmids | Days | Each Dose (R/L) | Days | Each Dose |
| 1 | 10 | pSEM + pBPL | 1, 4, 15, 18, 28, 32, 49, 53 | 100 μg | — | — |
| 2 | 25 | pSEM + pBPL | 1, 4, 15, 18, | 100 μg | Tyrosinase (R) | 28, 32, 49, 53 | 25 μg |
| | | | | | SSX-2 (L) | 28, 32, 49, 53 | 25 μg |
| 3 | 25 | pSEM + pBPL | 1, 4, 15, 18 | 100 μg | Tyrosinase (R) | 28, 32 | 25 μg |
| | | | | | SSX-2 (L) | 28, 32 | 25 μg |
| | | | | | NY-ESO-1 (R) | 49, 53 | 12.5 μg |
| | | | | | Melan A (L) | 49, 53 | 25 μg |

Tetramer Analysis

Enumeration of CD8$^+$ antigen-specific T cells requires cognate recognition of the T cell receptor (TCR) by a Class I MHC/peptide complex. This can be accomplished using Class 1 tetramers which are composed of a complex of four HLA MHC Class 1 molecules each bound to the specific peptide and conjugated with a fluorescent protein. Thus tetramer assays allow quantitation of the total T cell population specific for a given peptide complexed in a particular MHC molecule. Flow cytometry is employed in quantifying binding of cells with the appropriate T cell receptor to the labeled tetramers. Furthermore, since binding does not depend on functional pathways, this population includes all specific CD8$^+$ T-cells regardless of functional status.

The CTL response was measured in animals immunized as described in the above plasmid/peptide immunization schedule, 7 days following the last plasmid (Day 25) and peptide immunizations (Days 39 and 60). Mononuclear cells were isolated from peripheral blood after density centrifugation (Lympholyte Mammal, Cedarlane Labs), and stained with density centrifugation (Lympholyte Mammal, Cedarlane Labs, Burlington, N.C.), were resuspended in HL-1 medium. Splenocytes ($5 \times 10^5$, or $3 \times 10^5$ cells per well) were incubated with 10 μg of Melan-A$_{26-35}$ (A27L) (SEQ ID NO. 9), Tyrosinase$_{369-377}$ (SEQ ID NO. 10), SSX-2$_{41-49}$ (SEQ ID NO. 1), or NY-ESO-1$_{157-165}$ (SEQ ID NO. 2) natural peptide in triplicate wells of a 96 well filter membrane plates (Multiscreen IP membrane 96-well plate, Millipore. Boston, Mass.). Samples were incubated for 42 hours at 37° C. with 5% CO$_2$ and 100% humidity prior to development. Mouse IFN-γ coating antibody (IFN-γ antibody pair, U-CyTech Biosciences, The Netherlands) was used as a coating reagent prior to incubation with splenocytes, followed by the accompanied biotinylated detection antibody. GABA conjugate and proprietary substrates from U-CyTech were used for IFN-γ spot development. The CTL response in immunized animals was measured 24 hours after development on the AID International plate reader using ELISpot Reader software version 3.2.3 calibrated for IFN-γ spot analysis.

$^{51}$Chromium-Release Assay

The chromium release assay, is a well known assay for evaluating CTL activity. Briefly, target cells expressing antigen on their surface are labeled with a radioactive isotope of chromium ($^{51}$Cr). Patient cells are then mixed with the target cell and incubated for several hours. Lysis of antigen-expressing cells release $^{51}$Cr into the medium. Cell-specific lysis is calculated by comparing lysis of target cells expressing the antigen(s) of interest or control antigen(s) in the presence or absence of patient effector cells, and is usually expressed as the % specific lysis.

Example 2

Immunization with Plasmids pSEM and pBPL Prior to Peptide Boost

The purpose of this study was to determine whether immunization with the plasmids pSEM and pBPL could induce a tetravalent response against the four tumor associated antigens SSX-2$_{41-49}$ (SEQ ID NO. 1), NY-ESO-1$_{157-165}$ (SEQ ID NO. 2), Melan-A$_{26-35}$ (A27L) (SEQ ID NO. 9) and Tyrosinase$_{369-377}$ (SEQ ID NO. 10).

Three groups of female HHD animals (H-2 class I-negative (knockout) HLA-A2.1-transgenic HHD mice, 8-12 weeks of age) were immunized with a mixture of pSEM/pBPL (100 μg/day) to the bilateral inguinal lymph nodes. Group 1 (n=10 mice) received plasmid injections on Days 1, 4, 15, 18, 28, 32, 49, and 53; Group 2 and Group 3 (n=25 mice per group) received plasmid injections on Days 1, 4, 15, and 18 respectively (Table 2; above). On day 25, blood was collected from the immunized animals, and CD8$^+$ T cell analysis was performed using a tetramer assay as discussed elsewhere herein. Responses were compared to naïve littermate control mice (n=5).

FIG. 1 shows tetramer data from animals that were primed with four injections of a mixture of the pSEM and pBPL bivalent plasmids (n=60), which are designed to encode for Melan-A$_{26-35}$ (A27L) (SEQ ID NO. 9)/tyrosinase$_{369-377}$ (SEQ ID NO. 10), and NY-ESI-1$_{157-165}$ (SEQ ID NO. 2)/SSX-2$_{41-49}$ (SEQ ID NO. 1) respectively, prior to peptide boost. Animals primed with four injections of the pSEM/pBPL plasmid mixture at a daily dose of 100 μg exhibited a trivalent SSX-2, NY-ESO-1, and Melan-A response (Groups 1-3, n=60 total) but failed to generate any tyrosinase specific CTLs as measured by tetramer assay. In addition, Melan-A and NY-ESO-1 were revealed to be the dominant epitopes expressed by the bivalent plasmids pSEM and pBPL respectively, as shown in FIG. 1.

Example 3

Individual Immunization with Plasmid Primed SSX-2/Tyrosinase

It was assessed whether boosting with the subdominant epitope peptides alone following plasmid priming was sufficient to achieve a tetravalent immune response. Therefore, animals from Group 2 above, were boosted with the subdominant epitopes, tyrosinase V377Nva (SEQ ID NO. 12) and SSX-2 A42V (SEQ ID NO. 5) peptide analogues and immune responses were compared to a naïve control.

Animals were primed with a plasmid mixture of pBPL+pSEM on days 1, 4, 15, and 18 (100 μg/day) in bilateral inguinal lymph nodes followed by a peptide boost consisting of SSX-2$_{41-49}$ A42V (SEQ ID NO. 1) in the left lymph node and Tyrosinase$_{369-377}$ V377Nva (SEQ ID NO. 12) on the right lymph node on days 28 and 32 (25 μg/day). On day 39, seven days following the last peptide injection, blood was collected from the immunized animals, and CD8$^+$ T cell analysis was performed using a tetramer assay as discussed elsewhere herein.

Figure 2:
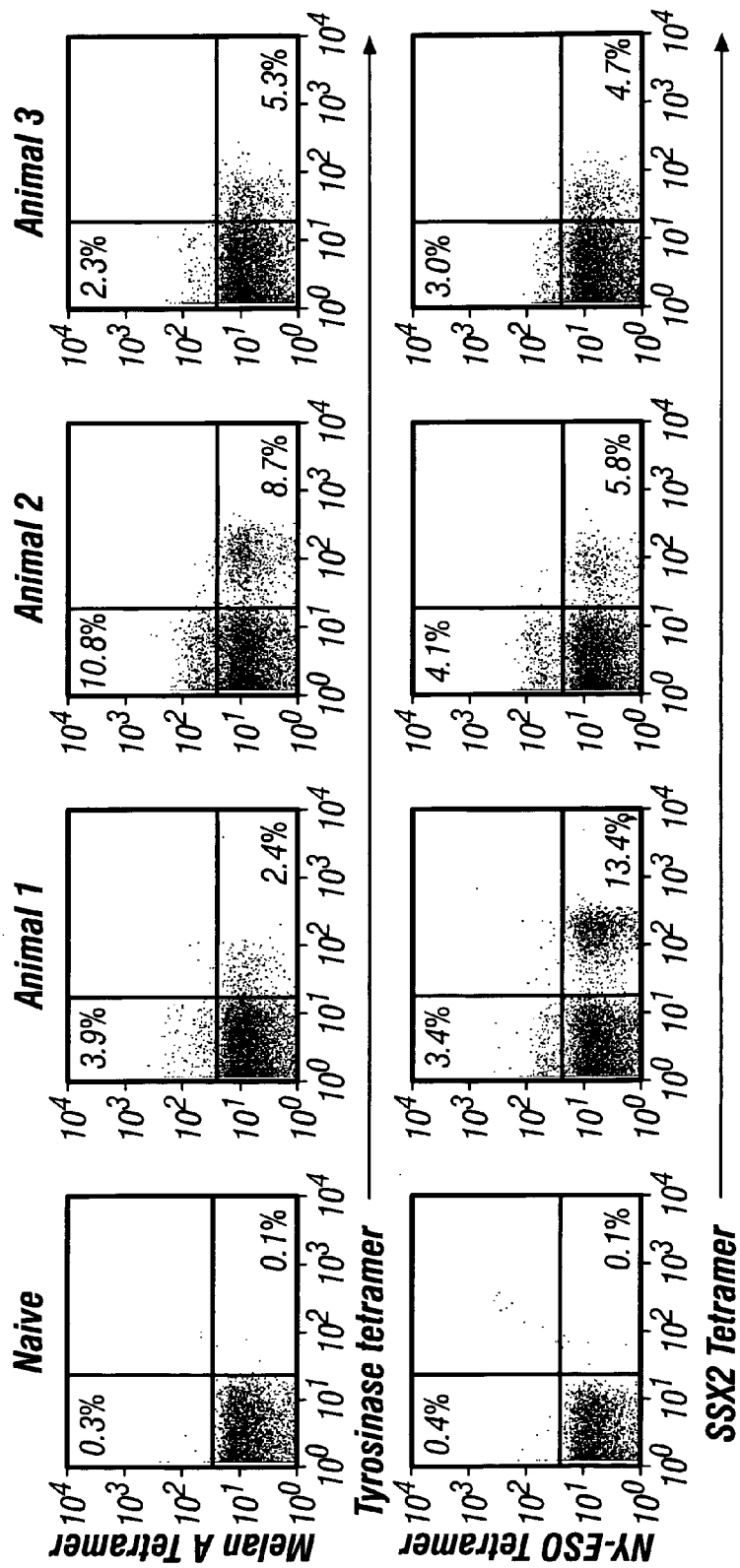
FIG. 2. Melan-A/Tyrosinase, SSX-2/NY-ESO-1 tetramer analysis was performed on day 39 demonstrating a tetravalent immune response in individual animals. Animals were primed with a plasmid mixture of pBPL+pSEM on days 1, 4, 15, and 18 (100 μg/day) in bilateral inguinal lymph nodes followed by a peptide boost consisting of SSX2$_{41-49}$ A42V (SEQ ID. NO. 5) in the left lymph node and Tyrosinase$_{369-377}$ V377Nva (SEQ ID. NO. 12) on in the right lymph node on days 28 and 32 (25 μg/day). Representative animals (n=3) from Group 2 are shown and compared to tetramer values for an untreated naïve littermate control.

FIG. 2 shows the tetravalent responses from peripheral blood on day 39 following the Tyrosinase and SSX-2 peptide boost, generated in three representative immunized animals as compared to a selected naïve control animal using a tetramer flow cytometry assay. For example, animal 2 demonstrated tetramer responses specific to SSX-2 (5.8%), NY-ESO-1 (4.1%), tyrosinase (8.7%) and Melan A (10.8%). These data taken together, represent specific CTL responses comprised of 29.4% of the total CD8$^+$ T cell repertoire. Furthermore, the results show that boosting with the subdominant epitope peptides alone, following plasmid priming, was sufficient to achieve a tetravalent immune response.

Example 4

Immunization with Plasmid Primed SSX-2/Tyrosinase

In order to generate a more balanced tetravalent immune response, animals were boosted with the sub-dominant peptide epitopes Tyrosinase$_{369-377}$ (V377Nva) (SEQ ID NO. 12) and SSX-2$_{41-49}$ (A42V) (SEQ ID NO. 5) (Groups 2 and 3, n=50) and immune responses were compared to animals boosted with a mixture of pSEM/pBPL plasmid (Group 1, n=10) or naïve controls (n=10).

Melan-A/Tyrosinase, SSX2/NY-ESO-1 tetramer analysis (as described above), was performed on day 39, seven days following the last peptide injection. Group 1 animals (n=10) were primed with a plasmid mixture of pBPL+pSEM on days 1, 4, 15, and 18 (100 μg/day) followed by a boost with a plasmid mixture of pBPL+pSEM on days 28 and 32 (100 μg/day) in bilateral inguinal lymph nodes. Group 2 and 3 animals (n=50) were primed with a plasmid mixture of pBPL+pSEM on days 1, 4, 15, and 18 (100 μg/day) in bilateral inguinal lymph nodes followed by a peptide boost consisting of SSX2$_{41-49}$ A42V (SEQ ID NO. 5) in the left lymph node and Tyrosinase$_{369-377}$ V377Nva (SEQ ID NO. 12) in the right lymph node on days 28 and 32 (25 μg/day).

Figure 3:
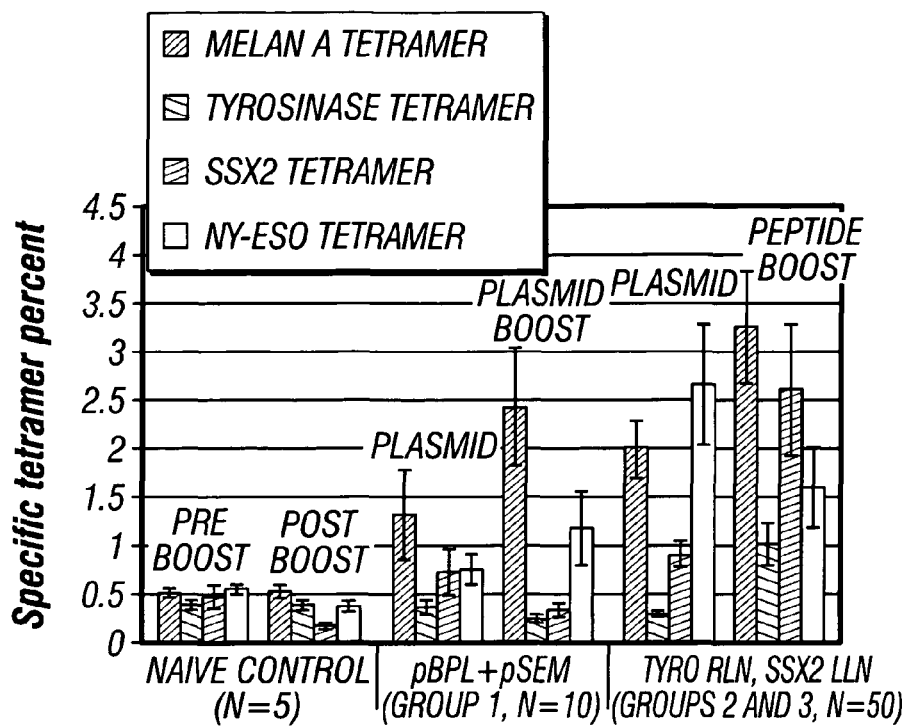
FIG. 3. Tetramer analysis of pSEM/pBPL primed, SSX-2/Tyrosinase boosted animals. Melan-A/Tyrosinase, SSX-2/NY-ESO-1 tetramer analysis was performed on day 39, 7 days following the last peptide injection. Group 1 animals (n=10) were primed with a plasmid mixture of pBPL+pSEM on days 1, 4, 15, and 18 (100 μg/day) followed by a boost with a plasmid mixture of pBPL+pSEM on days 28 and 32 (100 μg/day). Group 2 and 3 animals (n=50) were primed with a plasmid mixture of pBPL+pSEM similar to Group 1 followed by a peptide boost consisting of SSX-2$_{41-49}$ A42V (SEQ ID. NO. 5) in the left lymph node and Tyrosinase$_{369-377}$ V377Nva (SEQ ID. NO. 12) in the right lymph node on days 28 and 32 (25 μg/day). Average tetramer values (Melan A, Tyrosinase, SSX-2, and NY-ESO-1) were compared to untreated naïve littermate controls (n=5) and represent the average+/−SEM.

Average tetramer values for Melan A, Tyrosinase, SSX2, and NY-ESO-1 were compared to untreated naïve littermate controls (n=5) and represent the average+/–SEM. FIG. 3 shows the immune responses prior to and following the tyrosinase and SSX-2 boost for Groups 2 and 3 (n=50) compared to Group 1 (n=10; plasmid alone).

Following the plasmid boost, the predominant immune response was Melan-A and NY-ESO-1 specific (Group 1), as observed in FIG. 1. On the other hand, animals primed with the plasmid mixture and boosted with the subdominant peptides boosted their tyrosinase response >2 fold and SSX-2 response >2.5 fold, thereby establishing a balanced tetravalent immune response FIG. 3.

Thus, the data shows that a balanced tetravalent immune response was achieved by boosting with the sub-dominant epitope peptides, Tyrosinase$_{369-377}$ (V377Nva) (SEQ ID NO. 12), and SSX-2$_{41-49}$ (A42V) (SEQ ID NO. 5).

Example 5

IFN-γ ELISPOT Analysis of First and Second Peptide Boost

The tetramer data obtained in the above Examples was confirmed by measuring the frequency of interferon gamma producing (IFNγ) cells following the peptide boost in select animals from Groups 2. IFN-γ ELISpot analysis was conducted following the first peptide boost (FIG. 4A) and a second peptide boost (FIG. 4B)

ELISPOT analysis, as described elsewhere herein, was performed by sacrificing representative animals on day 41, nine days following the last peptide boost. Group 1 animals (n=3 sacrificed) were primed with a plasmid mixture of pBPL+pSEM on days 1, 4, 15, and 18 (100 μg/day) followed by a boost with a plasmid mixture of pBPL+pSEM on days 28 and 32 (100 μg/day) in bilateral inguinal lymph nodes. Group 2 animals (n=6 sacrificed) were primed with a plasmid mixture of pBPL+pSEM on days 1, 4, 15, and 18 (100 μg/day) in bilateral inguinal lymph nodes followed by a peptide boost consisting of SSX2$_{41-49}$ A42V (SEQ ID NO. 5) in the left lymph node and Tyrosinase$_{369-377}$ V377Nva (SEQ ID NO. 12) in the right lymph node on days 28 and 32 (25 μg/day). Antigen specific (Melan A, Tyrosinase, SSX2, and NY-ESO-1) interferon-γ spot forming cells per spleen were compared to untreated naïve littermate controls (n=3), FIG. 4A.

Following the second peptide boost, ELISPOT analysis was performed by sacrificing representative animals on day 63, ten days following the second peptide boost. Group 1 animals (n=3 sacrificed) received injections of a mixture of pBPL+pSEM on days 1, 4, 15, 18, 28, 32, 49, and 53 (100 μg/day) in bilateral inguinal lymph nodes. Group 2 animals (n=4 sacrificed) received injections of a mixture of pBPL+pSEM on days 1, 4, 15, and 18 (100 μg/day) in bilateral inguinal lymph nodes followed by a peptide boost consisting of SSX2$_{41-49}$ A42V in the left lymph node and Tyrosinase$_{369-377}$ V377Nva in the right lymph node on days 28, 32, 49, and 53 (25 μg/day). Group 3 animals (n=4 sacrificed) received injections of a mixture of pBPL+pSEM on days 1, 4, 15, and 18 (100 μg/day) in bilateral inguinal lymph nodes followed by a peptide boost consisting of SSX2$_{41-49}$ A42V (SEQ ID NO. 5) in the left lymph node and Tyrosinase$_{369-377}$ V377Nva (SEQ ID NO. 12) in the right lymph node on days 28 and 32 (25 μg/day) and a second peptide boost consisting of NY-ESO-1$_{157-165}$ L158Nva, C165V (SEQ ID NO. 6) (12.5 μg on Days 49 and 53) in the left lymph node and Melan A$_{26-35}$ A27Nva (SEQ ID NO. 11) (25 μg on Days 49 and 53) in the right lymph node. Antigen specific (Melan A, Tyrosinase, SSX2, and NY-ESO-1) interferon-γ spot forming cells per spleen were compared to a untreated naïve littermate control FIG. 4B.

Figure 4A:
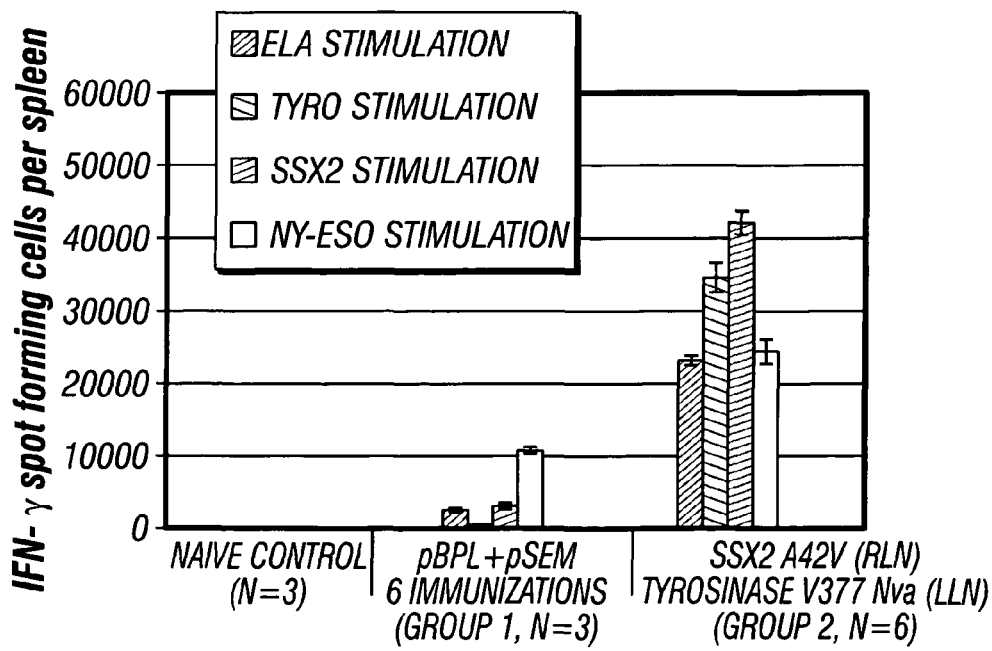
FIGS. 4A-4B. IFN-γ ELISpot analysis following a first peptide boost (FIG. 4A). ELISPOT analysis was performed on day 41. Group 1 animals (n=3 sacrificed) were primed with a plasmid mixture of pBPL+pSEM on days 1, 4, 15, and 18 (100 mg/day) followed by a boost with a plasmid mixture of pBPL+pSEM on days 28 and 32 (100 μg/day). Group 2 and 3 animals (n=6 sacrificed) were primed with a plasmid mixture of pBPL+pSEM similar to Group 1 followed by a peptide boost consisting of SSX-2$_{41-49}$ A42V (SEQ ID. NO. 5) in the left lymph node and Tyrosinase$_{369-377}$ V377Nva (SEQ ID. NO. 12) in the right lymph node on days 28 and 32 (25 μg/day). Antigen specific (Melan A, Tyrosinase, SSX-2, and NY-ESO-1) interferon-γ spot forming cells per spleen were compared to untreated naïve litternate controls (n=3)
Figure 4B:
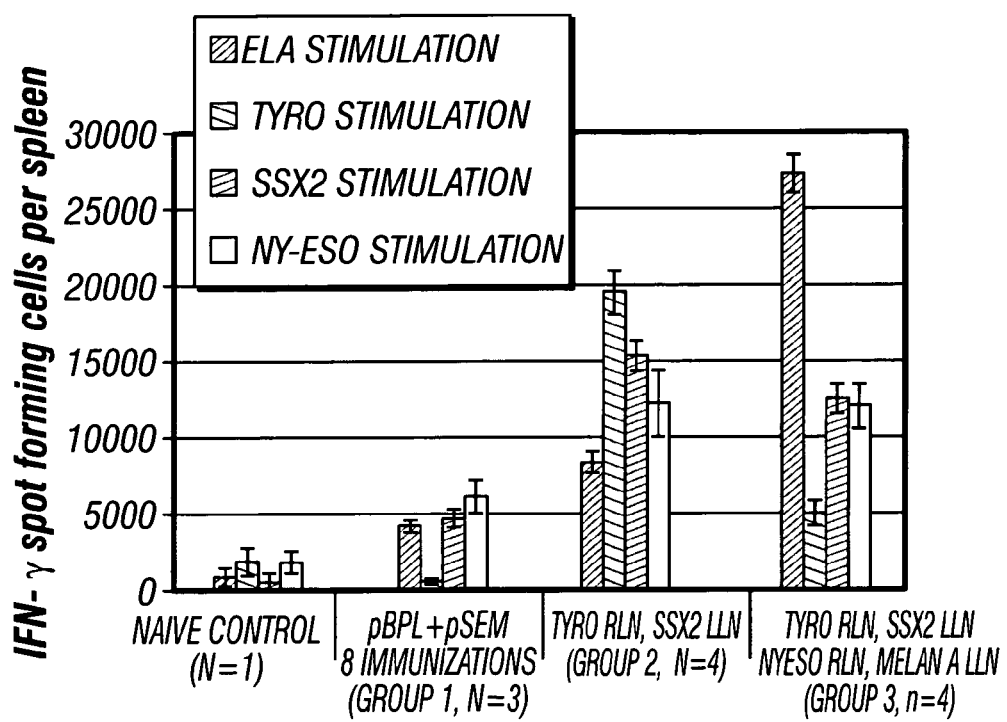

FIG. 4A shows that animals primed with the plasmid mixture and boosted with tyrosinase and SSX-2 peptides ((Group 2, n=6) demonstrated a robust tetravalent response of 2 to 8 fold higher more IFNγ producing cells than plasmid alone treated animals (Group 1, n=3). In addition, when the animals received a second boost of either the subdominant epitope peptides, SSX-2 and Tyrosinase (Group 2), or the dominant epitope peptides, NY-ESO-1 and Melan A (Group 3), a tetravalent response was maintained as compared to animals that were primed and boosted with the pSEM and pBPL plasmid combination alone (Group 1) (FIG. 4B). A more balanced immune response against all four antigens was achieved simply by boosting with the subdominant epitope analogues SSX-2 and Tyrosinase.

Overall, the data obtained from the above Examples (2-5) depict the successful generation of a tetravalent immune response in animals immunized with the NS and/or MT regimens of the present invention. A comparison of the immune responses (tetramer and IFN-γ ELISPOT analysis) in naïve animals or animals boosted with a mixture of pSEM/pBPL plasmid alone (Group 1) to animals boosted with the subdominant peptide epitopes tyrosinase and SSX-2 (Groups 2 and 3) on days 28 and 32 confirmed the successful generation of a tetravalent immune response in animals immunized with this regimen. Similar results were obtained following the second peptide boost on days 49 and 53 in where Group 3 (n=25) was boosted with the dominant epitope peptides, Melan A$_{26-35}$ (A27Nva) (SEQ ID NO. 11) and NY-ESO-1$_{157-165}$ (L158Nva, C165V) (SEQ ID NO. 6) and Group 2 (n=25) was boosted again with the sub-dominant epitope peptides Tyrosinase$_{369-377}$ (V377Nva) (SEQ ID NO. 12) and SSX-2$_{41-49}$ (A42V) (SEQ ID NO. 5).

Example 6

Generation of an Immune Response to Human Melanoma

The carboxy-fluorescein diacetate, succinimidyl ester (CFSE) assay provides a simple and sensitive means for fluorescently labeling cells. This method allows for the analysis of antigen specific and non-specific T cell proliferation.

The CFSE methodology was employed to evaluate the efficacy of the immunization protocols. Animals, selected based on their tetramer levels, were analyzed for their ability to clear human CFSE labeled melanoma tumor cells in the lung.

On day 61, two animals from each group (Group 1, 2, and 3) were selected based on high tetramer levels, and injected intravenously with CFSE labeled tumor cells. More precisely, human 624.38 cultured melanoma tumor cells (10×10$^6$), expressing all four tumor associated antigens for SSX-2, NY-ESO-1, Tyrosinase, and Melan A, were stained with CFSEhi (Vybrant CFDA SE cell tracer kit, Molecular Probes) fluorescence (1.0 μM for 15 minutes) and co-injected intravenously into Group 1, 2, or 3 immunized mice (N=2/group) or into naïve HHD mice (N=2) with an equal ratio of 624.28 HLA-A2 negative control cells stained with CFSElo fluorescence (0.1 μM). Animals received a second injection of target cells two hours later.

The specific elimination of human target cells was measured on day 62, approximately 14 hours after the injection of target cells, by sacrificing the mice, removing lung tissue, and measuring CFSEhi relative to CFSElo fluorescence (FL1 channel) by flow cytometry. The formula used to calculate the percent specific lysis is shown below.

[(1−% CFSEhi/% CFSElo) in immunized−(1−% CFSEhi/% CFSElo) in naïve]×100

Figure 5:
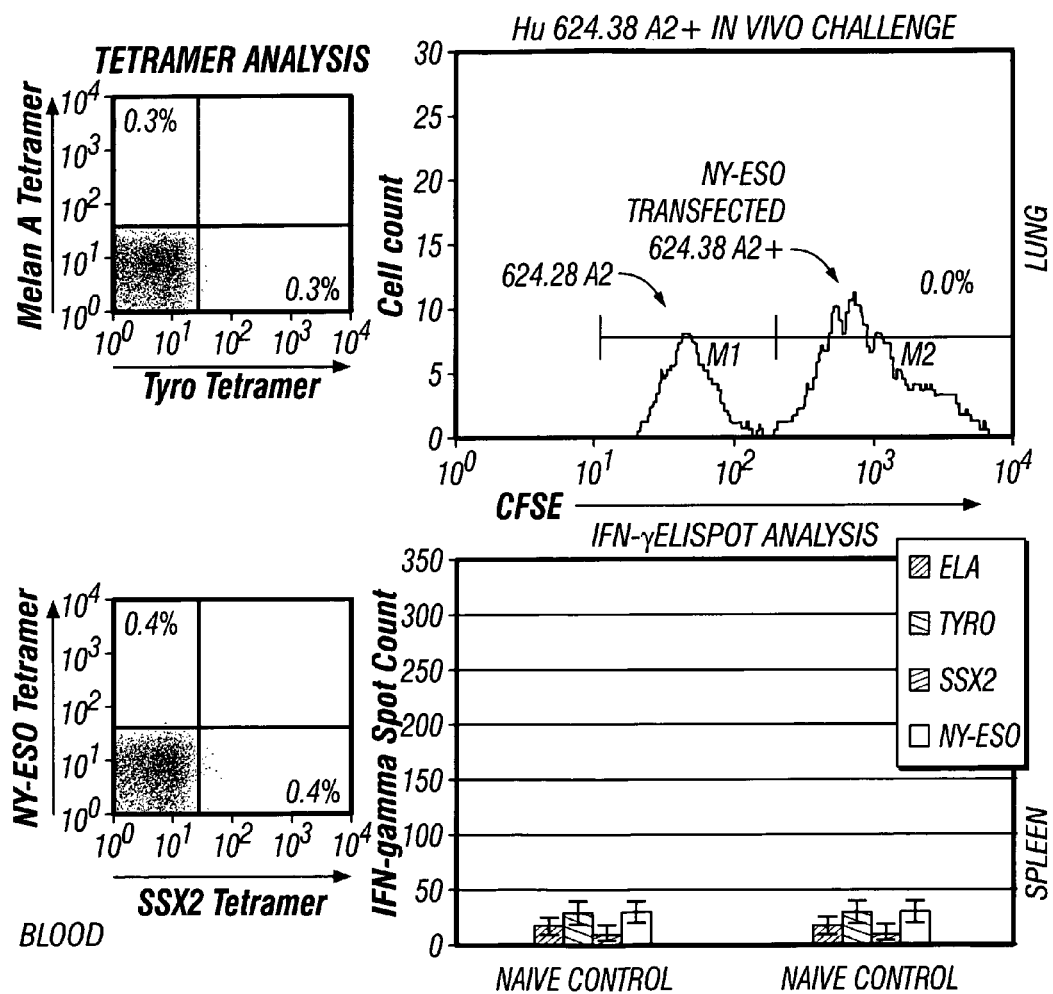
FIG. 5. Depicts tetramer levels, IFN-γ ELISPOT and carboxy-fluorescein diacetate, succinimidyl ester (CFSE) histograms from in vivo studies where animals were challenged with human melanoma tumor cells expressing all four tumor associated antigens. Naïve control (top left panel); two animals with tetravalent immunity (top right panel and lower left panel); and an animal with a monovalent response to Melan A (lower right panel).
Figure 5:
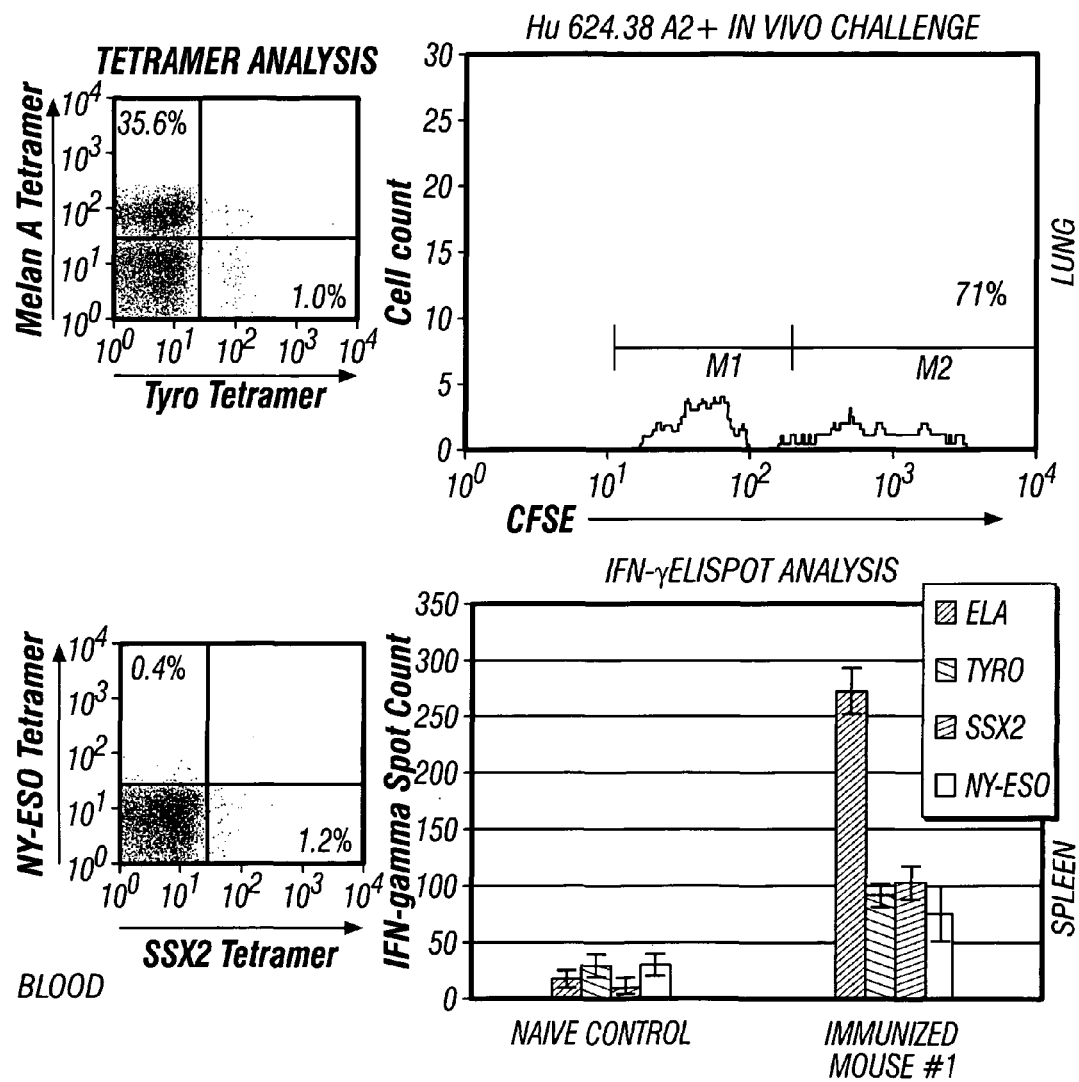
Figure 5:
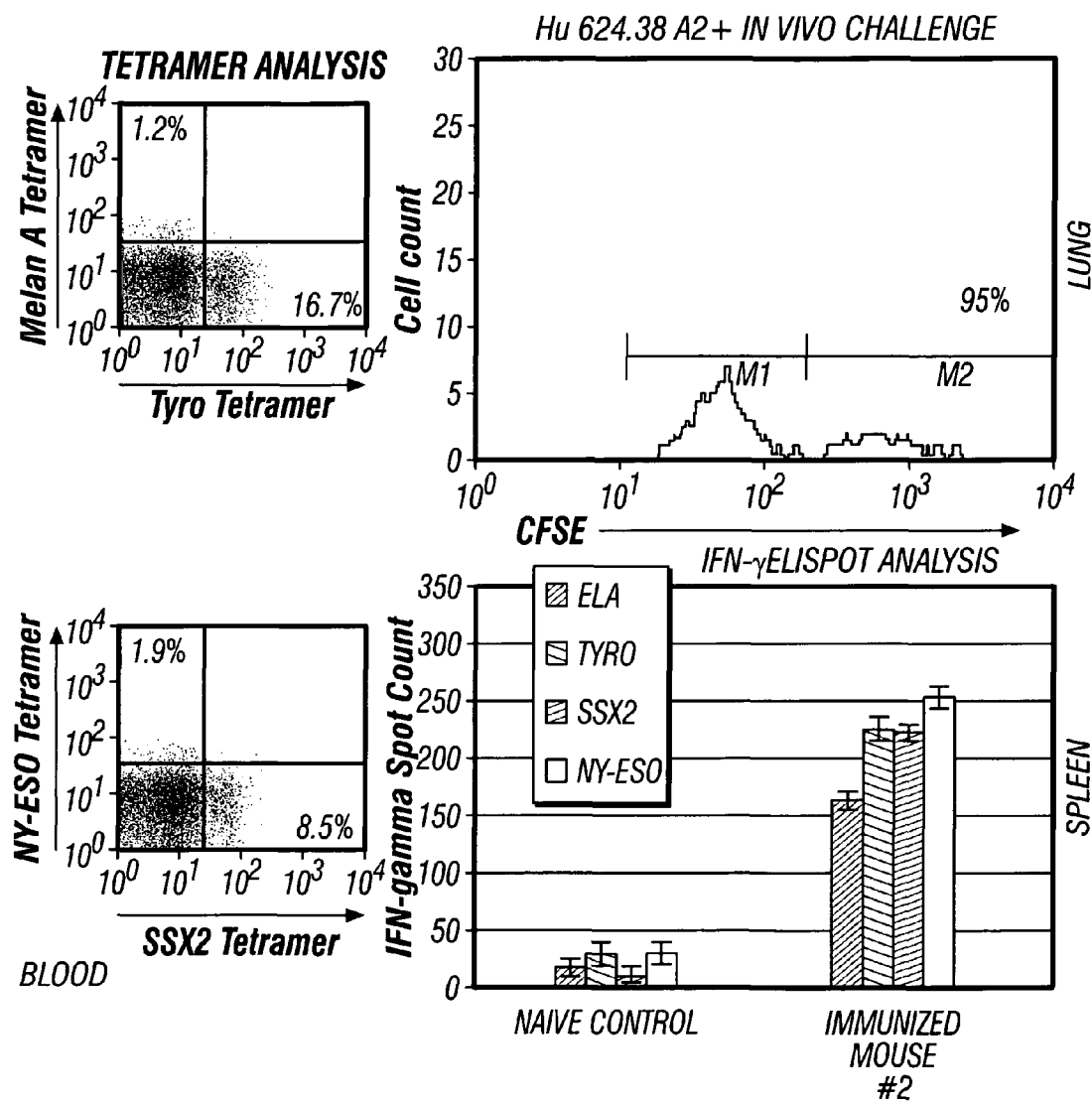
Figure 5:
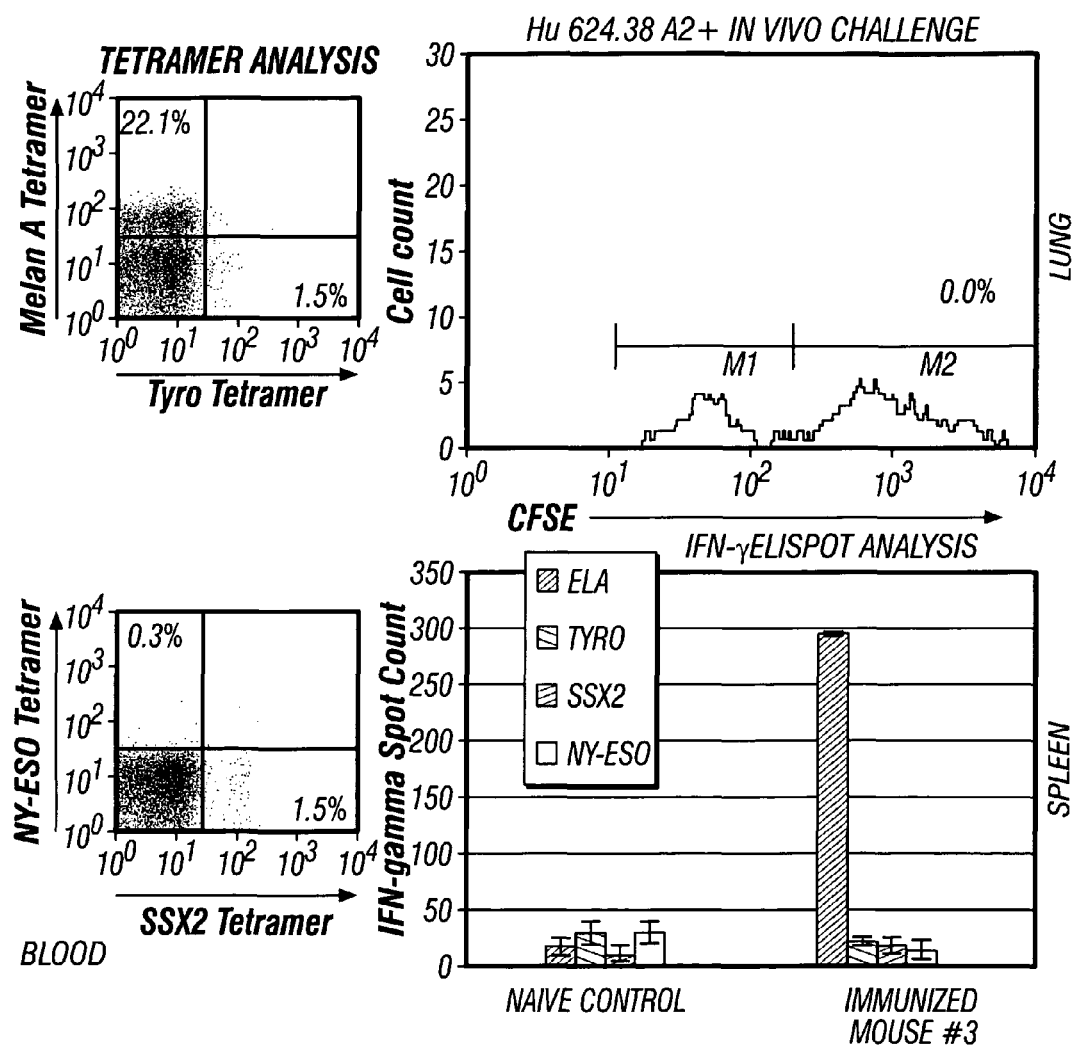

FIG. 5 shows tetramer levels, IFNγ ELISPOT results, and two peak CFSE histograms from a naïve control (top left panel), two animals with tetravalent immunity (top right and lower left panel), and an animal with a monovalent response to Melan A (lower right panel). As expected, the naïve control animal was unable to clear the target cells as demonstrated by the maintenance of an equal ratio of both histogram peaks as was the case in the animal demonstrating the monovalent immune response. On the other hand, animals displaying an immune response to all four antigens were much more capable of clearing the human melanoma tumor target cells with 71% and 95% specific lysis.

Example 7

Generation of an Immune Response by a Original Vs. Expanded Protocol

It was assessed whether immunization with the plasmids D1 (pRP12) and D2 (pBPL) could induce a tetravalent response in HHD-1 mice against four tumor-associated antigens: $PSMA_{788-297}$ (SEQ ID NO. 4), $PRAME_{425-433}$ (SEQ ID NO. 3), $SSX-2_{41-49}$ (SEQ ID NO. 1), and $NY-ESO-1_{157-165}$ (SEQ ID NO. 2).

Two different boosting strategies were tested with regard to their ability to enhance the desired immune responses. The first approach (the "original" protocol) utilized a single injection of each peptide during the boosting procedure. The second approach (the "expanded" protocol) tested two injections of each peptide. Three dosage levels of each peptide (low, mid, and high) were tested in an effort to determine a dose-response relationship and to help define the optimum peptide concentration.

Six groups of 10 female HHD-1 animals/group were immunized with plasmids D1 and D2 injected directly into the bilateral inguinal lymph nodes. Animals from Groups 1-3 were boosted using the "original" protocol, and Groups 4-6 animals were boosted using the "expanded" protocol.

Animals on the "original protocol" (Groups 1-3, n=10 per group) received 4 injections of D1 (pRP12 (SEQ ID NO. 21)) plasmid (100 μg per dose) in the right inguinal lymph node and 4 injections of D2 (pBPL (SEQ ID NO. 20)) plasmid (100 μg/dose) in left inguinal lymph node on days 1, 4, 15 and 18. This was followed by a boost with $PSMA_{288-297}$ (I297V) (SEQ ID NO. 8) in the right lymph node and $SSX-2_{41-49}$ (A42V) (SEQ ID NO. 5) in the left lymph node on day 29, and with $PRAME_{425-433}$ (L426Nva, L433Nle) (SEQ ID NO. 7) in the right lymph node and $NY-ESO-1_{157-165}$ (L158Nva, C165V) (SEQ ID NO. 6) in the left lymph node on day 32.

Animals on the "expanded protocol" (Groups 4-6, n=10 per group) received 4 injections of D1 (pRP12 (SEQ ID NO. 21)) plasmid (100 μg/dose) in right inguinal lymph node and D2 (pBPL (SEQ ID NO. 20)) plasmid (100 μg/dose) in left inguinal lymph node on days 1, 4, 15 and 18. The animals were subsequently boosted with $PSMA_{288-297}$ (I297V) (SEQ ID NO. 8) in the right lymph node and $SSX-2_{41-49}$ (A42V) (SEQ ID NO. 5) in the left lymph node on days 29 and 32 and with $PRAME_{425-433}$ (L426Nva, L433Nle) (SEQ ID NO. 7) in the right lymph node and $NY-ESO-1_{157-165}$ (L158Nva, C165V) (SEQ ID NO. 6) in the left lymph node on days 43 and 46.

Figure 6:
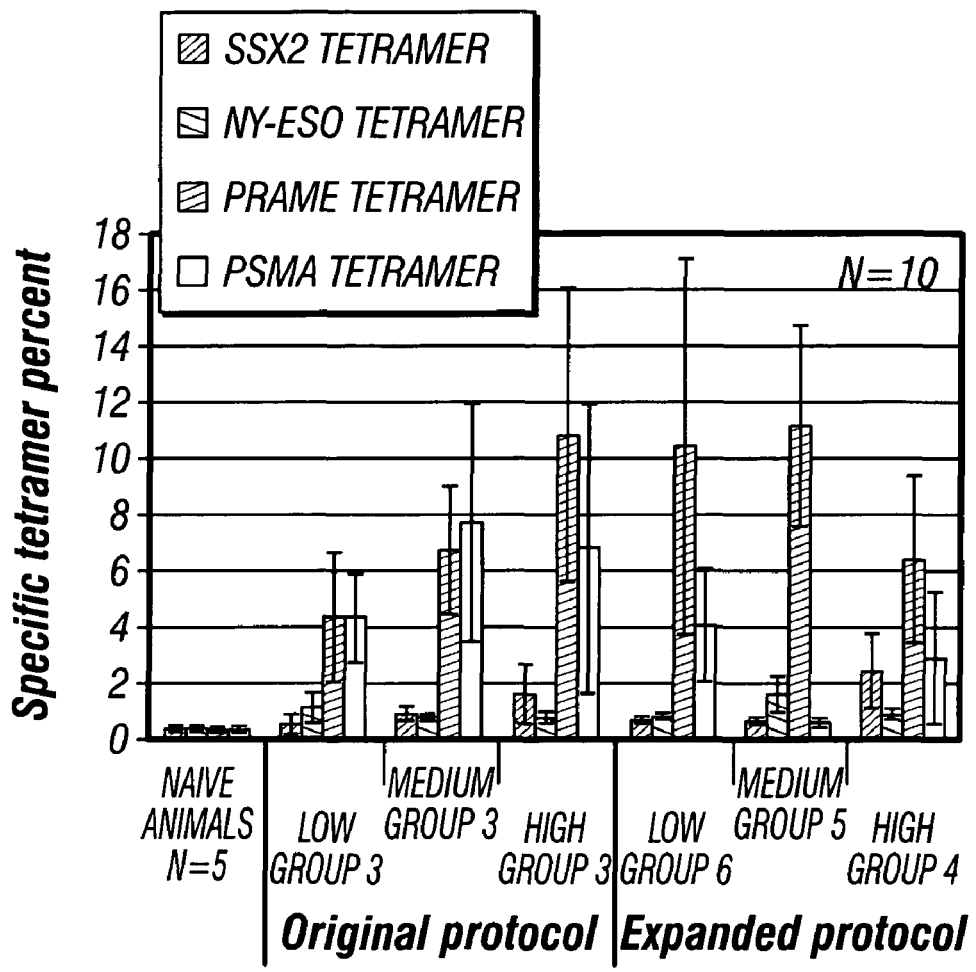
FIG. 6. Tetramer analysis of the "original" versus the "expanded" protocol. Animals were injected based on a "original protocol" (Groups 1-3) or an "expanded protocol" (Groups 4-6) with 4 injections of D1 (pRP12) plasmid (4 mg/ml) in the right inguinal lymph node and 4 injections of D2 (pBPL) plasmid (4 mg/ml) in left inguinal lymph node. Animals were subsequently boosted with PSMA, SSX-2, PRAME and NY-ESO-1 peptides. Animals were primed with D1 (pRP12) plasmid and D2 (pBPL) plasmid (4 mg/ml) on days 1, 4, 15, and 18, followed by boosting with PSMA$_{788-297}$ (I297V) peptide (RLN) (SEQ ID. NO. 8) and SSX-2$_{41-49}$ (A42V) peptide (LLN) (SEQ ID. NO. 5) on days 29 and 31 for the original protocol; and boosting with PRAME$_{425-433}$ (L426Nva, L433Nle)) peptide (RLN) (SEQ ID. NO. 7) and NY-ESO-1$_{157-165}$ (L158Nva, C165V) peptide (LLN) (SEQ ID. NO. 6) on days 42, 45 for the expanded protocol (Groups 4-6). Values represent average+/−SEM from individual animals after peptide boost and are compared to untreated naïve littermate controls (n=5).

Blood was collected from each group in both protocols, 7 days following the last peptide boost, and $CD8^+$ T cell analysis was performed using a tetramer assay (FIG. 6). Responses were compared to naïve littermate control mice (n=5). SSX-2, NY-ESO-1, FRAME, and PSMA tetramer values are shown comparing the original and expanded protocols comprised of low, medium and high peptide boosts in FIG. 6.

Figure 7:
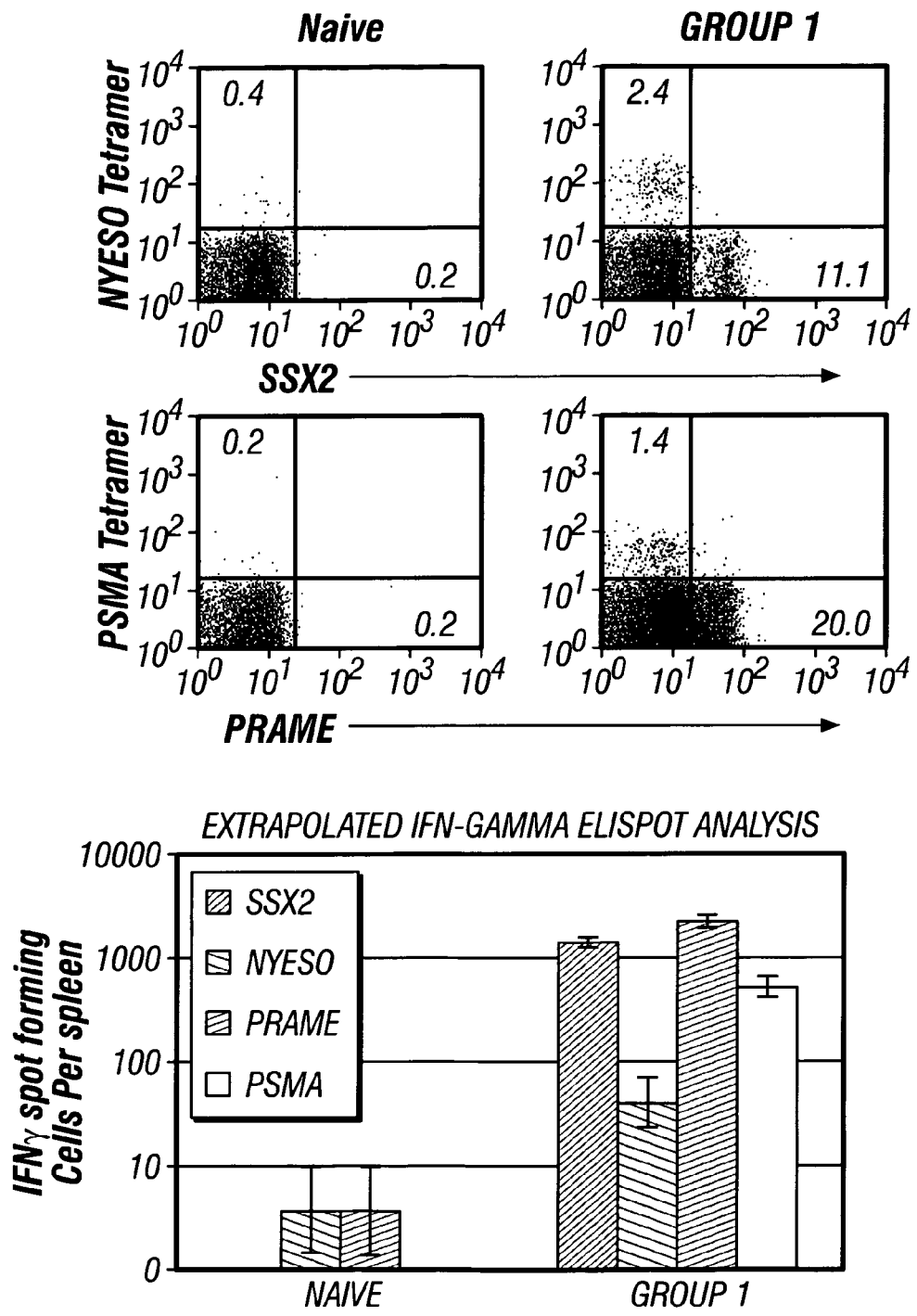
FIG. 7. Tetravalent immune response from a representative animal in Group 1 (FIG. 6). Following plasmid priming, PSMA peptide (25 μg) and PRAME peptide (20 μg) were injected into the right lymph node. Twenty-five micrograms each of SSX-2 and NY-ESO-1 peptides were injected into the left lymph node. Data shown measures immune response by both tetramer and ELISpot assays.

Animals primed with four injections of D1 and D2 plasmid and subsequently boosted with the peptide analogues PSMA, PRAME, NY-ESO-1, and SSX-2 demonstrated immune responses to all four antigens, as assessed by tetramer analysis (FIG. 6), that was dominated by immune responses to FRAME and PSMA. In addition, tetravalent immune responses elicited by this immunization strategy was demonstrated in individual animals (FIG. 7). The responses were observed to be independent of boosting regimen (original vs. expanded). In addition, no apparent dose-response was observed, although the high dose group (25 μg peptide) in each therapeutic protocol yielded the highest response rate. Furthermore, the tetramer data indicated that FRAME and PSMA were the dominant epitopes following immunization of the animals.

Example 8

IFN-Γ ELISPOT of an Immune Response by a Original Vs. Expanded Protocol

To confirm the results observed with the tetramer assay, an interferon-γ (IFN-γ) ELISpot assay was conducted. Animals from each group in Example 7, were sacrificed 22 days following the last peptide boost and spleens were removed for IFN-γ ELISPOT analysis.

Spleens were isolated on day 68 from euthanized animals and the mononuclear cells, after density centrifugation (Lympholyte Mammal, Cedarlane Labs, Burlington, N.C.), were resuspended in HL-1 medium. Splenocytes ($3 \times 10^5$ or $1.5 \times 10^5$ cells per well) were incubated with 10 μg of $PSMA_{288-297}$ (SEQ ID NO. 4), $PRAME_{425-433}$ (SEQ ID NO. 3), $SSX-2_{41-49}$ (SEQ ID NO. 1), or $NY-ESO-1_{157-165}$ (SEQ ID NO. 2), natural peptide in triplicate wells of a 96 well filter membrane plates (Multi-screen IP membrane 96-well plate, Millipore, Mass.). Samples were incubated for 72 hours at 37° C. with 5% $CO_2$ and 100% humidity prior to development. Mouse IFN-γ coating antibody (IFN-γ antibody pair, U-CyTech Biosciences, The Netherlands) was used as coating reagent prior to incubation with splenocytes, followed by the accompanied biotinylated detection antibody. GABA conjugate and proprietary substrates from U-CyTech Biosciences were used for IFN-γ spot development. The CTL response in immunized animals was measured 24 hours after development on the AID International plate reader using ELISpot Reader software version 3.2.3 calibrated for IFN-γ spot analysis.

The IFNγ ELISPOT results shown in FIG. 7 correlate well with the tetramer data (FIG. 6) and confirm a robust immune response to $PRAME_{475-433}$ (SEQ ID NO. 3), $PSMA_{288-433}$ (SEQ ID NO. 4), $SSX-2_{41-49}$ (SEQ ID NO. 1), and $NY-ESO-1_{157-165}$ (SEQ ID NO. 2) elicited by the "original" therapeutic protocol. The "expanded" protocol did not appear to offer any apparent advantage over the "original" protocol as measured by IFN-γ ELISPOT analysis.

Example 9

Tetravalent Immune Response Generated by the PP/NS Therapeutic Regimen

It was assessed whether a tetravalent immune response can be elicited by first boosting with the subdominant epitopes PSMA and SSX-2 followed by boosting with the dominant epitopes PRAME and NY-ESO-1. A representative animal from Group 1 ("original protocol"; high dose) received 4 injections of D1 (pRP12 (SEQ ID NO. 21)) plasmid (100 μg/dose) in the right inguinal lymph node and 4 injections of D2 (pBPL (SEQ ID NO. 20)) plasmid (100 mg/dose) in left inguinal lymph node on days 1, 4, 15 and 18. This was followed by a boost with peptides, $PSMA_{288-297}$ (I297V) (SEQ ID NO. 8) in the right lymph node (25 μg) and $SSX-2_{41-49}$ (A42V) (SEQ ID NO. 5) in the left lymph node (25 μg) on day 29 and with $PRAME_{425-433}$ (L426Nva, L433Nle) (SEQ ID NO. 7) in the right lymph node (20 μg) and $NY-ESO-1_{157-165}$ (L158Nva, C165V) (SEQ ID NO. 6) in the left lymph node (25 μg) on day 32. The data (FIG. 8) shows a tetravalent immune response as measured by two separate assays, tetramer and ELISpot analyses.

Example 10

$^{51}$Chromium-Release Assay Measuring CTL Activity to PRAME, PSMA, NY-ESO and SSX-2

CTL response to $PRAME_{425-433}$ (SEQ ID NO. 3), $PSMA_{288-297}$ (SEQ ID NO. 4), $NY-ESO-1_{157-165}$ (SEQ ID NO. 2) and $SSX-2_{41-49}$ (SEQ ID NO. 1), using $^{51}Cr$ cytotoxicity assays, after DNA prime and peptide boost and one round of in vitro stimulation in immunized mice was assessed. CTLs were generated by ex vivo stimulation of splenocytes harvested from immunized mice (N=6) 22 days after the completion of the peptide immunization regimens.

Briefly, mice were sacrificed and the spleens were removed. The spleens were homogenized and the cell suspension was strained to yield a single-cell suspension. Quantities of $5 \times 10^6$ cells/well were plated in 24 well tissue culture plates and $1.5 \times 10^6$ peptide-pulsed, γ-irradiated and LPS (lipopolysaccharide) blasted B cells were added to each well. Mouse recombinant IL-2 was also added at a concentration of 1 ng/ml. The cells were incubated for 4 days for the PRAME group and 6 days for each of the PSMA, SSX-2 and NY-ESO-1 groups.

After the ex vivo stimulation, CTLs were collected from the plates, washed, and plated into 96 well U-bottom microtiter assay plates at concentrations of $10^6$, $3.3 \times 10^5$, and $1.1 \times 10^5$ cells/well in a total of 100 μL per well. To assess peptide specific lysis, T2 cells were labeled with $^{51}$Cr and pulsed with 20 μg/mL of each peptide (SSX-2, NY-ESO-1, PSMA, or PRAME) at 37° C. for 1.5 hours. After the incubation, the cells were washed and resuspended. Ten thousand $^{51}$Cr-labeled and peptide-pulsed T2 cells were added to each well. The cells were then incubated at 37° C. for 4 hours.

Figure 8:
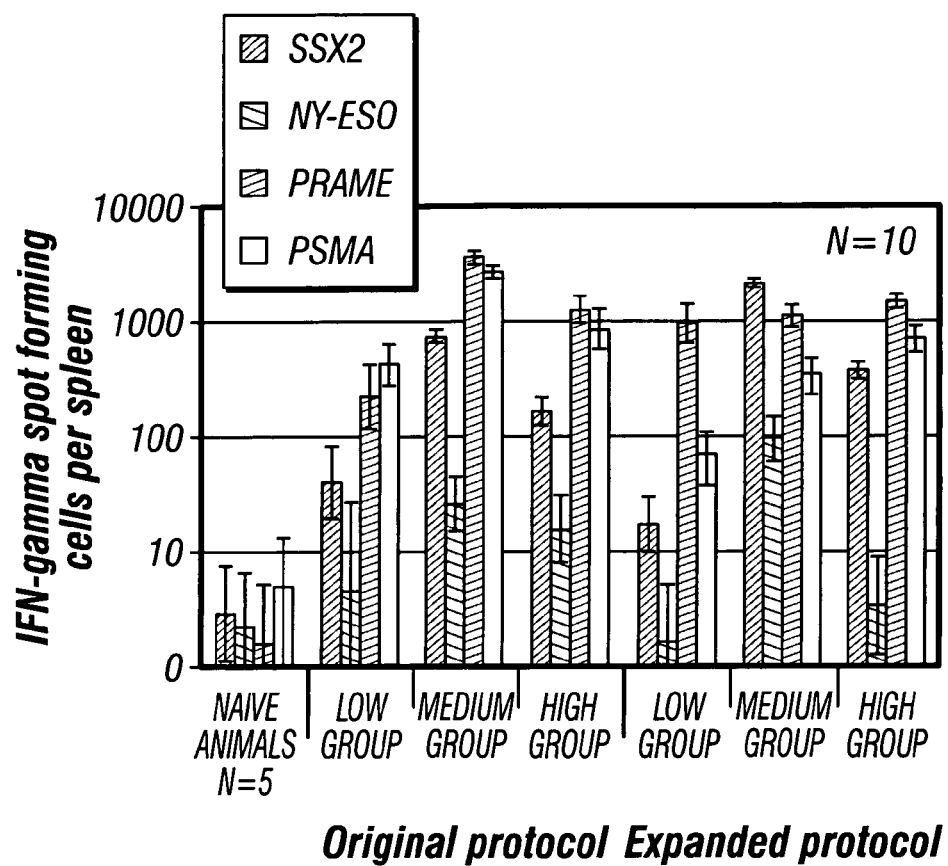
FIG. 8. IFN-γ ELISPOT analysis of the "original" versus the "expanded" protocol. Total antigen specific (SSX-2, NY-ESO-1, PRAME, and PSMA) interferon-γ spot forming cells per spleen are shown comparing the "original" and "expanded" protocols comprised of low, medium and high peptide boosts. IFN-γ ELISpot analysis was performed in triplicate, values represent average+/−SEM after peptide boost. Splenocytes (3×10$^5$ cells per well) were stimulated, ex vivo in 96 well ELISpot plates, with peptide (SSX-2, NY-ESO-1, PRAME, and PSMA) at a concentration of 10 μg/ml for 72 hrs. Values are extrapolated from total nucleated splenocytes and normalized per spleen from each animal.

After incubation, supernatants were harvested and the cytolytic activity was measured in triplicate samples using a gamma counter. The corrected percent lysis was calculated for each concentration of effector cells, using the mean cpm for each replicate of wells (FIG. 8). Percent specific lysis was calculated using the following formula: Percent release=100×(Experimental release−spontaneous release)/(Maximum release−spontaneous release). Data are presented as follows: the x-axis shows the effector to target ratio; the γ-axis shows the corresponding percentage specific lysis.

The results (FIG. 8) show $^{51}$Chromium release assay (CRA) data for CTL from each group against T2 cells pulsed with PRAME$_{415}$-433 (SEQ ID NO. 3) (panel 1), PSMA$_{288-297}$ (SEQ ID NO. 4) (panel 2), NY-ESO-1$_{157-165}$ (SEQ ID NO. 2) (panel 3), or SSX-2$_{41-49}$ (SEQ ID NO. 1) (panel 4) peptides as targets. Specific lysis values were compared to un-pulsed T2 control cells. Given that the ELISA analysis (data not shown) indicated that immunogenicity of the PRAME group is very strong and to avoid antigen-induced cell deaths, the CRA for the PRAME group was pursued following a 4-day IVS protocol. The CRA was done following 6 days IVS for the other peptide groups. It was found that after in vitro re-stimulation, T cells isolated from all immunized groups specifically killed T2 cells pulsed with peptide in contrast with those from naïve animals. CTL responses to PRAME$_{425-433}$ (SEQ ID NO. 3), PSMA$_{288-297}$ (SEQ ID NO. 4), SSX-2$_{41-49}$ (SEQ ID NO. 1) and NY-ESO-1$_{157-165}$ (SEQ ID NO. 2) were induced in all groups, as assessed by $^{51}$Cr cytotoxicity assays. These CTLs had no effect on T2 control cells without peptide. The results demonstrated that T2 target cell lysis by the CTLs isolated from immunized mice is peptide specific. Compared to the "original" protocol, the "expanded" protocol offered no significant enhancement of the lysis percentage, further suggesting that the "original" protocol is sufficient for eliciting a substantial immune response against multiple antigens. Furthermore, due to the increased sensitivity of the CRA assay, the specific NY-ESO-1 responses from each group were more prevalent as compared to the tetramer and ELISPOT assays.

Example 11

Employing Multiple Therapeutic Cycles

It was assessed whether immunization with the plasmids D1 (pRP12 (SEQ ID NO. 21)) and D2 (pBPL (SEQ ID NO. 20)) could maintain robust immune responses in HHD-1 mice against four tumor-associated antigens: PSMA$_{288-297}$ (SEQ ID NO. 4), PRAME$_{425-433}$ (SEQ ID NO. 3), SSX-2$_{41-49}$ (SEQ ID NO. 1), and NY-ESO-1$_{157-165}$ (SEQ ID NO. 2) after more than one cycle of a therapeutic regimen of the present invention.

Male and female HHD-1 mice were immunized with plasmids D1 and D2 injected directly into the bilateral inguinal lymph nodes followed by peptide boost with PSMA$_{288-297}$ (SEQ ID NO. 4), PRAME$_{425}$-433 (SEQ ID NO. 3), SSX-2$_{41-49}$ (SEQ ID NO. 1), and NY-ESO-1$_{157-165}$ (SEQ ID NO. 2). Animals received 4 injections of D1 (pRP12 (SEQ ID NO. 21)) plasmid in the right inguinal lymph node and 4 injections of D2 (pBPL (SEQ ID NO. 20)) plasmid in left inguinal lymph node on days 1, 4, 15 and 18. This was followed by a boost with PSMA$_{288-297}$ (I297V) (SEQ ID NO. 8) in the right lymph node and SSX-2$_{41-49}$ (A42V) (SEQ ID NO. 5) in the left lymph node on day 29, and with PRAME$_{425-433}$ (L426Nva, L433Nle) (SEQ ID NO. 7) in the right lymph node and NY-ESO-1$_{157-165}$ (L158Nva, C165V) (SEQ ID NO. 6) in the left lymph node on day 32. The second prime (plasmid)/boost (peptide) therapeutic cycle was repeated following a rest period of 14 days.

Animals were injected with plasmid vehicle (N=16 animals/group); peptide vehicle (N=16 animals/group); plasmid (400 μg total dose) at high dose (N=16 animals/group); peptide (25 μg total dose) at high dose (N=16 animals/group); plasmid (400 μg total dose) at high dose+peptide (5 μg total dose) at low dose (N=16 animals/group); plasmid at low dose (100 μg total dose)+peptide (25 μg total dose) at high dose (N=14 animals/group); or plasmid (400 μg total dose) at high dose+peptide (25 μg total dose) at high dose (N=16 animals/group) and compared to the naïve control group N=7 animals/group.

Figure 9:
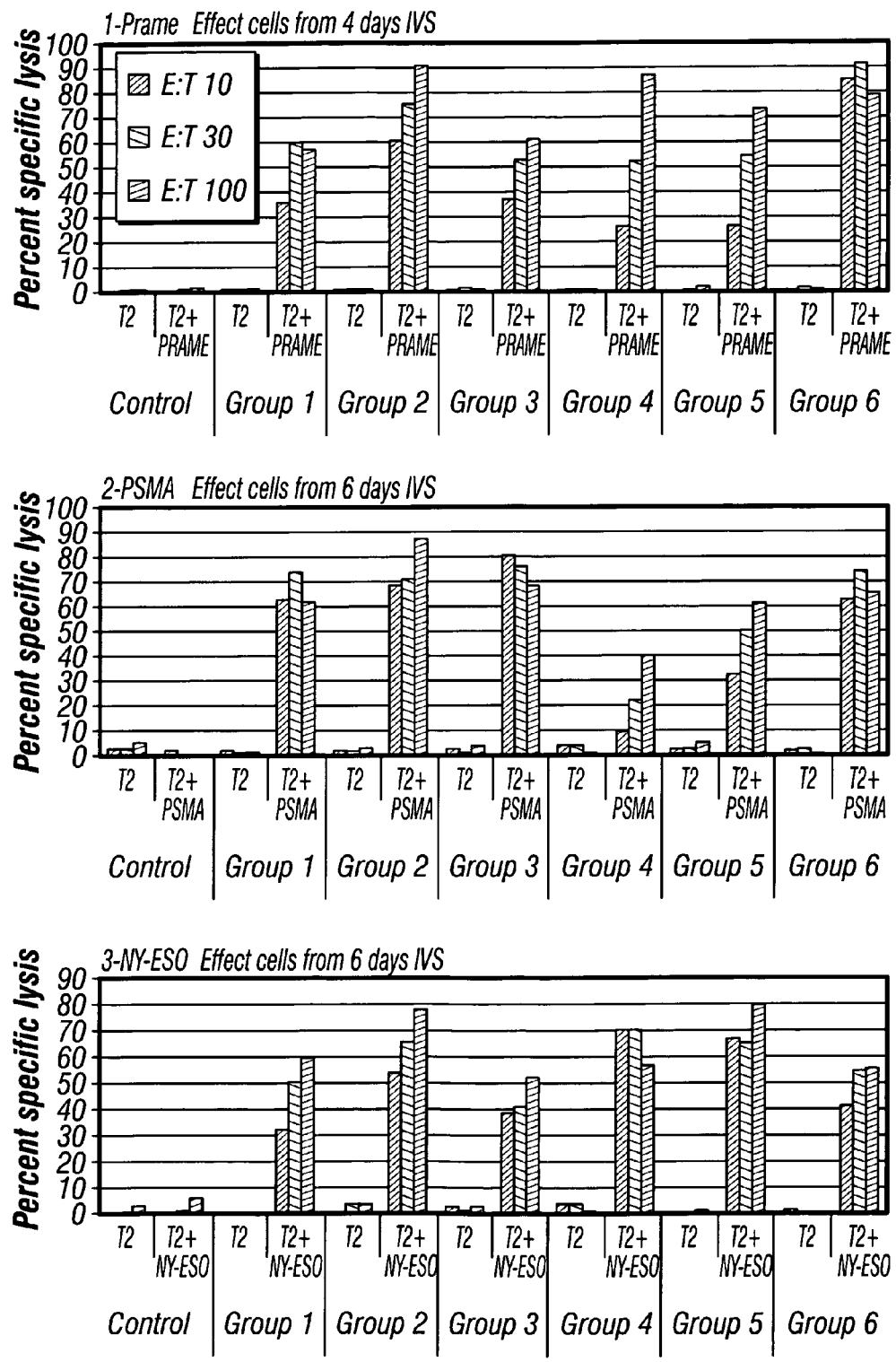
FIG. 9. $^{51}$Cr cytotoxicity assays.
Figure 9:
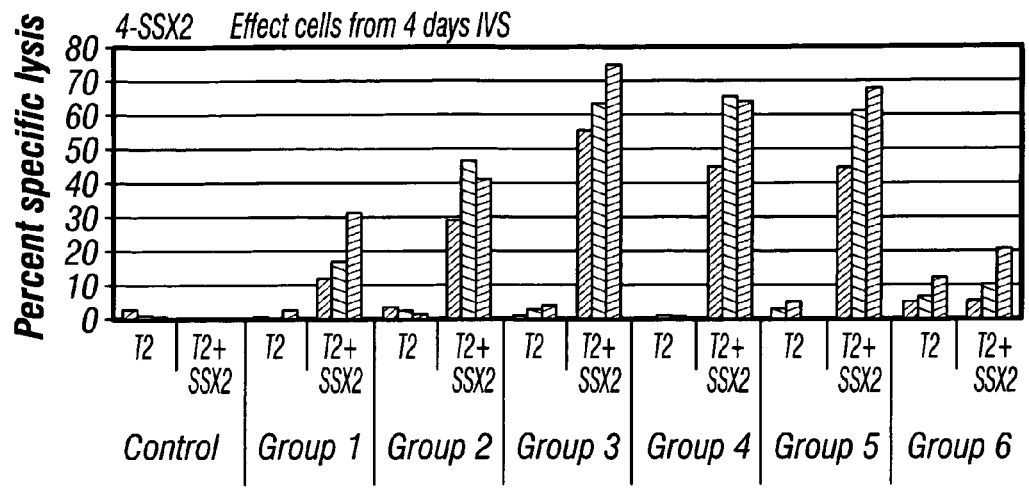
Figure 10:
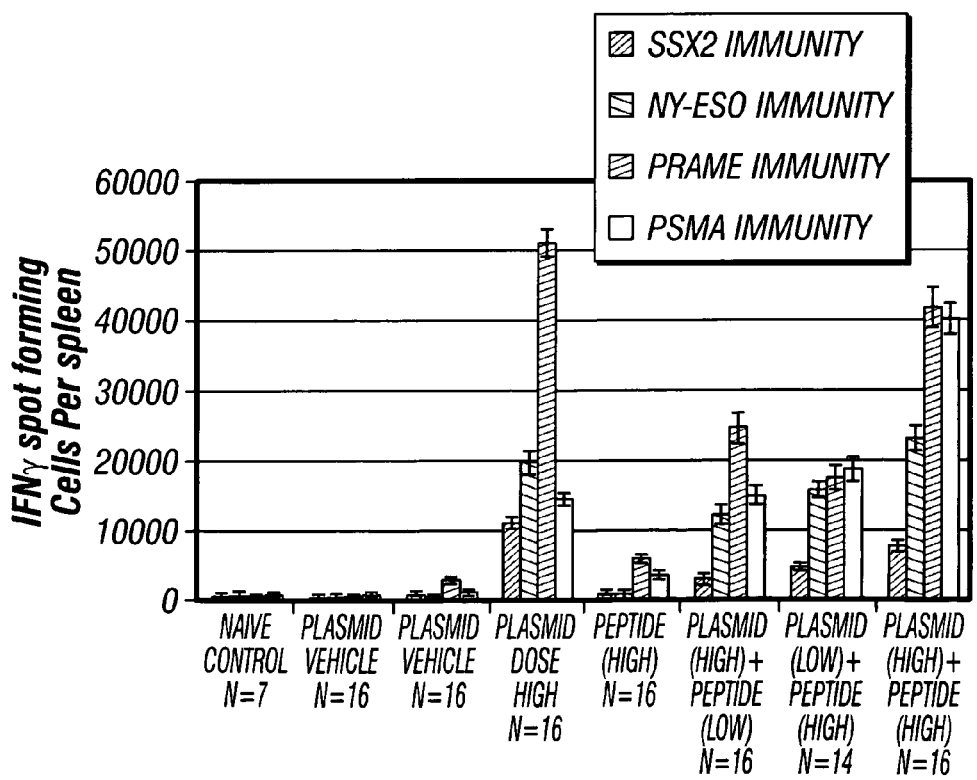
FIG. 10. Immune response elicited by two cycles of therapeutic regimens of the PP(PRAME and PSMA) regimen and the NS (NY-ESO-1 and SSX-2) regimen showing peptide dominance of PRAME.

Animals from each group, were sacrificed 14 days following the last peptide boost and spleens were removed for IFN-γ ELISPOT analysis (FIG. 9).

The data show that animals can generate robust immune responses following two cycles of therapeutic regimens of the PP (FRAME and PSMA) regimen and the NS (NY-ESO-1 and SSX-2) regimen.

Overall, the data obtained in Examples 7-11 shows significant T cell, but no significant antibody responses, following the PP/NS therapeutic immunization protocol. No peptide-specific antibodies were detected in the serum of immunized mice using an ELISA assay following one complete therapeutic cycle (data not shown). Furthermore, antigen-specific T cell responses encompassed effector and memory T cells (IFNγ cytokine producing, cytolytic and tetramer binding) with PRAME and PSMA leading and SSX-2 and NY-ESO-1 trailing in magnitude. In addition the results indicate, that while expanding the therapeutic protocol may not achieve higher T cell immunity, reordering of subdominant relative to the dominant peptides within a therapeutic cycle may be needed to improve on immunity against NY-ESO-1 or any other subdominant epitope.

PSMA$_{288-297}$ Analogs

Many features regarding the variety of embodiments and aspects of analog design are disclosed above, either generally or as applied to particular epitopes. It is to be understood that such disclosure is also applicable to this and subsequent epitopes. Explicit restatement of such disclosure will be minimized for the sake of brevity.

Some embodiments relate to analogs of the MHC class I-restricted T cell epitope PSMA$_{288-297}$ GLPSIPVHPI (SEQ ID NO. 4), polypeptides comprising these analogs that can be processed by pAPC to present the epitope analogs, and nucleic acids that express the analogs. The analogs can have similar or improved immunological properties compared to the wild-type epitope. Evidence validating the presentation of this epitope by human cancer cells is presented in Example 32 of application Ser. Nos. 11/455,278 and 11/454,633, each of which is hereby incorporated by reference in its entirety.

One embodiment relates to methods to derivatize and improve analogs of $PSMA_{288-297}$, along with specific sequences that encompass substitutions. The analogs can contain at least one substitution, but can have multiple substitutions comprising standard or non-standard amino acids singly or in various combinations. The analogs can result in peptides with retained or improved properties.

Embodiments relate to families of one or more peptides of 9 or 10 amino acids in length related by sequence to amino acids 288-297 of the human PSMA.

Analog Design

In some embodiments the $PSMA_{288-297}$ analog can contain substitutions of the sequence GLPSIPVHPI (SEQ ID NO. 4). Reference to binding motif data indicates that the P2 anchor residue can make the largest individual contribution to affinity of any position in an A2.1-restricted epitope. In this case, the amino acid at the P2 position is the optimally preferred leucine. The PO anchor residue, isoleucine, is favorable. In vitro binding studies using the T2 cell assay system (not shown) have indicated that the native peptide has generally superior binding characteristics, particularly as compared to the SSX-2 and NY-ESO-1 epitopes. The epitope exhibited significant binding at relatively low concentrations, although this was paired with a relatively shallow rise toward saturation. Consistent with the favorable results obtained with Nle and Nva for the SSX-2 and NY-ESO-1 epitopes discussed above, Nle and Nva also can be successfully used for the instant PSMA epitope. Finally, even similar binding characteristics, if paired with alterations that help circumvent whatever tolerance to the epitope may exist, can increase the effective immunogenicity of the peptide. In the transgenic mouse model, the native peptide is poorly immunogenic which may reflect tolerance to the epitope; the region of PSMA from which this epitope is derived is identical between mouse and human PSMA.

1. N-Terminus Proximal Primary Anchor Modification (P2)

As noted above, although the native residue at the P2 position of this epitope is generally the optimal residue among genetically encoded amino acids. The effect of substituting other preferred or bulky hydrophobic residues were examined for potential improvement of binding, tolerance breaking and cross-reactive immunity. Exemplary substitutions can include Met, Ile, Gln, Val, Nva, Nle, and aminobutyric acid (Abu).

2. N-Terminal Secondary Anchor Modification (P1)

The N-terminal secondary anchor is the first amino acid at the N-terminus. The native Gly is only marginally preferred at this position. Various observations show that amino acids with potential to improve the epitope include Ala, Ser, Abu and sarkosine (Sar, that is, N-methylglycine).

3. C-Terminal Primary Anchor Modification (PO)

The native Ile at this position is generally a preferred but not optimal residue. Substitution at this position can improve binding. Exemplary substitutions can include Val, Leu, Nva, and Nle.

4. Secondary Anchors and TCR Exploration

The penultimate position (PO-1) can serve both as a secondary anchor and a TCR interacting position. Substitution of Ala, Leu, Ser, or Thr can have a primary effect on TCR interaction, though it can also contribute to improved binding.

P3 is another position that can effect both binding and immunogenicity. Substitution of Trp at this position can improve both.

Further embodiments relate to combinations of substitutions at multiple positions in order to combine, synergize, and counteract the various effects obtained with the single substitutions.

$PRAME_{425-433}$ Analogs Many features regarding a variety of embodiments and aspects of analog design are disclosed above, either generally or as applied to particular epitopes. It is to be understood that such disclosure is also applicable to this and subsequent epitopes. Explicit restatement of such disclosure will be minimized for the sake of brevity.

Embodiments include analogs of the MHC class I-restricted T cell epitope $PRAME_{425-433}$, SLLQHLIGL (SEQ ID NO. 3), polypeptides comprising these analogs that can be processed by pAPC to present the epitope analogs, and nucleic acids that express the analogs. The analogs can have similar or improved immunological properties compared to the wild-type epitope.

One embodiment relates to methods to derivatize and improve analogs of $PRAME_{425-433}$, along with specific sequences that encompass substitutions. The analogs can contain at least one substitution, but can have multiple substitutions comprising standard or non-standard amino acids singly or in various combinations. The analogs can result in peptides with retained or improved properties.

Some embodiments relate to families of one or more peptides of 9 or 10 amino acids in length related by sequence to amino acids 425-433 of the human PRAME sequence.

Analog Design

Some embodiments relate to analogs of the $PRAME_{425-433}$ which can contain substitutions of the sequence SLLQHLIGL (SEQ ID NO. 3). Reference to binding motif data indicates that the P2 anchor residue can make the largest individual contribution to affinity of any position in an A2.1-restricted epitope. In this case, the amino acid at the P2 position is the optimally preferred leucine. The PO anchor residue, leucine, is favorable, though not as strongly preferred, nor is the wild type PO residue necessarily the most preferred for that position. Consistent with the favorable results obtained with Nle and Nva for the other epitopes, similar improvements can be obtained substituting Nle and Nva with this sequence. Finally, even similar binding characteristics, if paired with alterations that help circumvent whatever tolerance to the epitope may exist, can increase the effective immunogenicity of the peptide.

The rationale for various substitutions has been set forth above. The particular substitutions investigated for the $PRAME_{425-433}$ epitope follow the same logic and are disclosed in the Examples 17-20 and FIGS. 16-18. Substitutions were made at the primary anchor positions P2 and PO(P9), the secondary anchor positions P1 and PO-1 (P8). Substitutions were also made in the TCR interacting positions (in addition to secondary anchor positions) P3 and P6. Selected substitutions have impact on binding and/or stability of MHC class I—peptide complexes: a key feature in determining the immunological properties of peptides. In addition, due to T cell repertoire considerations and to circumvent mechanisms responsible for the limited immunity to native epitopes, substitutions that retain the capability of analogs to interact with T cell receptors recognizing native peptides can be of practical value.

Example 12

Evaluation of Immunologic Properties of Analogs:
Cross-Reactivity and Functional Avidity The immunologic properties of peptides can be described as a function of binding to MHC molecules ($K_{on}$ and $K_{off}$) and TCR (affinity of interaction between TCR and MHC-peptide complexes). Modifications of primary MHC anchor residues generally have a significant degree of predictability in regard to overall impact on binding to MHC molecules.

Modifications of secondary MHC anchor residues can impact the affinity of interaction of the MHC-peptide complex to TCR alone with the $K_{on}$ and $K_{off}$ relative to peptide-MHC interaction.

A methodology was devised to allow rapid and rational screening of peptide analogs in a fashion coherent with proposed methods of use and modeling the overall immunologic properties ($K_{on}$ and $K_{off}$ relative to MHC interaction and TCR binding properties in an integrated fashion). In some instances, the method included generating T cell lines against a natural (non-mutated) epitope (SSX-$2_{41-49}$), and using an immunization strategy potent enough to generate a useful response in transgenic mice carrying human MHC (such as the A2 allele). Peptide analogs were interrogated ex vivo in the presence of competent APCs and the functional impact of T cells specific for natural (non-mutated) epitopes measured. The evaluation was done at various concentrations of analog, because the expected effect was biphasic in the case of cross reactive peptides (activating at limited concentrations and inhibiting at higher concentrations, due to antigen-induced cell death, AICD). Measurement of the following three parameters were used to define basic and useful characteristics of peptide analogs:

1. Minimal required concentration of peptide analog to trigger effects indicative of T cell activation (e.g. cytokine production);
2. Maximal (peak value) effect (e.g. cytokine production) at any analog concentration;
3. Analog concentration at peak value of activating effect (e.g., cytokine concentration)

For example, analogs that result in reduced values associated with parameters #1 and 3 but increased #2, can be useful. Use of natural epitope and unrelated non-cross reactive peptides as references is valuable in identifying classes of analogs of potential value. Analogs that display properties quantitatively comparable to or even modestly attenuated from those of natural epitopes are still deemed useful in light of the fact that while they retain cross-reactivity, they may display immunologic properties that are distinct from those of the natural peptide—for example, lower propensity to induce AICD or ability to break tolerance or restore responsiveness in vivo.

Some advantages of this screening strategy include the practicality and rapidity, use of more relevant polyclonal T cell lines instead of potentially biased T cell clones as a read out, and the composite value, integrating parameters such as $K_{on}$, $K_{off}$ and TCR affinity that can translate into cross-reactivity and functional avidity of peptide-MHC complexes relative to TCR. These parameters can be predictive of the in vivo immunologic properties and thus can delineate useful panels of peptide analogs to undergo further evaluation, optimization and practical applications. Analogs that bind to MHC and retain cross-reactivity against TCR specific for the nominal wild-type peptide are predicted to trigger a measurable effect in this assay. The overall methodology is presented in FIG. 11.

The method used for the generation of T cell lines was the following: HHD transgenic mice carrying an A2 human allele (Pascolo et al., *J. Exp Med.* 185(12):2043-51, 1997, which is hereby incorporated herein by reference in its entirety) were immunized with 50 μg of SSX-2 natural epitope (41-49) admixed with 25 μg of plpC at day 0, 4, 14 and 18 by bilateral administration into the inguinal lymph nodes. At 7 days after the last boost, the mice were sacrificed and a suspension of splenocytes prepared at $5\times10^6$ million cells/ml in complete HL-1 medium. Cells were incubated with different concentrations of peptide for 48 hours in flat-bottomed 96-well plates (200 μg/well) and for an additional 24 hours with rIL-2 at 10 U/ml added to the wells. The supernatant was harvested and the concentration of IFN-gamma assessed by standard methods such as ELISA.

Examples 13-16

Testing of $PSMA_{288-297}$ Analogs

The analogs listed in FIGS. 12 and 13 were tested for various properties such as improved affinity and stability of binding, cross-reactivity with the native epitope, and immunogenicity as follows in Examples 13-16.

Example 13

Cross-Reactivity and Functional Avidity of Analogs Substituted at Single Position Using the procedures described in application Ser. Nos. 11/455,278 and 11/454,633, each of which is hereby incorporated by reference in its entirety, the binding characteristics of $PSMA_{288-297}$ and analogs were assessed in comparison to each other see (see FIG. 12). The positive control for binding was melan-$A_{26-35}$ A27L. Cross reactivity with the native epitope was assessed by using the analog peptides to stimulate IFN-gamma secretion from a T cell line specific for the native epitope, essentially as described in Example 12. The data shown in FIG. 12 was generated by stimulating with 10 μg/ml of analog (approximately 10 μM). This concentration generally resulted in maximal or near-maximal IFN-gamma production for the analogs and thus was chosen to represent cross-reactivity.

The observed affinities of the analogs are resorted in FIG. 12 as $ED_{50}$s. Met, Ile, Gln, Val, Nva, Nle, and Abu were substituted at the P2 position, and generally resulted in similar affinity. The Nle and Met substitutions also maintained similar stability of binding, measured as half-time of dissociation in hours. The Val, Nva, and Abu analogs elicited a similar level of IFN-gamma production.

Val, Leu, Nva, and Nle were substituted for the Ile at the PO primary anchor position. All four had similar binding affinity. The Val and Nva substitutions improved the stability of binding and increased the amount of IFN-gamma produced, indicating cross-reactivity and that the analogs can have improved immunogenicity.

The Ser, Ala, Sar, and Abu substitutions at P1 maintained similar binding characteristics but had marginally similar cross-reactivity. The Ala, Leu, Ser, and Thr substitutions at the PO-1 position also maintained similar binding characteristics. Finally, the Trp substitution at P3 exhibited affinity and stability of binding that were both increased about twofold and IFN-gamma production that was within twofold of the native peptide, all generally similar values.

Example 14

Cross-Reactivity and Functional Avidity of Analogs Substituted at Two Positions The pattern seen above, that substitutions in this epitope did not greatly impair binding affinity, continued with the double substitutions examined (FIG. 13) which uniformly displayed similar or improved binding affinity compared to the native peptide. Among the analogs with substitutions at both primary anchor positions, those with Nva of Nle at P2 and Val at PO, and Val at P2 and Nva at PO displayed improved binding stability and the former two increased IFN-gamma production (data not shown for the $3^{rd}$ analog). The Val and Nva substitutions at PO were also paired with Ala and Abu substitutions at P1. These analogs all had robust binding stability and IFN-gamma production that was improved compared to the single PO substitutions, thus further improving the P1 substitutions. The PO Nva substitution was also able to maintain better cross-reactivity than PO V when combined with the P3 Trp substitution, although the various binding parameters were generally similar.

Example 15

Cross-Reactivity and Functional Avidity of Analogs Substituted at Three Positions Triple substitutions at P1, P2, and P3; P1, P2, and PO; P2, P3, and PO; and P1, P3, and PO were made (FIG. 14). In all cases, the P1 substitution was Ala, the P3 substitution was Trp, and the PO substitution Val or Nva. As above, affinity at least similar to the native peptide was maintained. For the P1, P2, P3 class Nva and Nle at P2 improved the stability of binding. This P2 Nva analog elicited a similar amount of IFN-gamma while the Nle analog showed a substantial increase.

For the P1, P2, PO class, Nva and Val at P2 and PO in either combination improved binding stability. This P2 Nva PO Val analog also showed a substantial increase in IFN-gamma production. (Data not shown). Val at both P2 and PO in this triple substitution showed binding stability and IFN-gamma production that was nearly halved from that of the native peptide.

For the P2, P3, PO group, only the Nva/W/V analog showed improved binding or IFN-gamma production. For the two P1, P3, PO analogs examined PO of Val or Nva improved binding stability.

Example 16

Cross-Reactive Immunogenicity of Various Analogs

Groups of HHD transgenic mice (n=8) were immunized with peptide (natural epitope $PSMA_{288-297}$, or analogs bearing substitutions at primary or secondary anchor residues) by direct inoculation into the inguinal lymph nodes, with 25 µg in 25 µg of PBS+12.5 µg of pI:C to each lymph node at day 0, 3, 14 and 17.

Mice were sacrificed at 10 days after the last boost, and splenocytes prepared and assessed for IFN-γ production by ELISPOT analysis. Various numbers of splenocytes/well were stimulated with 10 µg/ml of native peptide in ELISPOT plates coated with anti-IFN-γ antibody. At 48 hours after incubation, the assay was developed and the frequency of cytokine-producing T cells that recognized native $PSMA_{288-297}$ peptide was automatically counted. The data is represented in FIG. 15 as the number of spot forming colonies/well (mean of triplicates+SD). The data show increased priming of immune responses against the native epitope achieved by the I297V and P290W analogs, with the other analogs showing slightly higher (but significant) activity than the native peptide (I297Nva or G288Abu or L289Nle I297Nva). To the extent that the poor immunogenicity of the native epitope reflects tolerance, the improved activity of these analogs represents tolerance breaking.

Examples 17-20

Testing of $PRAME_{425-433}$ Analogs

The analogs listed in FIGS. 16-18 were tested for various properties such as improved affinity and stability of binding, cross-reactivity with the native epitope, and immunogenicity as follows in Examples 17-20. Using the procedures described in application Ser. Nos. 11/455,278 and 11/454,633, each of which is hereby incorporated by reference in its entirety, the HLA-A*0201 binding characteristics of $PRAME_{425-433}$ and 69 analogs were assessed in comparison to each other. The positive control for binding was melan-$A_{26-35}$ A27L. The observed affinities of the analogs are resorted as % binding (compared to the positive control) and $ED_{50}$, and stability of binding as half time of dissociation. Cross reactivity with the native epitope was assessed by using the analog peptides to stimulate IFN-gamma secretion from a T cell line specific for the native epitope, essentially as described in Example 12. The data shown in FIGS. 16-18 were generated by stimulating with analog peptide at approximately 0.3 µM. The results were collected from three separate experiments and were normalized to the amount of IFN-γ elicited by the native peptide in each. In some cases, the reported values are the average of two determinations. An asterisk "*" indicates that IFN-γ production was not distinguishable from background.

Example 17

Cross-Reactivity and Functional Avidity of Analogs Substituted at a Single Position (FIG. 16)

Single substitutions of Val, Met, Ile, Nle, Nva, and Abu were made for the Leu at the P2 primary anchor position. All of these analogs exhibited % binding within 20% of the native peptide. The ED50 for the Met analog had an affinity comparable to the native peptide while the Nva and Ile analogs' affinities were reduced within about 3-fold, but were still comparable to the $PSMA_{88-287}$ epitope. All of the P2 substitutions maintained binding stability at least similar to the native peptide. The Met, Nle, and Nva analogs elicited IFN-γ production within twofold of the native peptide and the Val analog somewhat less.

Single substitution of Lys, Phe, Tyr, Thr, Orn (ornithine), and Hse (homoserine) were made for the Ser at the P1 position. All of these analogs exhibited % binding within 20% of the native peptide except for the Phe analog which exceeded that range on the high side. The ED50 for the Lys analog was reduced by almost 6-fold, but the other five analogs had affinities within threefold of the native peptide. Stability of binding was generally similar to the native peptide with the Phe P1 analog showing greatest binding stability in this group with a half time of dissociation of 17.7 hours compared to 12.2 hours for the native peptide. With the exception of the Lys P1 analog, which elicited 40% of the IFN-γ of the native peptide, all of these analogs were considered cross-reactive as they elicited IFN-γ production within twofold of the native peptide.

Single substitutions of Val, Ile, Ala, Nle, Nva, Abu, were made to the PO anchor position, as well as modifying the carboxy-terminus by the addition of an amide group. All of these analogs exhibited % binding within 20% of the native peptide. ED50 measurements ranged from more than 10-fold less for the Ala substitution to a comparable value for the Nle substitution; the Nva substitution and C-terminal amide were also within 3-fold of the ED50 for native peptide. Stability of binding was also generally similar with outliers of the Nva analog at the high end, t1/2 of 17.2 hours, and the C-terminal amide at the low end with a significantly reduced t1/2 of only 3 hours. The Val, Ile, Ala, and Abu PO analogs exhibited less preferred cross-reactivity, but the others elicited IFN-γ production within twofold of the native peptide.

Single substitutions at positions primarily affecting TCR interactions were also made: Nle, Nva, and Abu at P3 and P6, and Ala, Ser, and Sar at P8. The P6 Nva analog produced IFN-γ within twofold of that of the native peptide, though the P6 Abu analog was close at 44%.

Example 18

Cross-Reactivity and Functional Avidity of Analogs Substituted at Two Positions

Double substitution analogs were created at P1 and P2, P2 and PO, and P1 and PO using various combinations of the single substitutions above (FIGS. 17A and 17B). None of the P1-P2 double substitutions examined had radical changes to binding affinity or stability, but none exhibited significant cross-reactivity in the IFN-γ assay. A similar pattern was seen with the P2-PO double substitution analogs, however, the L426Nva L433Nle analog exhibited a significant level of cross-reactivity with the native peptide in the IFN-γ assay along with its similar, somewhat improved binding characteristics. Finally, for the P1-PO double substitutions, the examined analogs also conformed to the general pattern of having at least similar binding characteristics, but eliciting negligible IFN-γ in the cross-reactivity assay. The exceptions in this grouping were the S425F L433Nle analog, which exhibited somewhat improved binding stability and significant cross-reactivity, and the S425F L433Nle analog, which had a more that fourfold reduced $ED_{50}$, a nearly doubled halftime of dissociation, and elicited more IFN-γ than the native peptide.

Example 19

Cross-Reactivity and Functional Avidity of Analogs Substituted at Three Positions Four triple substitution analogs were investigated, having Phe or Thr at P1, Nva or Met at P2, and Nle at PO. The S425T L426M L433Nle analog had similar affinity whereas the affinity was improved for the other three analogs. Both analogs with P2 Nva substitutions displayed increased stability of binding and significant levels of cross-reactivity. See FIG. 18.

Example 20

Cross-Reactive Immunogenicity of the L426Nva L433Nle Analog

Two groups of HHD transgenic mice (n=8) were immunized with a pCTLR2 plasmid expressing $PRAME_{425-433}$, described in application Ser. Nos. 11/455,278 and 11/454,633, each of which is hereby incorporated by reference in its entirety, by direct inoculation into the inguinal lymph nodes of 25 μg in 25 μg of PBS to each lymph node at day 0, 3, 14 and 17. This was followed by two peptide boosts (2.5 μg) at day 28 and 31, of native peptide or the PRAME epitope analog L426Nva L433Nle.

Mice were sacrificed at 10 days after the last boost, and splenocytes prepared and assessed for IFN-γ production after in vitro stimulation at $0.5\times10^6$ cells/well, with 10 μg/ml of native peptide. At 48 hours after incubation, the supernatant was harvested and the concentration of IFN-γ produced in response to the $PRAME_{425-433}$ peptide was measured by ELISA. The data are presented in FIG. 19 and show a significant enhancement of IFN-γ production in mice boosted with the $PRAME_{425-433}$ L426Nva L433Nle analog.

In addition to those already disclosed in this application, the following applications are hereby expressly incorporated by reference in their entireties. Useful methods for using the disclosed analogs in inducing, entraining, maintaining, modulating and amplifying class I MHC-restricted T cell responses, and particularly effector and memory CTL responses to antigen, are described in U.S. Pat. Nos. 6,994,851 (Feb. 7, 2006) and 6,977,074 (Dec. 20, 2005) both entitled "A Method of Inducing a CTL Response"; U.S. Provisional Application No. 60/479,393, filed on Jun. 17, 2003, entitled "METHODS TO CONTROL MHC CLASS I-RESTRICTED IMMUNE RESPONSE"; and U.S. patent application Ser. No. 10/871,707 (Pub. No. 2005 0079152) and Provisional U.S. Patent Application No. 60/640,402 filed on Dec. 29, 2004, both entitled "Methods to elicit, enhance and sustain immune responses against MHC class I-restricted epitopes, for prophylactic or therapeutic purpose". The analogs can also be used in research to obtain further optimized analogs. Numerous housekeeping epitopes are provided in U.S. application Ser. Nos. 10/117,937, filed on Apr. 4, 2002 (Pub. No. 20030220239 A 1), and 10/657,022 (20040180354), and in PCT Application No. PCT/US2003/027706 (Pub. No. WO04022709A2), filed on Sep. 5, 2003; and U.S. Provisional Application Nos. 60/282,211, filed on Apr. 6, 2001; 60/337,017, filed on Nov. 7, 2001; 60/363,210 filed on Mar. 7, 2002; and 60/409,123, filed on Sep. 5, 2002; each of which applications is entitled "Epitope Sequences". The analogs can further be used in any of the various modes described in those applications. Epitope clusters, which may comprise or include the instant analogs, are disclosed and more fully defined in U.S. patent application Ser. No. 09/561,571, filed on Apr. 28, 2000, entitled EPITOPE CLUSTERS. Methodology for using and delivering the instant analogs is described in U.S. patent application Ser. No. 09/380,534 and U.S. Pat. No. 6,977,074 (Issued Dec. 20, 2005) and in PCT Application No. PCTUS98/14289 (Pub. No. WO9902183A2), each entitled A "METHOD OF INDUCING A CTL RESPONSE". Beneficial epitope selection principles for such immunotherapeutics are disclosed in U.S. patent application Ser. Nos. 09/560,465, filed on Apr. 28, 2000, 10/026,066 (Pub. No. 20030215425 A1), filed on Dec. 7, 2001, and 10/005,905 filed on Nov. 7, 2001, all entitled "Epitope Synchronization in Antigen Presenting Cells"; 6,861,234 (issued 1 Mar. 2005; application Ser. No. 09/561,074), entitled "Method of Epitope Discovery"; Ser. No. 09/561,571, filed Apr. 28, 2000, entitled EPITOPE CLUSTERS; Ser. No. 10/094,699 (Pub. No. 20030046714 A1), filed Mar. 7, 2002, entitled "Anti-Neovasculature Preparations for Cancer"; application Ser. No. 10/117,937 (Pub. No. 20030220239 A1) and PCTUS02/11101 (Pub. No. WO02081646A2), both filed on Apr. 4, 2002, and both entitled "EPITOPE SEQUENCES"; and application Ser. No. 10/657,022 and PCT Application No. PCT/US2003/027706 (Pub. No. WO04022709A2), both filed on Sep. 5, 2003, and both entitled "EPITOPE SEQUENCES". Aspects of the overall design of vaccine plasmids are disclosed in U.S. patent application Ser. Nos. 09/561,572, filed on Apr. 28, 2000, entitled "Expression Vectors Encoding Epitopes of Target-Associated Antigens" and 10/292,413 (Pub. No. 20030228634 A1), filed on Nov. 7, 2002, entitled "Expression Vectors Encoding Epitopes of Target-Associated Antigens and Methods for their Design"; 10/225,568 (Pub No. 2003-0138808), filed on Aug. 20, 2002, PCT Application No. PCT/US2003/026231 (Pub. No. WO 2004/018666), filed on Aug. 19, 2003, both entitled "EXPRESSION VECTORS ENCODING EPITOPES OF TARGET-ASSOCIATED ANTIGENS"; and U.S. Pat. No. 6,709,844, entitled "AVOIDANCE OF UNDESIRABLE REPLICATION INTERMEDIATES IN PLASMID PROPAGATION". Specific antigenic combinations of particular benefit in directing an immune response against particular cancers are disclosed in Provisional U.S. patent Application No. 60/479,554, filed on Jun. 17, 2003 and U.S. patent application Ser. No. 10/871,708, filed on Jun. 17, 2004 and PCT Patent Application No. PCT/US2004/019571 (Pub. No. WO 2004/112825), all entitled "Combinations of tumor-associated antigens in vaccines for various types of cancers". Antigens associated with tumor neovasculature (e.g., PSMA, VEGFR2, Tie-2) are also useful in connection with cancerous diseases, as is disclosed in U.S. patent application Ser. No. 10/094,699 (Pub. No. 20030046714 A1), filed Mar. 7, 2002, entitled "Anti-Neovasculature Preparations for Cancer". Methods to trigger, maintain, and manipulate immune responses by targeted administration of biological response modifiers are disclosed U.S. Provisional Application No. 60/640,727, filed on Dec. 29, 2004. Methods to bypass CD4+ cells in the induction of an immune response are disclosed in U.S. Provisional Application No. 60/640,821, filed on Dec. 29, 2004. Exemplary diseases, organisms and antigens and epitopes associated with target organisms, cells and diseases are described in U.S. Pat. No. 6,977,074 (issued Dec. 20, 2005) filed Feb. 2, 2001 and entitled "METHOD OF INDUCING A CTL RESPONSE". Exemplary methodology is found in U.S. Provisional Application No. 60/580,969, filed on Jun. 17, 2004, and U.S. Patent Application No. 2006-0008468-A1, published on Jan. 12, 2006, both entitled "COMBINATIONS OF TUMOR-ASSOCIATED ANTIGENS IN DIAGNOTISTICS FOR VARIOUS TYPES OF CANCERS". Methodology and compositions are also disclosed in U.S. Provisional Application No. 60/640,598, filed on Dec. 29, 2004, entitled "COMBINATIONS OF TUMOR-ASSOCIATED ANTIGENS IN COMPOSITIONS FOR VARIOUS TYPES OF CANCER". The integration of diagnostic techniques to assess and monitor immune responsiveness with methods of immunization including utilizing the instant analogs is discussed more fully in Provisional U.S. Patent Application No. 60/580,964 filed on Jun. 17, 2004 and U.S. Patent Application No. US-2005-0287068-A1, published on Dec. 29, 2005) both entitled "Improved efficacy of active immunotherapy by integrating diagnostic with therapeutic methods". The immunogenic polypeptide encoding vectors are disclosed in U.S. patent application Ser. No. 10/292,413 (Pub. No. 20030228634 A 1), filed on Nov. 7, 2002, entitled Expression Vectors Encoding Epitopes of Target-Associated Antigens and Methods for their Design, and in U.S. Provisional Application No. 60/691,579, filed on Jun. 17, 2005, entitled "Methods and compositions to elicit multivalent immune responses against dominant and subdominant epitopes, expressed on cancer cells and tumor stroma". Additional useful disclosure, including methods and compositions of matter, is found in U.S. Provisional Application No. 60/691,581, filed on Jun. 17, 2005, entitled "Multivalent Entrain-and-Amplify Immunotherapeutics for Carcinoma". Further methodology, compositions, peptides, and peptide analogs are disclosed in U.S. Provisional Application Nos. 60/581,001 and 60/580,962, both filed on Jun. 17, 2004, and respectively entitled "SSX-2 PEPTIDE ANALOGS" and "NY-ESO PEPTIDE ANALOGS." Each of the applications and patents mentioned in the above paragraphs is hereby incorporated by reference in its entirety for all that it teaches. Additional analogs, peptides and methods are disclosed in U.S. Patent Application Publication No 20060063913, entitled "SSX-2 PEPTIDE ANALOGS"; and U.S. Patent Publication No. 2006-0057673 A1, published on Mar. 16, 2006, entitled "EPITOPE ANALOGS"; and PCT Application Publication No. WO/2006/009920, entitled "EPITOPE ANALOGS"; all filed on Jun. 17, 2005. Further methodology and compositions are disclosed in U.S. Provisional Application No. 60/581,001, filed on Jun. 17, 2004, entitled "SSX-2 PEPTIDE ANALOGS", and to U.S. Provisional Application No. 60/580,962, filed on Jun. 17, 2004, entitled "NY-ESO PEPTIDE ANALOGS"; each of which is incorporated herein by reference in its entirety. As an example, without being limited thereto each reference is incorporated by reference for what it teaches about class 1 MHC-restricted epitopes, analogs, the design of analogs, uses of epitopes and analogs, methods of using and making epitopes, and the design and use of nucleic acid vectors for their expression. Other applications that are expressly incorporated herein by reference are: U.S. patent application Ser. No. 11/156,253 (Publication No. 20060063913), filed on Jun. 17, 2005, entitled "SSX-2 PEPTIDE ANALOGS"; U.S. patent application Ser. No. 11/155,929, filed on Jun. 17, 2005 entitled "NY-ESO-1 PEPTIDE ANALOGS" (Publication No. 20060094661); U.S. patent application Ser. No. 11/321,967, filed on Dec. 29, 2005, entitled "METHODS TO TRIGGER, MAINTAIN AND MANIPULATE IMMUNE RESPONSES BY TARGETED ADMINISTRATION OF BIOLOGICAL RESPONSE MODIFIERS INTO LYMPHOID ORGANS"; U.S. patent application Ser. No. 11/323,572, filed on Dec. 29, 2005 entitled "METHODS TO ELICIT ENHANCE AND SUSTAIN IMMUNE REPONSES AGAINST MCH CLASS 1 RESTRICTED EPITOPES, FOR PROPHYLACTIC OR THERAPEUTIC PURPOSES"; U.S. patent application Ser. No. 11/323,520, filed Dec. 29, 2005, entitled "METHODS TO BYPASS CD4+ CELLS IN THE INDUCTION OF AN IMMUNE RESPONSE"; U.S. patent application Ser. No. 11/323,049, filed Dec. 29, 2005, entitled "COMBINATION OF TUMOR-ASSOCIATED ANTIGENS IN COMPOSITIONS FOR VARIOUS TYPES OF CANCERS"; U.S. patent application Ser. No. 11/323,964, filed Dec. 29, 2005, entitled "COMBINATIONS OF TUMOR-ASSOCIATED ANTIGENS IN DIAGNOSTICS FOR VARIOUS TYPES OF CANCERS"; U.S. Provisional Application Ser. No. 60/691,889, filed on Jun. 17, 2005 entitled "EPITOPE ANALOGS."

What is claimed:

1. An immunogenic product comprising a plurality of compositions comprising one or more nucleic acid compositions and one or more peptide compositions; wherein the one or more nucleic acid compositions are capable of expressing two or more class I MHC restricted epitopes, wherein the two or more class I MHC restricted epitopes comprise a PRAME epitope and a PSMA epitope, wherein the PRAME epitope is selected from PRAME$_{425-433}$ (SEQ ID NO. 3) or a cross-reactive analogue thereof, and wherein the PSMA epitope is selected from PSMA$_{288-297}$ (SEQ ID NO. 4) or a cross-reactive analogue thereof, and wherein the one or more peptide compositions comprise one or more class I MHC restricted epitopes, wherein the one or more class I MHC restricted epitopes comprise the PRAME epitope or the PSMA epitope or both, and wherein PRAME epitope is selected from PRAME$_{425-433}$ (SEQ ID NO. 3) or a cross reactive analogue thereof and the PSMA epitope is selected from PSMA$_{288-297}$ (SEQ ID NO. 4) or a cross reactive analogue thereof.

2. The immunogenic product of claim 1 wherein said one or more nucleic acid compositions comprise the pRP12 plasmid (SEQ ID NO. 21).

3. The immunogenic product of claim 1 wherein said one or more cross-reactive analogues is selected from the group consisting of S(Nva)LQHLIG(Nle) (SEQ ID NO. 7) and GLPSIPVHPV (SEQ ID NO. 8).

4. The immunogenic product of claim 1 wherein said plurality of compositions comprise:
   a) a nucleic acid molecule capable of expressing a PRAME$_{425-433}$ (SEQ ID NO. 3) class I MHC restricted epitope, or a cross-reactive analogue thereof;
   b) a nucleic acid molecule capable of expressing a PSMA$_{288-297}$ (SEQ ID NO. 4) class I MHC restricted epitope, or a cross-reactive analogue thereof;
   c) a peptide consisting essentially of said PRAME$_{425-433}$ (SEQ ID NO. 3) epitope, or a cross-reactive analogue thereof; and
   d) a peptide consisting essentially of said PSMA$_{288-297}$ (SEQ ID NO. 4) epitope, or a cross-reactive analogue thereof.

5. The product of claim 4 wherein the nucleic acid molecules of a) and b) are part of the same composition.

6. The product of claim 5 wherein the nucleic acid molecules are the same.

7. The product of claim 6 wherein the nucleic acid molecule comprises a sequence encoding the liberation sequence of pRP12 (SEQ ID NO. 14).

8. The product of claim 7 wherein the nucleic acid comprises a sequence encoding the immunogenic polypeptide of pRP12 (SEQ ID NO. 17).

9. The product of claim 7 wherein the nucleic acid molecule is pRP12 (SEQ ID NO. 21).

10. The product of claim 4 wherein said PRAME analogue in c) is S(Nva)LQHLIG(Nle) (SEQ ID NO. 7).

11. The product of claim 4 wherein said PSMA analogue in d) is GLPSIPVHPV (SEQ ID NO. 8).

12. The immunogenic product of claim 1 wherein said plurality of compositions further comprise:
   a) a nucleic acid molecule capable of expressing an SSX-2 class I MHC restricted epitope, or analogue thereof;

b) a nucleic acid molecule capable of expressing an NY-ESO-1 class I MHC restricted epitope, or analogue thereof;

c) a peptide consisting essentially of said SSX-2 epitope, or analogue thereof;

d) a peptide consisting essentially of said NY-ESO-1 epitope, or analogue thereof.

13. The product of claim 12 wherein the nucleic acid molecules of a) and b) are part of the same composition.

14. The product of claim 13 wherein the nucleic acid molecules are the same.

15. The product of claim 14 wherein the nucleic acid molecule comprises a sequence encoding the liberation sequence of pBPL(SEQ ID NO. 13).

16. The product of claim 14 wherein the nucleic acid comprises a sequence encoding the immunogenic polypeptide of pBPL (SEQ ID NO. 16).

17. The product of claim 16 wherein the nucleic acid molecule is pBPL (SEQ ID NO. 20).

18. The product of claim 12 wherein the SSX-2 epitope is SSX-2$_{41-49}$ (SEQ ID NO. 1).

19. The product of claim 12 wherein the NY-ESO-1 epitope is NY-ESO-1$_{157-165}$ (SEQ ID NO. 2).

20. The product of claim 12 wherein said SSX-2 analogue in c) is KVSEKIFYV (SEQ ID NO. 5).

21. The product of claim 12 wherein said NY-ESO-1 analogue in d) is S(Nva)LMWITQV (SEQ ID NO. 6).

22. The immunogenic product of claim 1 wherein said plurality of compositions further comprises:

i) a nucleic acid molecule capable of expressing a Melan-A class I MHC restricted epitope, or analogue thereof;

ii) a nucleic acid molecule capable of expressing a Tyrosinase class I MHC restricted epitope, or analogue thereof;

iii) a peptide consisting essentially of said Melan-A epitope, or analogue thereof; and vi) a peptide consisting essentially of said Tyrosinase epitope, or analogue thereof.

23. The product of claim 22 wherein the nucleic acid molecules of i) and ii) are part of the same composition.

24. The product of claim 23 wherein the nucleic acid molecules are the same.

25. The product of claim 24 wherein the nucleic acid molecule comprises a sequence encoding the liberation sequence of pSEM (SEQ ID NO. 15).

26. The product of claim 25 wherein the nucleic acid comprises a sequence encoding the immunogenic polypeptide of pSEM (SEQ ID NO. 18).

27. The product of claim 26 wherein the nucleic acid molecule is pSEM.

28. The product of claim 22 wherein the Melan-A epitope is Melan-A$_{26-35}$ (SEQ ID NO. 9).

29. The product of claim 22 wherein the Tyrosinase epitope is Tyrosinase$_{369-377}$ (SEQ ID NO. 10).

30. The product of claim 22 further comprising:

i) a nucleic acid molecule capable of expressing an SSX-2 class I MHC restricted epitope, or analogue thereof; and ii) a nucleic acid molecule capable of expressing an NY-ESO-1 class I MHC restricted epitope, or analogue thereof.

31. The product of claim 30 further comprising a peptide consisting essentially of an NY-ESO-1 epitope.

32. The product of claim 30 or 31 further comprising a peptide consisting essentially of an SSX-2 epitope.

33. The product of claim 22 wherein said Melan-A analogue in iii) is E(Nva)AGIGILTV (SEQ ID NO. 11).

34. The product of claim 22 wherein said Melan-A analogue in i) or iii) is the A27L analogue of the Melan-A$_{26-35}$ (SEQ ID NO. 9).

35. The product of claim 22 wherein said Tyrosinase analogue in iv) is YMDGTMSQ(Nva) (SEQ ID NO. 12).

36. A method of treating cancer comprising administering the product of claim 1 to a patient in need thereof.

37. The method of claim 36, wherein the cancer is a breast cancer, an ovarian cancer, a pancreatic cancer, a prostate cancer, a colon cancer, a bladder cancer, a lung cancer, a liver cancer, a stomach cancer, a testicular cancer, an uterine cancer, a brain cancer, a lymphatic cancer, a skin cancer, a bone cancer, a kidney cancer, a rectal cancer, a melanoma, a glioblastoma, or a sarcoma.

* * * * *